(12) United States Patent
Hu et al.

(10) Patent No.: US 11,667,704 B2
(45) Date of Patent: Jun. 6, 2023

(54) ANTI-IL-17 ANTIBODY/TNFR ECD FUSION PROTEIN AND USE THEREOF

(71) Applicants: BEIJING BEYOND BIOTECHNOLOGY CO., LTD, Beijing (CN); HANGZHOU POLYMED BIOPHARMACEUTICALS, INC., Zhejiang (CN)

(72) Inventors: Pinliang Hu, Beijing (CN); Jing Zou, Beijing (CN); Weidong Hong, Beijing (CN); Yun He, Beijing (CN); Jie Bai, Beijing (CN); Lingyun Song, Beijing (CN); Wendi Yang, Beijing (CN); Zhijian Lv, Hangzhou (CN); Shaoyun Xiang, Hangzhou (CN)

(73) Assignees: BEIJING BEYOND BIOTECHNOLOGY CO., LTD, Beijing (CN); HANGZHOU POLYMED BIOPHARMACEUTICALS, INC., Hangzhou (CN)

(*) Notice: Subject to any disclaimer, the term of this patent is extended or adjusted under 35 U.S.C. 154(b) by 162 days.

(21) Appl. No.: 16/764,788

(22) PCT Filed: Nov. 6, 2018

(86) PCT No.: PCT/CN2018/114079
§ 371 (c)(1),
(2) Date: May 15, 2020

(87) PCT Pub. No.: WO2019/096026
PCT Pub. Date: May 23, 2019

(65) Prior Publication Data
US 2021/0261654 A1 Aug. 26, 2021

(30) Foreign Application Priority Data
Nov. 16, 2017 (CN) .......................... 201711137039.8

(51) Int. Cl.
| | | |
|---|---|---|
| C07K 16/46 | (2006.01) | |
| C07K 14/00 | (2006.01) | |
| A61K 39/00 | (2006.01) | |
| C12N 15/00 | (2006.01) | |
| C07K 16/24 | (2006.01) | |
| A61P 29/00 | (2006.01) | |
| C12N 15/52 | (2006.01) | |

(52) U.S. Cl.
CPC ............ *C07K 16/244* (2013.01); *A61P 29/00* (2018.01); *C12N 15/52* (2013.01); *A61K 2039/505* (2013.01); *C07K 2317/565* (2013.01)

(58) Field of Classification Search
None
See application file for complete search history.

(56) References Cited

U.S. PATENT DOCUMENTS

| 5,891,680 A | * | 4/1999 | Lieschke | ................. A61P 35/00 |
| | | | | 435/69.51 |
| 2011/0091378 A1 | * | 4/2011 | Dudas | ..................... A61P 37/06 |
| | | | | 424/1.49 |
| 2013/0084291 A1 | * | 4/2013 | Seehra | ............... C12N 15/8257 |
| | | | | 424/134.1 |
| 2016/0326241 A1 | * | 11/2016 | Auer | .................... C07K 16/244 |
| 2017/0327571 A1 | * | 11/2017 | Liu | ...................... A61K 39/395 |

FOREIGN PATENT DOCUMENTS

| CN | 104311670 B | 5/2017 |
| WO | WO 2009/058383 A2 | 5/2009 |
| WO | WO 2009/064777 A2 | 5/2009 |

OTHER PUBLICATIONS

Chen et al. Mapping the domains critical for the binding of human tumor necrosis factor alpha to its two receptors. The Journal of Biological Chemistry vol. 270, No. 6:2874-2878 (1995). (Year: 1995).*
Ulloa-Aguirre et al. Pharmacologic Rescue of Conformationally-Defective Proteins: Implications for the Treatment of Human Disease Traffic 5:821-837; (2004). (Year: 2004).*
Bernier et al. Pharmacological chaperone action of G-protein-coupled receptors. Curr. Opin. Pharmacol. 4:528-533; (2004). (Year: 2004).*
Fenton et al. Rheostat positions: A new classification of protein positions relevant to pharmacogenomics Medicinal Chemistry Research 29:1133-1146; (2020). (Year: 2020).*
Gua et al. Protein tolerance to random amino acid change. PNAS USA 101(25):9205-10; (2004). (Year: 2004).*
Bhattacharya et al. Impact of genetic variation on three dimensional structure and function of proteins PLoS ONE 12(3): e0171355, (2017). (Year: 2017).*
Davies et al. Structural determinants of unique properties of human IgG4-Fc. Journal of Molecular Biology, vol. 426:630-644; (2014). (Year: 2014).*
Yang et al. The pharmacological efficacy of the anti-IL17scFv and sTNFR1 bispecific fusion protein in inflammation mouse stimulated by LPS. Biomedicine and Pharmacotherapy 92:905-912, (Aug. 2017). (Year: 2017).*

* cited by examiner

*Primary Examiner* — Elizabeth C. Kemmerer
*Assistant Examiner* — Regina M DeBerry
(74) *Attorney, Agent, or Firm* — Hoxie & Associates LLC

(57) ABSTRACT

The invention relates to the field of medical biotechnology. Specifically, the present invention relates to a fusion protein containing an anti-interleukin-17 antibody and a tumor necrosis factor receptor extracellular region, a polynucleotide encoding the fusion protein, a vector comprising the polynucleotide, a host cell comprising the polynucleotide or the vector, and the use of the fusion protein for the treatment, prevention, and/or diagnosis of a related disease in an individual.

2 Claims, 3 Drawing Sheets

Specification includes a Sequence Listing.

ANTI-IL-17 ANTIBODY/TNFR ECD FUSION PROTEIN AND USE THEREOF

CROSS-REFERENCE TO RELATED APPLICATIONS

This application is a National Stage Entry under 35 U.S.C. § 371 of International Application No. PCT/CN2018/114079, filed Nov. 6, 2018, which claims the benefit of priority from Chinese Patent Application No. 201711137039.8, filed on Nov. 16, 2017, the contents of each of which are incorporated herein by reference in their entireties.

REFERENCE TO A SEQUENCE LISTING

This application contains a Sequence Listing as a separate part of the disclosure. The Sequence Listing is incorporated herein by reference.

TECHNICAL FIELD

The invention relates to the field of medical biotechnology. Specifically, the invention relates to a fusion protein of an anti-interleukin-17 (anti-IL-17) antibody and a tumor necrosis factor receptor extracellular domain (TNFR ECD), and a polynucleotide encoding the fusion protein, a vector comprising the polynucleotide, a host cell comprising the polynucleotide or the vector, and the use of the fusion protein for the treatment, prevention and/or diagnosis of a related disease in an individual.

BACKGROUND TECHNIQUE

In 1975, Carswell discovered that a proteinaceous substance in the serum of mice infected by bacteria can cause tumor bleeding and inhibit and kill tumor cells cultured in vitro. The proteinaceous substance is called tumour necrosis factor (TNF), also known as cachectin (Carswell E A et al., An endotoxin-induced serum factor that causes necrosis of tumor. Proc Natl Sci US A.1975 September; 72(9):3666-3670). TNF is classified into two types according to the structure thereof: TNF-α and TNF-0. TNF-α (formerly known as TNF) is a cytokine capable of causing tumor necrosis and produced by activated macrophages, monocytes and T cells, which also known as cachectin, having two forms: soluble form and transmembrane form. TNF-0 is a lymphotoxin (LT) produced by activated T cells and NK cells, and currently the knowledge about its function is limited. At present, more research is on TNF-α, which is a soluble polypeptide consisting of 157 amino acids and has a relative molecular weight of 17,000. TNF-α exists in solution in the form of dimer, trimer or pentamer, and the active form of a mature type TNF-α is a trimer. TNF-α is essential to defend against infectious diseases and cancerous lesions, although it is an immunoregulatory cytokine. On the other hand, when TNF exceeds a certain amount, it can induce various autoimmune diseases (Immune-mediated inflammatory diseases, IMID), such as rheumatoid arthritis (RA), inflammatory bowel disease (IBD), psoriatic arthritis (PsA), vasculitis, ankylosing spondylitis (AS), and juvenile chronic arthritis (JCA) (Scott D L., et al., Tumor necrosis factor inhibitors for rheumatoid arthritis. N Engl J Med. 2006 Aug. 17; 355(7):704-712).

TNF activates signal transduction through its two receptors, TNFR1 and TNFR2. TNFR1 and TNFR2 can activate different signal transduction pathways in cells. Type I TNF-R (also known as TNFR1, CD120a, p55) has 439 amino acid residues long with a molecular weight of 55 kDa and a corresponding mRNA of 4.5 Kbp, expresses on all types of cells, and plays a major role in cytolytic activity. Type II TNFR (also known as TNFR2, CD120b, p75) has 426 amino acid residues long with a molecular weight of 75 kDa and a corresponding mRNA of 3Kbp, expresses only on immune cells and endothelial cells, and is related to signaling and T cell proliferation. Both types of the TNFRs are glycoproteins, comprising three regions: extracellular region, transmembrane region and intracellular region. Type I and type II TNFR have 28% homology in the extracellular region, but no homology in the intracellular region. The structural feature of the TNFR receptor family is that the extracellular region is composed of 4 functional domains, and each of the functional domains (CRD1-CRD4) contains a 6-cysteine CRD. CRD1, also called PLAD, is the basis for forming TNFR complex; CRD2 and CRD3 are TNF-binding regions that bind to TNF-like factors with high affinity. CRD4 and other non-functional extracellular domains are not involved in TNF-like factor binding (Mukai Y et al., Solution of the structure of the TNF-TNFR2 complex. Sci Signal. 2010 Nov. 16; 3 (148):ra83). The equilibrium dissociation constant (Kd) of TNFR1 to TNF-α is only 0.2-0.5 nM, while the equilibrium dissociation constant (Kd) of TNFR2 to TNF-α reaches 0.03-0.07 nM. It can be seen that the affinity of TNFR2 to TNF-α is ten times more than that of TNFR1 (Dembic Z et al., Two human TNF receptors have similar extracellular, but distinct intracellular, domain sequences. Cytokine. 1990 July; 2(4):231-7).

Further, a part of TNFR extracellular region in a body is dissociated from the cell membrane and released into the blood to become a soluble TNF receptor (sTNFR). sTNFR does not mediate signal transduction, but can still bind to TNF-α to neutralize TNF-α activity, inhibit TNF-α-induced cytotoxicity and autoimmune response, and is a natural antagonist of TNF-α.

Anti-TNF drugs have been successfully used in many autoimmune diseases, such as RA, AS, PsA, and Behcet's disease. At present, infliximab, adalimumab, etanercept, certolizumab pegol and golimumab have been approved for clinical treatment.

Infliximab is a human-mouse chimeric monoclonal antibody against TNF-α, consisting of a murine variable region and a human constant region IgG1 (type K). It has high affinity and specificity for both soluble and transmembrane TNF-α. Infliximab binds to transmembrane TNF-α (mTNF-α), which can mediate programmed cell death and has high specificity, so it can reduce non-specific effects on other biological pathways. Infliximab is useful for the treatment of rheumatoid arthritis, vasculitis, ankylosing spondylitis, psoriatic arthritis, ulcerative colitis and chronic severe plaque psoriasis.

Etanercept, whose similar drug in China has a commercial name of "Esaipu", is obtained by linking two full-length extracellular regions of human TNFR2 (p75 TNF receptor) with the Fc region (CH2 and CH3 domains) of human IgG1, and can effectively reduce the amount of TNF-α binding to membrane receptors through binding to and inhibiting TNF-α. By means of competitive inhibition, two TNF-R2 arms can bind to two of the three receptor-binding sites on TNF-α trimer. The binding of TNF-α to a cell surface receptor and the following signal transduction are blocked (Spencer-Green G et al., Etanercept (Enbrel): update on therapeutic use. Ann Rheum Dis. 2000 November; 59 Suppl 1:i46-i49). As a result, TNF-α mediated proinflammatory activity is inhibited. Etanercept is useful for the treatment of rheumatoid arthritis, psoriatic arthritis, vasculitis, ankylosing spondylitis, and juvenile chronic arthritis Adalimumab is a fully human monoclonal antibody against TNF-α. It can bind to soluble TNF-α and transmembrane TNF-α, and prevent the binding of TNF-α to its receptor. In vitro studies have shown that it has an effect on cell lysis and apoptosis induction after binding to transmembrane TNF-α (Shen C, Assche G V, Colpaert S, Maerten P, Geboes K, Rutgeerts P, Ceuppens J L. Adalimumab induces apoptosis of human monocytes: a comparative study with infliximab and etanercept. Aliment Pharmacol Ther 2005 Feb. 1; 21(3):251-258). Adalimumabis is useful for the treatment of rheumatoid arthritis, psoriatic arthritis, vasculitis, ankylosing spondylitis, and Behcet's disease.

Golimumab is a fully human monoclonal antibody against TNF-α. It can be used in the treatment of rheumatoid arthritis, vasculitis, ankylosing spondylitis, psoriatic arthritis, and ulcerative colitis.

Certolizumab is a Fab fragment of an anti-TNF-α IgG1 monoclonal antibody, without Fc fragment. the hinge region covalently linked to two cross-linked 20kD PEGs. Certolizumab is useful for the treatment of rheumatoid arthritis and psoriatic arthritis.

Interleukin-17 (IL-17) is a newly discovered inflammatory cytokine with a variety of biological activities and is one of the important factors in the occurrence and development of certain diseases. IL-17 plays a potent role in recruiting neutrophil granulocytes and promoting the release of a variety of inflammatory cytokines. It is involved in the occurrence and development of various inflammatory and immune diseases in the body, especially closely related to rheumatoid arthritis, asthma, lung infections, tumors, and contact dermatitis. IL-17 receptor (IL-17R) is widely present in various tissues and cells and binds to IL-17 to produce a proinflammatory response. The study of IL-17 family and its receptors has gradually become a focus of medical and molecular biology research.

IL-17 was first cloned in 1995 (Yao Z et al., Herpesvirus saimiri encodes a new cytokine, IL-17, which binds to a novel cytokine receptor. Immunity. 1995, 3(6): 811-821). It is now known that at least six members (IL-17A-F) of the IL-17 family exist in humans and mice. IL-17A was originally named Cytotoxic T Lymphocytes Antigen 8 (CTLA-8). Five other hIL-17 family members (Moseley1 T. A. et al., Interleukin-17 family and IL-17 receptors [J]. Cytokine & Growth Factor Reviews. 2003, 14:155-174) are IL-17B, IL-17C, IL-17D, IL-17F, IL-17E (also known as IL-25), respectively, having 20%-50% homology with IL-17A, wherein IL-17F has the highest homology. IL-17B, IL-17C, IL-17D, IL-17F, and IL-17E all show as homodimers with their conservative carboxy-terminal regions. IL-17 receptor (IL-17R) family includes 5 members (IL-17RA, B, C, D, and E). The functional receptors of the cytokines belonging to IL-17 family are considered to be composed of homodimers or heterodimers. For example, a heterodimer composed of IL-17RA and IL-17RC is a receptor for the homodimer or the heterodimer of IL-17 or IL-17F, while a heterodimer composed of IL-17RA and IL-17RB is a receptor for IL-17E. Both IL-17B and IL-17E bind to IL-17RB.IL-17A is often referred to as IL-17. It was first mentioned in 1993 (O'Shea J J. et al., Mechanisms underlying lineage commitment and plasticity of helper CD4+ T cells. Science. 2010, 327(5969):1098-1102), As an important pro-inflammatory factor in human peripheral blood, IL-17 plays a key role in combating the pathogenesis of extracellular microorganisms and different autoimmune diseases. In the adaptive immune response, especially in the fight against bacteria and fungi, IL-17A and IL-17F in IL-17 family are core participants (Kolls J K, et al., Interleukin-17 family members and inflammation. Immunity 0.2004, 21(4):467-476). Little is known about the functions of IL-17B, IL-17C and IL-17D. The main functions of IL-17 are to induce the production of chemokines and other cytokines (such as TNF-α), and to attract neutrophils and monocytes at the site of T cell activation. IL-17 can also contribute to the formation of granulocytes by increasing the productions and secretions of granulocyte-macrophage colony stimulating factor (GM-CSF) and its receptor. Further, IL-17 can stimulate neutrophil granulocyte and other cell to produce anti-microbial proteins (AMP) (such as LL37) (Lin A M et al., Mast cells and neutrophils release IL-17 through extracellular trap formation in psoriasis, J. Immunol. 2011, 187(1):490-500). Under different physiological and disease conditions, immunogens are prone to produce Th17 cytokine. Recently, it has been confirmed that various factors can induce the production of IL-17 by other lymphocytes, including $CD8^+\alpha\beta$ T cells, γδ T cells (H. Takatori et al., Lymphoid tissue inducer-like cells are an innate source of IL-17 and IL-22, J. Exp. Med. 2009, 206(1): 35-41), LTi-like natural lymphocytes (ILCs) (NK Crellin et al., Human NKp44bIL-22b cells and LTi-like cells constitute a stable RORCb lineage distinct from conventional natural killer cells, J. Exp. Med. 2010, 207: 281-290), Natural Killer Cells (NK) (M. L. Michel et al., Identification of an IL-17-producing NK1.1(neg) iNKT cell population involved in airway neutrophilia, J. Exp. Med. 2007, 204 (5):995-1001) and human or mouse $CD3^+$ natural killer cells (M. Cella et al., A human natural killer cell subset provides an innate source of IL-22 for mucosal immunity, Nature 0.2009, 457 (7230):722-725). In addition, different innate myeloid immune cells are able to produce IL-17 and localize to barrier tissues such as lung, intestine, skin and peripheral lymph nodes, not only responding quickly to pathogens and allow an immediate response, but also activating and magnifying the adaptive immune response. Intestinal monocytes and macrophages in Crohn's disease and ulcerative colitis, neutrophil granulocytes in systemic vasculitis, mast cells in psoriatic skin lesions, and synovial mast cells in rheumatoid arthritis are good examples thereof.

Whether IL-17 is produced by innate cells or Th17 adaptive cells does not alter the key role of this cytokine in the pathology of psoriasis and psoriatic arthritis (S. P. Raychaudhuri et al., Role of IL-17 in psoriasis and psoriatic arthritis, Clin. Rev. Allergy Immunol. 2013, 44 (2):183-193). Under these conditions, anti-IL-17 drugs are therapeutic. At present, the marketed or developing antibody drugs targeting IL-17 signaling pathway include Brodalumab, Ixekizumab, Secukinumab, ABT-122 (an IL-17 and TNF-α bispecific antibody), CNTO 6785, CJM112, COVA322 (an IL-17 and TNF-α bifunctional antibody), ALX-0761, Bimekizumab and SCH-900117.

Brodalumab is an antibody to the IL-17 receptor, while ixekizumab (a humanized monoclonal antibody) and secukinumab (a fully human monoclonal antibody) are neutralizing antibodies to IL-17A. Secukinumab (Cosentyx) is the first IL-17A monoclonal antibody marketed in the world, achieving a benefit of $1.128 billion in the second year of FDA approval. As Novartis' most marketable drug in recent years, Cosentyx is currently approved for indications including plaque psoriasis, psoriatic arthritis, and ankylosing spondylitis, and is superior to Stelara (IL-12/23 antibody) in maintaining long-term plaque removal, and administering only once a month by patients themselves through injection using a drug prefilled syringe. It has been approved in more than 70 countries and more than 100,000 patients over the world have benefited. Cosentyx will become the new standard treatment for psoriasis. Stelara (ustekinumab, anti-IL-12/23) from Johnson & Johnson is a clinical standard treatment for psoriasis, hits a record up to $3.232 billion in sales in 2016. In March 2016, the FDA approved ixekizumab (Taltz) injection for the treatment of adult patients with moderate to severe plaque psoriasis. Ixekizumab is superior to Amgen's blockbuster anti-inflammatory drug Enbrel (generic name: etanercept) and placebo in all indicators of skin lesion regression, with the data being statistically significant. For psoriasis patients, IL-17A plays an important role in driving the excessive proliferation and activation of keratinocytes (as skin cells). Ixekizumab does not bind to the cytokines of IL-17B, IL-17C, IL-17D, IL-17E or IL-17F.

Clinical studies have found brodalumab has no clinical benefit in the test group of rheumatoid arthritis, and ixekizumab and secukinumab are not as effective in treating rheumatoid arthritis as that of TNF-α (Kalden J R: Emerging Therapies for Rheumatoid Arthritis. Rheumatol Ther (2016) 3:31-42). In vitro experiments have confirmed that the combination of IL-17 inhibitor and TNF-α inhibitor inhibits the release of chemokines, lymphokines and enzymes better than IL-17 inhibitor or TNF-α inhibitor is used alone. In a mouse model of rheumatoid arthritis, a bispecific antibody against IL-17 and TNF-α can inhibit the occurrence of inflammation, and the destruction of bone and connective tissue in mice better than anti-IL-17 or anti-TNF-α is used alone (Fischer J A, Hueber A J, Wilson S. et al., Combined inhibition of tumor necrosis factor a and interleukin-17 as a therapeutic opportunity in rheumatoid arthritis: development and characterization of a novel bispecific antibody. Arthritis Rheumatol. 2015; 67(1):51-62).

If IL-17 inhibitor and TNF-α inhibitor are administered at the same time, the two separate products need to be prepared separately; then, for example, the two products are injected separately. Of course, a single injection of a co-formulation comprising the two products is feasible. Although the dosage and timing can be flexibly selected when the injections are divided, it is inconvenient for patients due to pain and economic reasons. Co-formulations also have the flexibility to choose the dose to a certain extent, but due to the different molecular characteristics of two different products, the discovery of formulation conditions that allow chemical and physical stabilities of the two products is quite challenging, or simply impossible. In addition, co-administration or co-formulation involves the additive costs from the two different drug therapies, which will increase the costs to patient and/or payer, while a formulation of single component (e.g., a bispecific antibody or a fusion protein) allows for optimizing the price and the administration.

Further, in the preparation process of a drug (for example, a monoclonal antibody drug), the "disposable production process" is now often used to achieve aseptic fluid delivery between pharmaceutical equipments in different rooms, to separate equipments satisfying different rooms and different clean requirements; to reduce the risk of environmental pollution of related equipments effectively; and to save costs, time, related manpower and resources. However, such a "disposable production process" system is expensive. Therefore, compared to the preparation of one drug (for example, a bispecific antibody or a fusion protein), the increase in costs of preparing two drugs separately, for example, IL-17 inhibitor and TNF-α inhibitor, is substantial.

Under the circumstances, the production of bispecific antibodies has become a trend. However, there are many limitations in the production of bispecific antibodies. For example, nearly 10-20% of bispecific antibodies originally obtained by Genentech using heterodimerization Knobs-into-Holes technology are unwanted homodimers; the bispecific antibody Abbott produces through the dual-variable domains Ig (DVD-Ig) technology has an internal variable domain with the affinity for binding a antigen being reduced by nearly 10-fold; and interfering with another variable domain when binding different antigens; and has a larger molecular weight of nearly 200 Kd. A bispecific antibody is produced by EpimAb's FIT-Ig technology with a molecular weight of 250 Kd, which can hardly penetrate into hypertonic tissues, thus at least half of the expressed proteins form useless Fab structures; requires three antibody fragments to assemble, which severely affects the expression level of a bispecific antibody. Therefore it is not easy to obtain a bispecific antibody of interest in the art.

Some attempts have been made in the art to produce fusion proteins. An attempt related to the present invention is a Chinese invention patent CN 104311670 B. This patent relates to an IL-17scfv/sTNFR1 fusion protein. Since the antibody structure used therein is IL-17scfv, the affinity of such a fusion protein to IL-17 is low, which is only a tenth of conventional anti-IL-17 antibodies. Meanwhile, the TNF-α inhibitor used therein is TNFR1, having an affinity for TNF-α much lower than that of TNFR2. Therefore, if the IL-17scfv/sTNFR1 fusion protein in the patent is developed into a product, it can be expected that the therapeutic effect of said fusion protein is lower, which will necessarily increase the administration dosage (for example, increase by about 10 times), resulting in significant side effects.

Therefore, as far as the field of the present invention is concerned, there still exists a need for a fusion protein with high specificity that neutralizes both human TNF-α and human IL-17, and it is also expected that such a fusion protein is thermally stable, physically stable, low aggregation, and can neutralize human TNF-α and human IL-17 with high affinity, thereby avoiding the problem of finding suitable formulation conditions to meet the different molecular characteristics of the two molecules).

The present invention thus seeks to solve one or more of the above problems, to obtain a group of new fusion proteins of anti-IL-17 and TNF-α receptor, and to improve the current treatment of autoimmune diseases. However, when constructing the fusion protein of the present invention, the inventors encountered a series of challenges related to chemical stability and physical stability, and required many new improvements, including stabilizing the VH/VL interface of the variable regions in antibodies, increasing heat stability, reducing aggregation, rebalancing the electrostatic distribution in the binding surface of the fusion protein, and maintaining binding affinity for both targets.

To this end, the inventors have fully analyzed the characteristics of the interaction between TNFR and TNF-α when anti-IL-17 occurs in a molecule, with the aids of some recent research results such as bioinformatics, and developed a group of fusion proteins of anti-IL-17 and TNFR. The structure of the fusion protein fully guarantees the proper physical space distance between the bindings of its targets, i.e., after the fusion protein having this structure specifically binds to one target molecule, it does not affect the specific binding to another target molecule. This means the fusion protein of the present invention can have high affinity for IL-17 and TNF-α, respectively, thus inhibit the biological functions of IL-17 and TNF-α, having the potential to treat autoimmune diseases such as rheumatoid arthritis, ankylosing spondylitis, psoriasis and ulcerative colitis. At the same time, the production process of the fusion protein of the present invention is convenient, simple, and low in manufacturing cost, but the affinities of the obtained fusion protein are very high, consistent with the affinity of anti-IL-17 antibody alone for IL-17, and the affinity of TNFR alone for TNF. Consequently, the activities of IL-17 and/or TNF-α can be sufficiently inhibited. That is, the fusion protein of the present invention can realize the preparation of a single active ingredient with low time and money costs, and when used in the field of medicine, it saves the exploration of formulation conditions and is convenient to administration.

Compared with the preparations of both proteins of anti-IL-17 antibody and TNFR respectively, the preparation cost of the fusion protein of the present invention can be reduced by at least half, and the costs of storage, transportation, etc. can be correspondingly reduced; at the same time, when used for individual administration, it only requires to administer a single drug, which makes administration easier.

The fusion protein of the present invention is more potent than the IL-17scfv/sTNFRI fusion protein prepared in CN 104311670 B (even if it indeed has activity), with a dosage of at most about 1/10 of the IL-17scfv/sTNFRI fusion protein, and a significantly reduced potential side effects.

SUMMARY OF THE INVENTION

The present invention discloses a new fusion protein targeting IL-17 and TNF-α, a polynucleotide encoding the fusion protein, a vector containing the polynucleotide, a host cell containing the polynucleotide or the vector, and the use of the double-targeting fusion protein in the treatment, prevention and/or diagnosis of diseases related to the activities of IL-17 and TNF-α in an individual.

The structure of the fusion protein designed by the inventors fully guarantees the proper physical steric distance to its targets. The specific binding of the fusion protein having this structure to one target molecule does not affect the specific binding of said fusion protein to another target molecule.

In one aspect, the present invention provides a fusion protein comprising an anti-human IL-17 antibody or fragment thereof and a moiety that binds TNF-α, capable of inhibiting the binding of IL-17 to its receptor, and preventing TNF-α from exerting its biological functions.

In a preferred embodiment, the present invention provides a fusion protein comprising an anti-human IL-17 antibody or fragment thereof and a moiety that binds TNF-α.

In a further preferred embodiment, the present invention provides a fusion protein comprising an anti-human IL-17 antibody or antigen binding fragment thereof and a moiety that binds TNF-α.

In some embodiments, the anti-IL-17 antibody in the fusion protein of the present invention can be any anti-IL-17 antibody, provided that it can inhibit or reduce the binding of IL-17 to its ligand, including anti-IL-17 antibodies known in the prior art and to be developed in the future.

In some embodiments, the anti-IL-17 antibody in the fusion protein of the present invention also encompasses variants of an anti-IL-17 antibody, an antibody that competes with any anti-IL-17 antibody of the present invention for binding to IL-17, and an antibody binding the same epitope of IL-17 as that of the anti-IL-17 antibody of the invention.

In some embodiments, the moiety in the fusion protein of the present invention that binds TNF-α is TNFR, and the TNFR may be TNFR1 or TNFR2.

In a preferred embodiment, the anti-IL-17 antibody is combined with any of TNFR1 or TNFR2 to form the fusion protein of the present invention.

In a further preferred embodiment, the anti-IL-17 antibody is combined with TNFR2 to form the fusion protein of the present invention, as the affinity of TNFR2 for TNF-α is 10 times that of TNFR1.

In one aspect, the present invention relates to a fusion protein of anti-IL-17 antibody and TNFR, capable of inhibiting the biological functions of IL-17 and TNF-α, which comprises (i) an antigen binding fragment derived from an anti-IL-17 antibody; (ii) immunoglobulin constant region domain; and (iii) TNFR extracellular region.

In a preferred embodiment, the anti-IL-17 antibody in the fusion protein of the present invention is an anti-human IL-17 antibody.

In a preferred embodiment, the anti-IL-17 antibody in the fusion protein of the present invention is an IgG class antibody, preferably an IgG1 subclass, IgG2 subclass, IgG4 subclass antibody.

In a preferred embodiment, in the fusion protein of the present invention, the IgG1 subclass anti-IL-17 antibody has an amino acid sequence of the heavy chain constant region shown as SEQ ID NO: 19; the IgG2 subclass anti-IL-17 antibody has an amino acid sequence of the heavy chain constant region shown as SEQ ID NO: 20; and the IgG4 subclass anti-IL-17 antibody has an amino acid sequence of the heavy chain constant region shown as SEQ ID NO: 21.

In a preferred embodiment, the anti-IL-17 antibody in the fusion protein of the present invention is IgG4 subclass. To prevent the occurrence of arm-exchange, the S228 position (according to Kabat numbering scheme) in the Fc domain has an amino acid substitution, preferably S228P.

In some embodiments, the light chain of the anti-IL-17 antibody in the fusion protein of the present invention is K type or k type, preferably K type.

In a preferred embodiment, in the fusion protein of the present invention, the amino acid sequence of the antibody light chain constant region of K type is shown as SEQ ID NO: 17; of k type is shown as SEQ ID NO: 18.

In some embodiments, in the fusion protein of the present invention, (i) is an antigen binding fragment derived from a human anti-IL-17 antibody.

In some embodiments, in the fusion protein of the present invention, (i) is Fab, Fab', F(ab)₂, F(ab')₂, Fv, single-chain Fv derived from an anti-IL-17 antibody; preferably from a human anti-IL-17 antibody.

In a preferred embodiment, in the fusion protein of the present invention, (i) as an antigen binding fragment derived from an anti-IL-17 antibody has the ability to bind IL-17.

In a further preferred embodiment, in the fusion protein of the present invention, (i) as an antigen binding fragment derived from an anti-IL-17 antibody comprises one to three of the three heavy chain CDRs and one to three of the three light chain CDRs comprised in the paired heavy chain variable region sequence/light chain variable region sequence selected from the group consisting of SEQ ID NOs: 1/2, 3/4, 5/6, 7/8, 9/10, 11/12, 13/14, and 15/16.

In a further preferred embodiment, in the fusion protein of the present invention, (i) as an antigen binding fragment derived from an anti-IL-17 antibody comprises one to three of the three heavy chain CDRs and one to three of the three light chain CDRs comprised in the paired heavy chain variable region sequence/light chain variable region sequence shown as SEQ ID NOs: 1/2, or 7/8.

In a further preferred embodiment, in the fusion protein of the present invention, (i) as an antigen binding fragment derived from an anti-IL-17 antibody comprises one to three of the three heavy chain CDRs and one to three of the three light chain CDRs comprised in the paired heavy chain variable region sequence/light chain variable region sequence having at least 90%, 91%, 92%, 93%, 94%, 95%, 96%, 97%, 98%, 99% or higher sequence identity with the paired heavy chain variable region sequence/light chain variable region sequence shown as SEQ ID NOs: 1/2, 3/4, 5/6, 7/8, 9/10, 11/12, 13/14, or 15/16.

In a further preferred embodiment, in the fusion protein of the present invention, (i) as an antigen binding fragment derived from an anti-IL-17 antibody comprises one to three of the three heavy chain CDRs and one to three of the three light chain CDRs comprised in the paired heavy chain variable region sequence/light chain variable region sequence having one or more (preferably no more than 5) amino acid residue substitutions, deletions or insertions of SEQ ID NOs: 1/2, 3/4, 5/6, 7/8, 9/10, 11/12, 13/14, or 15/16. Preferably, the amino acid substitutions of no more than 5 amino acids are substitutions of no more than 5 conservative amino acids.

In a further preferred embodiment, in the fusion protein of the present invention, (i) as an antigen binding fragment derived from an anti-IL-17 antibody comprises one to three of the three heavy chain CDRs and one to three of the three light chain CDRs comprised in the paired heavy chain variable region sequence/light chain variable region sequence having at least 90%, 91%, 92%, 93%, 94%, 95%, 96%, 97%, 98%, 99% or higher sequence identity with the paired heavy chain variable region sequence/light chain variable region sequence shown as SEQ ID NOs: 1/2, or 7/8.

In a further preferred embodiment, in the fusion protein of the present invention, (i) as an antigen binding fragment derived from an anti-IL-17 antibody comprises one to three of the three heavy chain CDRs and one to three of the three light chain CDRs comprised in the paired heavy chain variable region sequence/light chain variable region sequence having one or more (preferably no more than 5) amino acid residue substitutions, deletions or insertions of SEQ ID NOs: 1/2, or 7/8. Preferably, the amino acid substitutions of no more than 5 amino acids are substitutions of no more than 5 conservative amino acids.

In a further preferred embodiment, in the fusion protein of the present invention, (i) as an antigen binding fragment derived from an anti-IL-17 antibody comprises a paired heavy chain variable region sequence/light chain variable region sequence selected from the group consisting of SEQ ID NOs: 1/2, 3/4, 5/6, 7/8, 9/10, 11/12, 13/14, and 15/16.

In a further preferred embodiment, in the fusion protein of the present invention, (i) as an antigen binding fragment derived from an anti-IL-17 antibody comprises a paired heavy chain variable region sequence/light chain variable region sequence selected from the group consisting of SEQ ID NOs: 1/2, and 7/8.

In a further preferred embodiment, in the fusion protein of the present invention, (i) as an antigen binding fragment derived from an anti-IL-17 antibody comprises a paired heavy chain variable region sequence/light chain variable region sequence having at least 90%, 91%, 92%, 93%, 94%, 95%, 96%, 97%, 98%, 99% or higher sequence identity with the paired heavy chain variable region sequence/light chain variable region sequence selected from the group consisting of SEQ ID NOs: 1/2, 3/4, 5/6, 7/8, 9/10, 11/12, 13/14, and 15/16.

In a further preferred embodiment, in the fusion protein of the present invention, (i) as an antigen binding fragment derived from an anti-IL-17 antibody comprises a paired heavy chain variable region sequence/light chain variable region sequence having one or more (preferably no more than 5) amino acid residue substitutions, deletions or insertions of the paired heavy chain variable region sequence/light chain variable region sequence selected from the group consisting of SEQ ID NOs: 1/2, 3/4, 5/6, 7/8, 9/10, 11/12, 13/14, and 15/16. Preferably, the amino acid substitutions of no more than 5 amino acids are substitutions of no more than 5 conservative amino acids.

In a further preferred embodiment, in the fusion protein of the present invention, (i) as an antigen binding fragment derived from an anti-IL-17 antibody comprises a paired heavy chain variable region sequence/light chain variable region sequence having at least 90%, 91%, 92%, 93%, 94%, 95%, 96%, 97%, 98%, 99% or higher sequence identity with the paired heavy chain variable region sequence/light chain variable region sequence of SEQ ID NOs: 1/2 or 7/8.

In a further preferred embodiment, in the fusion protein of the present invention, (i) as an antigen binding fragment derived from an anti-IL-17 antibody comprises a paired heavy chain variable region sequence/light chain variable region sequence having one or more (preferably no more than 5) amino acid residue substitutions, deletions or insertions of the paired heavy chain variable region sequence/light chain variable region sequence of SEQ ID NOs: 1/2, or 7/8. Preferably, the amino acid substitutions of no more than 5 amino acids are substitutions of no more than 5 conservative amino acids.

In a further preferred embodiment, in the fusion protein of the present invention, (i) as an antigen binding fragment derived from an anti-IL-17 antibody comprises one to three heavy chain CDRs and one to three of light chain CDRs contained in the three heavy chain CDRs and three light chain CDRs comprised in the paired first subunit/second subunit sequences selected from the group consisting of SEQ ID NOs: 60/62, 64/66, 68/70, and 74/72.

In a preferred embodiment, in the fusion protein of the present invention, (i) as an antigen binding fragment derived from an anti-IL-17 antibody comprises one to three heavy chain CDRs and one to three of light chain CDRs contained in the three heavy chain CDRs and three light chain CDRs comprised in the paired first subunit/second subunit sequences having at least 90%, 91%, 92%, 93%, 94%, 95%, 96%, 97%, 98%, 99% or higher sequence identity with the paired first subunit/second subunit sequences.

In a preferred embodiment, in the fusion protein of the present invention, (i) as an antigen binding fragment derived from an anti-IL-17 antibody comprises one to three heavy chain CDRs and one to three of light chain CDRs contained in the three heavy chain CDRs and three light chain CDRs comprised in the paired first subunit/second subunit sequences having one or more (preferably no more than 5) amino acid residue substitutions, deletions or insertions of the paired first subunit/second subunit sequences selected from the group consisting of SEQ ID NOs: 60/62, 64/66, 68/70, and 74/72. Preferably, the amino acid substitutions of no more than 5 amino acids are substitutions of no more than 5 conservative amino acids.

In a preferred embodiment, in the fusion protein of the present invention, (i) as an antigen binding fragment derived from an anti-IL-17 antibody comprises a paired heavy chain variable region sequence/light chain variable region sequence comprised in the paired first subunit/second subunit sequences selected from the group consisting of SEQ ID NOs: 60/62, 64/66, 68/70, and 74/72.

In a preferred embodiment, in the fusion protein of the present invention, (i) as an antigen binding fragment derived from an anti-IL-17 antibody comprises a paired heavy chain variable region sequence/light chain variable region sequence comprised in the paired first subunit/second subunit sequences having at least 90%, 91%, 92%, 93%, 94%, 95%, 96%, 97%, 98%, 99% or higher sequence identity with the paired first subunit/second subunit sequences selected from the group consisting of SEQ ID NOs: 60/62, 64/66, 68/70, and 74/72.

In a preferred embodiment, in the fusion protein of the present invention, (i) as an antigen binding fragment derived from an anti-IL-17 antibody comprises a paired heavy chain variable region sequence/light chain variable region sequence comprised in the paired first subunit/second subunit sequences having one or more (preferably no more than 5) amino acid residue substitutions, deletions or insertions of the paired first subunit/second subunit sequences selected from the group consisting of SEQ ID NOs: 60/62, 64/66, 68/70, and 74/72. Preferably, the amino acid substitutions of no more than 5 amino acids are substitutions of no more than 5 conservative amino acids.

In a preferred embodiment, in the fusion protein of the present invention, (ii) immunoglobulin constant region domain may be the constant region domain of any immunoglobulin, in particular, (ii) is the constant region domain of human immunoglobulin.

In a preferred embodiment, in the fusion protein of the present invention, (ii) immunoglobulin constant region domain may be the Fc domain of any immunoglobulin, in particular, (ii) is the Fc domain of human immunoglobulin.

In a preferred embodiment, in the fusion protein of the present invention, (ii) the immunoglobulin heavy chain constant region domain is the Fc domain of an IgG class antibody, particularly, the Fc domain of an IgG1 subclass, IgG2 subclass, or IgG4 subclass antibody, and more particularly, the amino acid sequence of the Fc domain in the heavy chain constant region of the IgG1 subclass anti-IL-17 antibody is shown in SEQ ID NO: 75; the amino acid sequence of the Fc domain in the heavy chain constant region of the IgG2 subclass anti-IL-17 antibody is shown in SEQ ID NO: 76; the amino acid sequence of the Fc domain in the heavy chain constant region of the IgG4 subclass anti-IL-17 antibody is shown in SEQ ID NO: 77.

In a preferred embodiment, in the fusion protein of the present invention, (ii) the immunoglobulin Fc domain is the Fc domain of a human IgG4 subclass antibody, which comprises an amino acid substitution at position S228 in the Fc region (S228 is the amino acid residue number of the heavy chain constant region according to Kabat database), particularly amino acid substitution S228P.

In a preferred embodiment, in the fusion protein of the present invention, (ii) immunoglobulin constant region domain comprises a constant region domain shown in SEQ ID NOs: 19, 20 or 21; Fc domain (CH2-CH3) shown in SEQ ID NOs: 75, 76 or 77; a constant region domain having at least 90%, 91%, 92%, 93%, 94%, 95%, 96%, 97%, 98%, 99% or higher sequence identity with SEQ ID NOs: 19, 20 or 21; or Fc domain having at least 90%, 91%, 92%, 93%, 94%, 95%, 96%, 97%, 98%, 99% or higher sequence identity with SEQ ID NOs: 75, 76 or 77.

In a preferred embodiment, in the fusion protein of the present invention, (ii) immunoglobulin constant region domain comprises a constant region domain having one or more (preferably no more than 5) amino acid substitutions, deletions or insertions of the constant region domain (CH1-CH2-CH3) shown in SEQ ID NOs: 19, 20 or 21. Preferably, the amino acid substitutions of no more than 5 amino acids are substitutions of no more than 5 conservative amino acids;

or comprises Fc domain having one or more (preferably no more than 5) amino acid substitutions, deletions or insertions of Fc domain (CH2-CH3) shown in SEQ ID NOs: 75, 76 or 77. Preferably, the amino acid substitutions of no more than 5 amino acids are substitutions of no more than 5 conservative amino acids.

In a preferred embodiment, in the fusion protein of the present invention, (iii) TNFR extracellular region is the complete extracellular region of TNF receptor (TNFR) or a part thereof.

In a preferred embodiment, in the fusion protein of the present invention, (iii) TNFR extracellular region is the complete extracellular region of TNFR1 or TNFR2, or a part thereof, preferably, the complete extracellular region of TNFR2, or a part thereof.

In a preferred embodiment, in the fusion protein of the present invention, (iii) TNFR extracellular region is the complete extracellular region of human TNFR1 or human TNFR2, or a part thereof, preferably, the complete extracellular region of human TNFR2, or a part thereof.

In a preferred embodiment, in the fusion protein of the present invention, (iii) TNFR extracellular region is the complete extracellular region of TNFR, consisting of 4 functional domains (CRD1-CRD4) containing 6 cysteine; a part of the TNFR extracellular region may be CRD1-CRD4; or a combination of one or more of CRD1, CRD2, CRD3, and CRD4; preferably a fragment of CRD1-CRD2-CRD3-CRD4.

In a preferred embodiment, in the fusion protein of the present invention, (iii) the extracellular region of TNFR comprises an amino acid sequence shown in SEQ ID NOs: 22, 23, 24 or 25.

In a preferred embodiment, in the fusion protein of the present invention, (iii) the extracellular region of TNFR comprises an amino acid sequence having at least 90%, 91%, 92%, 93%, 94%, 95%, 96%, 97%, 98%, 99% or higher sequence identity with the amino acid sequence shown in SEQ ID NO: 22, 23, 24 or 25.

In a preferred embodiment, in the fusion protein of the present invention, (iii) the extracellular region of TNFR comprises an amino acid sequence having one or more (preferably no more than 5) amino acid substitutions, deletions or insertions of the amino acid sequences shown in SEQ ID NOs: 22, 23, 24 or 25. Preferably, the amino acid substitutions of no more than 5 amino acids are substitutions of no more than 5 conservative amino acids.

The above anti-IL-17 antibodies and their variants have substantially the same biological functions as those of anti-IL-17 antibodies; the above-mentioned fragments derived from anti-IL-17 antibodies, antigen-binding fragments and their variants all have substantially the same antigen binding capacity as those of anti-IL-17 antibodies; immunoglobulin Fc domain and its variants have substantially the same biological functions as those of immunoglobulin Fc domain; TNFR extracellular domain, its fragments and variants have substantially the same biological functions as those of TNFR.

In some embodiments, the fusion protein of the present invention further comprises a linker peptide between (i), (ii) and/or (iii). The linker peptide preferably comprises one or more amino acids, more preferably at least 5 amino acids, most preferably a linker peptide selected from the group consisting of SEQ ID NO: 30-58.

In some embodiments, the fusion protein of the present invention is operatively linked from N-terminal to C-terminal in the order of (i), (ii) and (iii); in the order of (iii), (i) and (ii); or in the order of (iii), (ii) and (i).

In a preferred embodiment, the fusion protein of the present invention is operatively linked from N-terminal to C-terminal in the order of (i), (ii) and (iii). Preferably, the C-terminus of the heavy chain part in (i) is operatively linked to the N-terminus of (ii); or the C-terminus of the light chain part in (i) is operatively linked to the N-terminus of (ii).

In a preferred embodiment, the fusion protein of the present invention is operatively linked from N-terminal to C-terminal in the order of (iii), (ii) and (i), Preferably, the C-terminus of (ii) is operatively linked to N-terminus of each of the two heavy chains of (iii); or the C-terminus of (ii) is operatively linked to N-terminus of each of the two light chains of (iii).

In a preferred embodiment, the anti-IL-17 antibody can be at N-terminus of the fusion protein of the present invention, meanwhile the extracellular functional region of TNFR is linked to C-terminus of the anti-IL-17 antibody heavy chain via a linker peptide; or the N-terminus of the fusion protein of the present invention is TNFR-Fc fusion, with its C-terminus linking to anti-IL-17 antibody Fab in either of the following ways: with its C-terminus linking to the heavy chain part of anti-IL-17 antibody Fab, wherein the free light chain part of the anti-IL-17 antibody Fab binds to Fab heavy chain part via disulfide bond; or with its C-terminus linking to the light chain part of anti-IL-17 antibody Fab, wherein the free heavy chain part of the anti-IL-17 antibody Fab binds to Fab light chain part via disulfide bond.

In a preferred embodiment, the fusion protein of the present invention comprises the first subunit of SEQ ID NO: 60 and the second subunit of SEQ ID NO: 62, hereinafter also referred to as BY19.3 fusion protein, which from N-terminus to C-terminus comprises a human anti-IL-17 antibody (IgG4, K, S228P), and an extracellular region (CRD1-CRD2-CRD3-CRD4) of human TNFR2 operatively linked to the C-terminus of the human anti-IL-17 antibody heavy chain through a linker peptide.

In a preferred embodiment, the fusion protein of the present invention comprises the first subunit of SEQ ID NO: 64 and the second subunit of SEQ ID NO: 66, hereinafter also referred to as BY19.5 fusion protein, which from N-terminus to C-terminus comprises a human anti-IL-17 antibody (IgG4, K, S228P), and a complete human TNFR2 extracellular region operatively linked to the C-terminus of the human anti-IL-17 antibody heavy chain through a linker peptide.

In a preferred embodiment, the fusion protein of the present invention comprises the first subunit of SEQ ID NO: 68 and the second subunit of SEQ ID NO: 70, hereinafter also referred to as BY19.6 fusion protein, which from N-terminus to C-terminus comprises an extracellular region part (a fragment of CRD1-CRD2-CRD3-CRD4) of human TNFR2, Fc(CH2-CH3 direction) with its N-terminus linked to C-terminus of the extracellular region part, and human anti-IL-17 antibody (IgG4, K, S228P) Fab with its heavy chain part operatively linked to C-terminus of Fc, and the free light chain part of the Fab binding (pair, match) to Fab heavy chain part via disulfide bond.

In a preferred embodiment, the fusion protein of the present invention comprises the first subunit of SEQ ID NO: 74 and the second subunit of SEQ ID NO: 72, hereinafter also referred to as BY19.7 fusion protein, which from N-terminus to C-terminus comprises an extracellular region part (a fragment of CRD1-CRD2-CRD3-CRD4) of human TNFR2, Fc with its N-terminus linked to C-terminus of the extracellular region part, and human anti-IL-17 antibody (IgG4, K, S228P) Fab with its heavy chain part operatively linked to C-terminus of Fc, and the free heavy chain part of the Fab binding (pair, match) to Fab light chain part via disulfide bond.

In one aspect, the invention relates to a polynucleotide encoding the fusion protein of the invention.

In some embodiments, the present invention provides polynucleotides encoding the fusion protein of the present invention, vectors comprising the polynucleotides encoding the fusion protein of the present invention. The vectors preferably are expression vectors, most preferably glutamine synthetase expression vectors with dual expression cassettes.

In another aspect, the invention relates to a vector comprising the above polynucleotide.

In another aspect, the present invention relates to a host cell comprising the above polynucleotide or vector.

In some embodiments, the host cell is a CHO, HEK293, or NS0 cell.

In another aspect, the invention relates to a method for producing the fusion protein of the invention, comprising the steps of (i) cultivating the above-mentioned host cell under conditions suitable for expressing the fusion protein of the invention, and (ii) recovering the fusion protein.

In another aspect, the invention relates to a method for alleviating, retarding, inhibiting or preventing a disease or a disorder by eliminating, inhibiting or reducing IL-17 activity.

In another aspect, the method of the invention also relates to a method for treating an autoimmune disease by combination therapy, which method comprises administering to an individual an effective amount of any fusion protein herein and one or more other drugs.

In some embodiments, the individual is a mammal, preferably a human.

In another aspect, the invention relates to a pharmaceutical composition comprising the fusion protein of the invention and a pharmaceutically acceptable carrier.

In some embodiments, the present invention provides a diagnostic kit or a pharmaceutical composition comprising the fusion protein of the present invention.

In another aspect, the present invention relates to a use of the fusion protein of the present invention and a use of the aforementioned pharmaceutical composition for the preparation of a medicament for treating or preventing diseases related to the activities of IL-17 and TNF-α in an individual.

In some embodiments, the present invention provides a diagnostic kit or pharmaceutical composition comprising the fusion protein of the present invention, which is useful for treating or preventing autoimmune diseases in an individual.

In a preferred embodiment, the present invention provides a diagnostic kit or pharmaceutical composition comprising the fusion protein of the present invention, which is useful for treating or preventing rheumatoid arthritis, ankylosing spondylitis, psoriasis and ulcerative colitis.

In a preferred embodiment, the present invention provides a diagnostic kit or pharmaceutical composition comprising the fusion protein of the present invention, which is useful for treating or preventing psoriasis in an individual; wherein the individual is preferably a mammal, more preferably a human. The invention also encompasses any combination of any of the embodiments herein. Any embodiment herein or any combination thereof is suitable for the preparation method and use of any anti-IL-17 antibody or fragment thereof and TNFR fusion protein of the present invention.

DESCRIPTION OF THE DRAWINGS

The preferred embodiments of the present invention described in detail below will be better understood when read in combination with the following drawings. For the purpose of illustrating the invention, some preferred embodiments are shown in the figures. However, it should be understood that the present invention is not limited to the embodiments shown in the drawings.

FIG. 1A exemplifies the structural schematic diagram of the fusion protein from the N-terminus to the C-terminus comprising an antigen-binding fragment of an anti-IL-17 antibody, the constant domains of a globulin heavy chain, and TNFR ECD; FIG. 1B exemplifies the structural schematic diagram of the fusion protein from the N-terminus to the C-terminus comprising TNFR ECD, immunoglobulin Fc domain, and an antigen-binding fragment of an anti-IL-17 antibody.

DETAILED DESCRIPTION OF THE INVENTION

Figure 1:
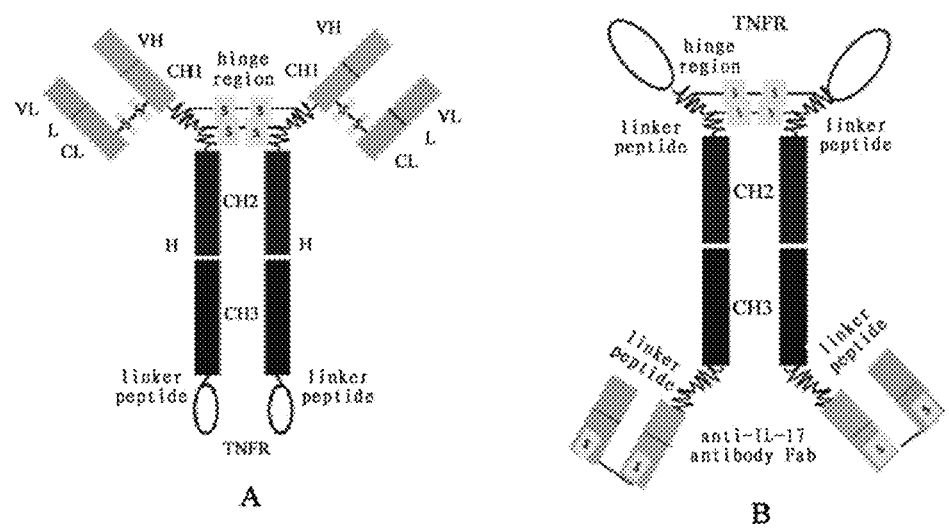
FIGS. 1A and 1B: show the structural schematic diagram of the fusion protein of the present invention targeting IL-17 and TNF-α.

Unless otherwise defined, all terms used herein have the meaning as commonly understood by those skilled in the art to which this invention belongs.

For illustrating the specification, the following definitions for some terms are given, and as appropriate, terms used in the singular also include the plural, and vice versa. It is to be understood that the terms defined herein are only for describing specific embodiments, and not for limiting.

I. Definition

The term "antibody" as used herein is in its broadest sense and covers a variety of antibody structures, including but not limited to monoclonal antibodies, polyclonal antibodies, multispecific antibodies (e.g., bispecific antibodies), and antibody fragments, as long as they show the desired antigen-binding activity.

As used herein, the terms "whole antibody", "full-length antibody", "complete antibody", and "intact antibody" are used interchangeably herein, all refer to one having a structure that is substantially similar to the structure of a naturally occurring antibody.

The term "monoclonal antibody" or "monoclonal antibody composition" as used herein refers to a preparation of antibody molecules having homogeneous amino acid components, and is not limited to the method of production. Monoclonal antibodies or antigen-binding fragments thereof can be produced, for example, by hybridoma technology, recombinant technology, phage display technology, synthetic technology such as CDR grafting, or other techniques known in the art and combinations thereof.

The term "human antibody" as used herein refers to an antibody having an amino acid sequence corresponding to an antibody produced by a human or human cell, or derived from a non-human source that utilizes human antibody repertoires or other human antibody-encoding sequences. This definition of a human antibody specifically excludes a humanized antibody comprising non-human antigen-binding residues.

The antibody may be a complete antibody molecule, or a functional fragment thereof, including but not limited to, for example, an antigen binding portion, Fab, Fab', F(ab)$_2$, F(ab')2, Fv. The constant regions of an antibody can be altered (e.g., mutated) to modify the characteristics of the antibody, for example, one or more of the following characteristics can be increased or decreased: antibody glycosylation, number of cysteine residues, effector function, or complement function. An intact antibody will generally comprises at least two full-length heavy chains and two full-length light chains, but in some cases may comprise fewer chains, for example, antibodies that naturally occur in camels only possess heavy chains.

As used herein, the term "antibody fragment" refers to a molecule that is different from an intact antibody, and possesses a portion of the intact antibody, binding to the antigen to which the intact antibody binds.

As used herein, the term "antigen-binding fragment" of an antibody is a portion or a part of an intact or entire antibody, capable of binding antigen or competing with an intact antibody (i.e., from which the antigen-binding fragment is derived) for antigen binding. Antigen-binding fragments can be prepared by recombinant DNA technology, enzymatic cleavage, or chemical cleavage of intact antibodies. Examples of antibody binding fragments include but are not limited to Fab, Fab', F(ab')$_2$, Fv, single-chain Fv. The Fab fragment is a monovalent fragment consisting of the VL, VH, CL and CH1 domains, and can be obtained for example by papain digestion of a complete antibody. The F(ab')$_2$ fragment is a bivalent fragment as a dimer of Fab', and can be produced by pepsin digesting a complete antibody below the disulfide bond in the hinge region. F(ab')2 can be reduced under neutral conditions by breaking disulfide bonds in the hinge region, and converted to Fab' monomer. Fab' monomer is basically an Fab fragment with a hinge region (for more detailed descriptions of other antibody fragments, see: Fundamental Immunology, edited by W. E. Paul, Raven Press, N.Y. (1993)). an Fv fragment is composed of VL and VH domains of a half-antibody. In addition, although $V_L$ and $V_H$ domains, two domains in Fv fragment, are encoded by separate genes, they can be linked by a synthetic linker that enables the two domains to be produced as a single protein chain through recombinant methods, The $V_L$ and $V_H$ regions in the single protein chain pair to form a single chain Fv. An antigen-binding fragment of an antibody can be obtained by chemical methods, recombinant DNA methods, or protease digestion methods.

The term "antibody heavy chain" as used herein refers to the larger of the two types of polypeptide chains present in an antibody molecule, which normally determines the class of an antibody it derives from.

The term "antibody light chain" as used herein refers to the smaller of the two types of polypeptide chains present in an antibody molecule. K light chain and k light chain refer to the two major antibody light chain isotypes.

Depending on the amino acid sequences of the constant regions of heavy chains, antibodies are divided into "classes" of IgA, IgD, IgE, IgG, and IgM, and several of these classes can be further divided into subclasses, such as IgG1, IgG2, IgG3 and IgG4, IgA1 and IgA2. The heavy chain constant regions that correspond to the different classes of antibodies are called u, 6, F, y, and p, respectively. The light chain constant regions (CL) that can be found in all five antibody classes are called κ and λ. Within the full-length light and heavy chains, the variable region and the constant region are usually linked by a "J" region of about 12 or more amino acids, and the heavy chain also comprises a "D" region of about 10 or more amino acids. See, for example, Fundamental Immunology, Ch. 7 (Paul, W. Editor, Second Edition, Raven Press, N.Y. (1989)) (which is incorporated herein by reference in its entirety for all purposes). The variable regions of each light/heavy chain pair usually form an antigen binding site.

As used herein, the term "variable region" or "variable domain" refers to the domain of an antibody heavy or light chain that participates in the binding of an antibody to an antigen. A heavy chain variable domain (VH) and a light chain variable domain (VL) of a natural antibody usually have similar structures, with each domain comprising four conserved framework regions (FRs) and three complementarity determining regions. (See, e.g. Kindt et al., Kuby Immunology, $6^{th}$ ed., W.H. Freeman and Co., page 91 (2007). A single VH or VL domain may be sufficient to confer antigen-binding specificity The light chain variable region and the heavy chain variable region generally comprise from N- to C-terminus the domains FR1, CDR1, FR2, CDR2, FR3, CDR3, and FR4.

The term "immunoglobulin" as used herein refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each immunoglobulin heavy chain has a variable region (VH), also called a variable heavy domain or a heavy chain variable domain, followed by three constant domains (CH1, CH2, and CH3), also called a heavy chain constant region. Similarly, from N- to C-terminus, each immunoglobulin light chain has a variable region (VL), also called a variable light domain or a light chain variable domain, followed by a constant light (CL) domain, also called "a light chain constant region (domain)".

The term "human immunoglobulin" as used herein is one which possesses an amino acid sequence which corresponds to that of an immunoglobulin produced by a human or a human cell or derived from a non-human source that utilizes human immunoglobulin repertoires or other human immunoglobulin-encoding sequences.

The terms "binding" and "specific binding" as used herein refer to the binding of an antibody or antigen-binding portion to an epitope in an in vitro assay, preferably in bio-optical interferometry (ForteBio) using purified wild-type antigen. In certain embodiments, when the antibody or antigen-binding portion preferably recognizes its target antigen in a complex mixture of proteins and/or macromolecules, the antibody or antigen-binding portion is referred to as capable of specifically binding antigen. The specific binding can be measured by enzyme-linked immunosorbent assay (ELISA) or other techniques familiar to those skilled in the art, such as surface plasmon resonance (SPR) technology (analysis on a BIAcore instrument) (Liljeblad et al., Analysis of agalacto-IgG in rheumatoid arthritis using surface plasmon resonance, Glyco J., 2000, 17, 323-329).

The term "affinity" as used herein refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant ($K_D$), which is the ratio of dissociation and association rate constants ($k_{off}$ and $k_{on}$, respectively). Affinity can be measured by common methods known in the art. A particular method for measuring affinity is Surface Plasmon Resonance (SPR).

When the term "competition" as used herein is used in the case of competing of antigen binding proteins for the same epitope (eg, neutralizing antigen binding protein or neutralizing antibody), it means competition between antigen binding proteins, which is determined by an assay wherein the antigen binding protein to be detected (e.g. antibody or immunologically functional fragment thereof) prevents or inhibits (e.g. reduces) the specific binding of a reference antigen binding protein (e.g. ligand or a reference antibody) to a common antigen (e.g. IL-17 or fragments thereof). Many types of competitive binding assays can be used to determine whether one antigen binding protein competes with another. These assays are, for example, solid phase direct or indirect radioimmunoassay (RIA), solid phase direct or indirect enzyme immunoassay (EIA), sandwich competition assay (see, for example, Stahli et al., 1983, Methods in Enzymology 9: 242-253). Usually when the competitive antigen binding protein is present in excess, it will inhibit (e.g. reduce) at least 40-45%, 45-50%, 50-55%, 55-60%, 60-65%, 65-70%, 70-75% or 75% or more of the specific binding of the reference antigen binding protein to the common antigen. In some cases, binding is inhibited by at least 80-85%, 85-90%, 90-95%, 95-97%, or 97% or more.

The term "effector function" as used herein refers to those biological activities that can be attributed to the Fc region of an antibody, and vary with the antibody isotype. Examples of antibody effector functions include: C1q binding, and complement-dependent cytotoxicity (CDC); Fc receptor binding; antibody-dependent cell-mediated cytotoxicity (ADCC); phagocytosis; cell surface receptors (such as B cell receptors) downregulation; and B cell activation.

The term "about" as used herein, when used in combination with a number, is meant to cover a number within a range that has a lower limit that is 5% less than the specified number and an upper limit that is 5% greater than the specified number.

The term "comprise" or "comprising" as used herein means including elements, integers, or steps, but does not exclude any other elements, integers, or steps, and sometimes specifically refers to only the listed elements, integers, or steps.

As used herein, the terms "effective amount" and "therapeutically effective amount" refer to the amount or dose that produces the desired effects in an individual after the antibody or antigen-binding fragment of the present invention is administered in a single or multiple doses. The desired effects include improvement of the individual's condition (eg, improvement of one or more symptoms) and/or delay in the progression of symptoms, etc.

The effective amount can be easily determined by the attending physician as a person skilled in the art by considering the following factors: such as mammal species; its size, age, and general health; the specific disease involved; the degree or severity of the disease; the response from an individual patient; specific antibody administered; mode of administration; bioavailability characteristics of the administered formulation; selected dosing regimen; and use of any concomitant therapy.

As mentioned above, in some cases, the interaction between an antibody and its target antigen can interfere with the function of the target. The required amount of administration further depends on the binding affinity of the antibody for its specific antigen, and also on the clearance rate of the antibody in the individual receiving the administration. As a non-limiting example, the therapeutically effective dose of the fusion protein of the present invention generally ranges from about 0.1 mg/kg body weight to about 100 mg/kg body weight. In some embodiments, the fusion protein of the present invention is administered to an individual at a dose of 0.1 mg/kg, 0.5 mg/kg, 1 mg/kg, 2 mg/kg, 5 mg/kg, 10 mg/kg, 15 mg/kg, 20 mg/kg, 25 mg/kg, 30 mg/kg, 50 mg/kg, 75 mg/kg, 100 mg/kg or higher. Common dosage frequency ranges are, for example, twice a day to once a week, once every two weeks, once every three weeks, once every month, once every two months, once every three months, once every six months.

The term "operably linked to" as used herein means that the specified components are linked in a relationship that allows them to function in an expected manner.

The term "signal sequence" as used herein is an amino acid sequence linked to the N-terminus of a protein, which promotes secretion of the protein outside the cell. The mature form of the extracellular protein has no signal sequence, which is excised during the secretory process.

As used herein, the term "N-terminus" refers to the last amino acid at the N-terminus, and the term "C-terminus" refers to the last amino acid at the C-terminus.

The term "fusion" as used herein refers to the direct connection of two or more components by peptide bonds or the operable connection of two or more components via one or more linker peptides.

The term "host cell" as used herein refers to a cell into which a foreign polynucleotide sequence has been introduced, including the progeny of such cells. Host cells include "transformants", and "transformed cells", which include the primary transformed cells (parent cells), and progeny derived therefrom. Progeny may not be completely identical in nucleic acid content to a parent cell, but may contain mutations. Mutant progeny that have the same function or biological activity as screened or selected for in the originally transformed cell are included herein. Host cells are any type of cell system that can be used to produce the fusion protein of the present invention. Host cells not only include cultured cells, but also include cells within transgenic animals, transgenic plants, or cultured plant tissues or animal tissues.

As used herein, the terms "individual" and "subject" are used interchangeably and refer to a mammal. Mammals include, but are not limited to domesticated animals (eg, cows, sheep, cats, dogs, and horses), primates (eg, humans and non-human primates such as monkeys), rabbits, and rodents (e.g., mice and rats). In particular, the individual is a human.

The term "vector" as used herein refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The term "isolated" antibody as used herein is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., size exclusion chromatography, ion exchange or reverse phase HPLC). For review of methods for assessment of antibody purity, see, e.g., Flatman, S. et al., J. Chrom. B 848: 79-87 (2007).

As used herein, the term "treatment" refers to a clinical intervention that is intended to alter the natural course of the disease in the individual being treated. Desirable therapeutic effects include but are not limited to preventing the occurrence or recurrence of the disease, reducing symptoms, reducing any direct or indirect pathological consequences of the disease, preventing metastasis, reducing the rate of progression of the disease, improving or alleviating the disease state, and relieving or improving the prognosis. In some embodiments, the fusion protein of the present invention is used to delay disease progression or to slow the progression of the disease.

As used herein, the term "autoimmune disease" refers to a disease caused by the body's immune response to its own components, resulting in damage to its own tissues. In the present invention, it particularly refers to rheumatoid arthritis, ankylosing spondylitis, psoriasis and ulcerative colitis The term "variant" as used herein refers to a nucleotide sequence or amino acid sequence derived from a parent nucleotide sequence or amino acid sequence, but the sequence itself is different from the parent sequence. "Variants" include variant sequences that exist in nature, variant sequences obtained through natural processes, and variant sequences obtained through artificial methods.

The term "conservative substitution/replacement" as used herein refers to the substitution/replacement of one amino acid with another amino acid in the same category, for example, the substitution/replacement of one acidic amino acid with another acidic amino acid, and the substitution of one basic amino acid with another basic amino acid/Substitution, or substitution/replacement of a neutral amino acid with another neutral amino acid. Exemplary substitutions are shown in Table A below.

TABLE A

| Original Residue | Exemplary Substitutions | Preferred Substitutions |
| --- | --- | --- |
| Ala (A) | Val; Leu; Ile | Val |
| Arg (R) | Lys; Gin; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |

TABLE A-continued

| Original Residue | Exemplary Substitutions | Preferred Substitutions |
| --- | --- | --- |
| Gly (G) | Ala | Ala |
| His (H) | Asn; Gln; Lys; Arg | Arg |
| Ile (I) | Leu; Val; Met; Ala; Phe; norleucine | Leu |
| Leu (L) | norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; norleucine | Leu |

"Percent (%) amino acid sequence identity" with respect to a reference amino acid sequence is defined as the percentage of amino acid residues in an amino acid sequence that are identical with the amino acid residues in the reference polypeptide sequence, after aligning the sequences and introducing gaps, if necessary, to achieve the maximum percent sequence identity, and not considering any conservative substitutions as part of the sequence identity, calculated as: the number of amino acid residues in the amino acid sequence that is the same as the amino acid residues of the control/reference polypeptide sequence is divided by the total number of amino acid residues to obtain the quotient (expressed as a percentage). Sequence alignment can be performed using various methods in the art to determine percent amino acid sequence identity, for example, using publicly available computer software such as BLAST, BLAST-2, ALIGN, or MEGALIGN (DNASTAR) software. Those skilled in the art can determine appropriate parameters for aligning sequences, including any algorithms needed to achieve maximal alignment over the full length of the sequences being compared.

When referring to percent (%) amino acid sequence identity in this application, it is calculated relative to the full length of the longer sequence unless otherwise specified. The full-length calculation relative to the longer sequence applies to both nucleic acid sequences and polypeptide sequences.

II. Fusion Protein

The term "fusion protein" as used herein refers to a new polypeptide sequence resulting from the linkage of two or more identical or different polypeptide sequences, and in particular refers to a recombinantly obtained sequence, comprising one or more identical or different naturally unlinked polypeptide sequences.

The fusion protein of the present invention binds to IL-17 with a dissociation constant ($K_D$) of $10^{-8}$ M or less, such as $10^{-9}$ M to $10^{-12}$ M; and specifically binds to TNF molecule with a dissociation constant ($K_D$) of $10^{-8}$ M or less, such as $10^{-9}$ M to $10^{-12}$ M.

In the fusion protein of the present invention, the above-mentioned (i), (ii) and/or (iii) are optionally operatively linked via a linker peptide.

II-1. Anti-IL-17 Antibody

An interleukin (IL) is a cytokine. Human IL-17 (CTLA-8, Swiss Prot Q16552) is a proinflammatory cytokine, produced by a subset of memory T cells (called Th17) that participate in the pathogenesis of MS, and can induce epithelial cells, endothelial cells, and fibroblasts to synthesize and secrete IL-6, IL-8, G-CSF, and PGE2, to promote the expression of ICAM-1. IL-17 plays a role in inducing other inflammatory cytokines, chemokines and adhesion molecules. Treatment of animals with IL-17 neutralizing antibodies reduces the incidence and severity of disease in autoimmune encephalomyelitis (Komiyama, Y. et al., J. Immunol., 177 (2006) 566-573). IL-17A is overexpressed in cerebrospinal fluid of MS patients (Hellings, P. W. et al., Am. J. Resp. Cell Mol. Biol., 28 (2003) 42-50; Matusevicius, D. et al., Multiple Sclerosis 5 (1999) 101-104; WO 2005/051422). In addition, IL-17A neutralizing antibodies reduce the severity and morbidity of the mouse collagen-induced arthritis RA model, and high levels of IL-17A can be detected in synovial fluid from inflamed joints of RA patients (Ziolkowska, M. et al., J. Immunol. 164 (2000) 2832-2838; Kotake, S. et al., J. Clin. Invest. 103 (1999) 1345-1352; Hellings, P. W. et al. Am. J. Resp. Cell Mol. Biol. 28 (2003) 42-50).

As used herein, IL-17 refers to any natural IL-17 from any vertebrate source (including mammals such as primates (eg, humans) and rodents (eg, mice and rats)), unless otherwise indicated. The term encompasses "full-length" unprocessed IL-17 as well as any form of IL-17 or any fragment thereof produced by intracellular processing. The term also includes naturally occurring variants of IL-17, for example, splice variants or allelic variants. IL-17 herein is sometimes preferable IL-17A.

As used herein, the terms "anti-IL-17 antibody", "anti-IL-17", "IL-17 antibody" or "IL-17 binding antibody" refer to an antibody that is capable of binding IL-17 or fragments thereof with sufficient affinity, so that the antibody can be used as a diagnostic and/or therapeutic agent targeting IL-17. In one embodiment, the degree to which the anti-IL-17 antibody binds to unrelated, non-IL-17 protein is less than about 10% of the antibody's binding to IL-17, as measured, for example, by radioimmunoassay (RIA). In some embodiments, the anti-IL-17 antibody provided herein has a dissociation constant (Kd)≤1 µM, ≤100 nM, ≤10 nM, ≤1 nM, ≤0.1 nM, ≤0.01 nM, or ≤0.001 nM (e.g. $10^{-8}$ M or less, such as $10^{-8}$ M to $10^{-13}$ M, such as $10^{-9}$ M to $10^{-13}$ M). In some embodiments, the anti-IL-17 antibody is a multi-specific antibody, such as a bispecific antibody.

The IL-17 antibody or antigen-binding fragment of the present invention comprises substitutions, insertions or deletions. In preferred embodiments, the substitution, insertion or deletion occurs in a region outside the CDR (for example in FR). Optionally, the anti-IL-17 antibodies of the invention comprise post-translational modifications to the light chain variable region or heavy chain variable region, to light chain or heavy chain.

The IL-17 antibody provided by the present invention exhibits inhibitory activity, such as inhibiting the expression, activity and/or signaling of IL-17 (such as inhibiting the expression of IL-17 by T cells), or interfering with the interaction of IL-17 and its receptor. The IL-17 antibody provided by the present invention completely or partially reduces or regulates the expression or activity of IL-17 after binding or interacting with IL-17 (such as human IL-17). After the interaction between the antibody and the human IL-17 polypeptide and/or peptide, the reduction or regulation of the biological function of IL-17 is complete, significant or partial. The antibody is considered to be able to completely inhibit the expression or activity of IL-17, in the case that the expression or activity level of IL-17 is reduced by at least 95% (e.g., reduced by 96%, 97%, 98%, 99% or 100%) when the antibody is present, compared to the level of IL-17 expression or activity when there is no interaction (such as binding) with the antibody herein. The IL-17 antibody is considered to be able to significantly inhibit the expression or activity of IL-17, in the case that the expression or activity level of IL-17 is reduced by at least 50% (e.g., reduced by 55%, 60%, 75%, 80%, 85% or 90%) when the IL-17 antibody is present, compared to the level of IL-17 expression or activity when there is no interaction (such as binding) with the antibody herein. The IL-17 antibody is considered to be able to partially inhibit the expression or activity of IL-17, in the case that the expression or activity level of IL-17 is reduced by less than 95% (e.g., reduced by 10%, 20%, 25%, 30%, 40%, 50%, 60%, 75%, 80%, 85% or 90%) when the IL-17 antibody is present, compared to the level of IL-17 expression or activity when there is no interaction (such as binding) with the antibody herein.

If the activity is reduced compared to the activity measured in the absence of the antibody, the antibody "inhibits" the activity induced by or associated with the antigen, such as the activity induced by IL-17. In certain embodiments, the antibody inhibits the activity of the antigen in the presence of the antibody by at least 10% compared to the activity in the absence of the antibody. In some embodiments, the antibody inhibits activity by at least 20%, at least 30%, at least 40%, at least 50%, at least 60%, at least 70%, at least 80%, or at least 90% or 100%. If the activity is reduced by at least 50% in the presence of the antibody compared to the activity in the absence of the antibody, then the antibody is deemed to "neutralize" the antigen or its related activity. In some embodiments, the neutralizing antibody inhibits activity by at least 60%, at least 70%, at least 80%, or at least 90% or 100%. In certain embodiments, the activity induced by IL-17 is cell proliferation in vitro or in vivo. In certain other embodiments, the IL-17-induced activity is IL-17-mediated inflammation or immune-related diseases. In other embodiments, the IL-17-induced activity is IL-17-mediated inflammatory cell infiltration.

In certain embodiments, one or more amino acid modifications may be introduced into the Fc-region of an antibody provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution) at one or more amino acid positions.

In certain embodiments, it may be desirable to create cysteine engineered antibodies, e.g., "thioMAbs," in which one or more residues of an antibody are substituted with cysteine residues.

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof.

Examples of paired heavy chain variable regions (VH) and light chain variable regions (VL) in antigen-binding fragments of anti-IL-17 antibodies comprised in the fusion protein of the present invention are provided in Table IA below.

TABLE 1

Examples of heavy chain variable region and light chain variable region sequences in antigen-binding fragments of anti-IL-17 antibodies comprised in the fusion protein of the present invention

| Variable regions | Amino acid sequences | SEQ ID NO: |
|---|---|---|
| VH | EVQLVESGGGLVQPGGSLRLSCAASGFTFSNYWMNWVRQAPGKG LEWVAAINQDGSEKYYVGSVKGRFTISRDNAKNSLYLQMNSLRVE DTAVYYCVRDYYDILTDYYIHYWYFDLWGRG | 1 |
| VL | EIVLTQSPGTLSLSPGERATLSCRASQSVSSSYLAWYQQKPGQAPRL LIYGASSRATGIPDRFSGSGSGTDFTLTISRLEPEDFAVYYCQQYGSS PCTFGQG | 2 |
| VH | EVQLVESGGGLVQPGRSLRLSCAASGFTFDDYAMHWVRQAPGKG LEWVSGINWSSGGIGYADSVKGRFTISRDNAKNSLYLQMNSLRAED TALYYCARDIGGFGEFYWNFGLWGRG | 3 |
| VL | EIVLTQSPATLSLSPGERATLSCRASQSVRSYLAWYQQKPGQAPRLL IYDASNRATGIPARFSGSGSGTDFTLTISSLEPEDFAVYYCQQRSNW PPATFGGG | 4 |
| VH | EVQLVESGGGLVQPGGSLRLSCAASGFTFSDYNMAWVRQAPGKGL EWVATITYEGRNTYYRDSVKGRFTISRDNAKNSLYLQMNSLRAED TAVYYCASPPQYYEGSIYRLWFAHWGQG | 5 |
| VL | AIQLTQSPSSLSASVGDRVTITCRADESVRTLMHWYQQKPGKAPKL LIYLVSNSEIGVPDRFSGSGSGTDFRLTISSLQPEDFATYYCQQTWSD PWTFGQG | 6 |
| VH | QVQLVQSGAEVKKPGSSVKVSCKASGYSFTDYHIHWVRQAPGQGL EWMGVINPMYGTTDYNQRFKGRVTITADESTSTAYMELSSLRSEDT AVYYCARYDYFTGTGVYWGQG | 7 |

TABLE 1-continued

Examples of heavy chain variable region and light chain variable region sequences in antigen-binding fragments of anti-IL-17 antibodies comprised in the fusion protein of the present invention

| Variable regions | Amino acid sequences | SEQ ID NO: |
|---|---|---|
| VL | DIVMTQTPLSLSVTPGQPASISCRSSRSLVHSRGNTYLHWYLQKPGQ SPQLLIYKVSNRFIGVPDRFSGSGSGTDFTLKISRVEAEDVGVYYCS QSTHLPFTFGQG | 8 |
| VH | EVQLVESGGGLVQPGGSLRLSCAASGFTFSDYTMLWVRQAPGKGL EWVAIIKSGGSYSYYPDSVKGRFTISRDNAKNSLYLQMNSLRAEDT AVYYCARDGDYGSSYGAMDYWGQG | 9 |
| VL | DIQMTQSPSSLSASVGDRVTITCRASQDINSYLSWFQQKPGKAPKSL IVRANRLVDGVPSRFSGSGSGQDYSLTISSLQPEDFATYYCLQYDAF PPYTFGQG | 10 |
| VH | EVQLVQSGAEVKKPGSSVKVSCKASGGSFGGYGIGWVRQAPGQGL EWMGGITPFFGFADYAQKFQGRVTITADESTTTAYMELSGLTSDDT AVYYCARDPNEFWNGYYSTHDFDSWGQG | 11 |
| VL | EIVLTQSPDFQSVTPKEKVTITCRASQDIGSELHWYQQKPDQPPKLLI KYASHSTGVPSRFSGSGSGTDFTLTINGLEAEDAGTYYCHQTDSLP YTFGPG | 12 |
| VH | EVQLVQSGAEVKKPGASVKVSCKASGYTFTDYEVHWVRQAPGQG LEWMGVIDPGTGGVAYNQKFEGRVTMTADTSTSTAYMELRSLRSD DTAVYYCTRYSLFYGSSPYAMDYWGQG | 13 |
| VL | EIVLTQSPDFQSVTPKEKVTITCSASSSVNYMHWFQQKPDQSPKLWI YRTSNLASGVPSRFSGSGSGTDYTLTINSLEAEDAATYYCQQRSSYP WTFGQG | 14 |
| VH | EVQLVESGGGLVQPGGSLRLSCAASGMSMSDYWMNWVRQAPGK GLEWVAAINQDGDEKYYVGSVKGRFTISRDNAKNSLYLQMNSLRV EDTAVYYCVRDYYDLISDYYIHYWYFDLWGRG | 15 |
| VL | DIQMTQSPSSLSASVGDRVTIHCRASQNVHNRLTWYQQKPGKAPK LLIYGASNLESGVPSRFSGSGSGTDFTLTISSLQPEDFATYYCQQYNG SPTTFGQG | 16 |

Examples of amino acid sequences of the light chain constant regions and the heavy chain constant regions of the anti-IL-17 antibodies comprised in the fusion protein of the present invention are provided in the following Tables 2 and 3 below.

TABLE 2

Examples of the amino acid sequences of the light chain constant regions in the antigen-binding fragment of the anti-IL-17 antibody comprised in the fusion protein of the present invention

| Type of light chain | Amino acid sequence of light chain constant region | SEQ ID NO: |
|---|---|---|
| κ | TKVEIKRTVAAPSVFIFPPSDEQLKSGTASVVCLLNNFYPREAKVQ WKVDNALQSGNSQESVTEQDSKDSTYSLSSTLTLSKADYEKHKVY ACEVTHQGLSSPVTKSFNRGEC | 17 |
| λ | TKLTVLGQPKAAPSVTLFPPSSEELQANKATLVCLISDFYPGAVTVA WKADSSPVKAGVETTTPSKQSNNKYAASSYLSLTPEQWKSHRSYSC QVTHEGSTVEKTVAPTECS | 18 |

TABLE 3

Examples of the amino acid sequences of the heavy chain constant regions in the antigen-binding fragment of the anti-IL-17 antibody comprised in the fusion protein of the present invention

| Class of heavy chain | Amino acid sequence of heavy chain constant region | SEQ ID NO: |
|---|---|---|
| IgG1 | TLVTVSSASTKGPSVFPLAPSSKSTSGGTAALGCLVKDYFPEPVTVS WNSGALTSGVHTFPAVLQSSGLYSLSSVVTVPSSSLGTQTYICNVN HKPSNTKVDKKVEPKSCDKTHTCPPCPAPELLGGPSVFLFPPKPKDT LMISRTPEVTCVVVDVSHEDPEVKFNWYVDGVEVHNAKTKPREEQ YNSTYRVVSVLTVLHQDWLNGKEYKCKVSNKALPAPIEKTISKAK GQPREPQVYTLPPSREEMTKNQVSLTCLVKGFYPSDIAVEWESNGQ PENNYKTTPPVLDSDGSFFLYSKLTVDKSRWQQGNVFSCSVMHEA LHNHYTQKSLSLSPGK | 19 |
| IgG2 | TTVTVSTASTKGPSVFPLAPCSRSTSESTAALGCLVKDYFPEPVTVS WNSGALTSGVHTFPAVLQSSGLYSLSSVVTVPSSNFGTQTYTCNVD HKPSNTKVDKTVERKCCVECPPCPAPPVAGPSVFLFPPKPKDTLMIS RTPEVTCVVVDVSHEDPEVQFNWYVDGVEVHNAKTKPREEQFNST FRVVSVLTVVHQDWLNGKEYKCKVSNKGLPAPIEKTISKTKGQPRE PQVYTLPPSREEMTKNQVSLTCLVKGFYPSDIAVEWESNGQPENNY KTTPPMLDSDGSFFLYSKLTVDKSRWQQGNVFSCSVMHEALHNHY TQKSLSLSPGK | 20 |
| IgG4 | TLVTVSSASTKGPSVFPLAPCSRSTSESTAALGCLVKDYFPEPVTVS WNSGALTSGVHTFPAVLQSSGLYSLSSVVTVPSSSLGTKTYTCNVD HKPSNTKVDKRVESKYGPPCPPCPAPEFLGGPSVFLFPPKPKDTLMI SRTPEVTCVVVDVSQEDPEVQFNWYVDGVEVHNAKTKPREEQFNS TYRVVSVLTVLHQDWLNGKEYKCKVSNKGLPSSIEKTISKAKGQPR EPQVYTLPPSQEEMTKNQVSLTCLVKGFYPSDIAVEWESNGQPENN YKTTPPVLDSDGSFFLYSRLTVDKSRWQEGNVFSCSVMHEALHNH YTQKSLSLSLGK | 21 |

II-2 Immunoglobulin Fc Domain

The term "Fc region" as used herein is to define the C-terminus region of the immunoglobulin heavy chain that contains at least a portion of the constant region. The term includes native sequence Fc regions and variant Fc regions. In some embodiments, a human IgG heavy chain Fc-region extends from Cys226 or from Pro230 to the carboxyl-terminus of the heavy chain. However, the C-terminal lysine (Lys447) of the Fc region may or may not be present. Unless otherwise specified herein, numbering of amino acid residues in the Fc-region or constant region is according to the EU numbering system, also called the EU index, as described in Kabat et al., Sequences of Proteins of Immunological Interest, 5th ed., Public Health Service, National Institutes of Health, Bethesda, Md., 1991.

The "immunoglobulin Fc domain" in the fusion protein of the present invention comprises all the amino acid residues of the naturally occurring immunoglobulin Fc domain or a part of the amino acid residues of the naturally occurring immunoglobulin Fc domain. The immunoglobulin Fc domain provides favorable pharmacokinetic properties for the fusion protein of the present invention, including but not limited to long serum half-life. In addition, the immunoglobulin Fc domain also makes it possible to purify the fusion protein of the present invention by, for example, protein A affinity chromatography.

An immunoglobulin Fc domain is usually a dimeric molecule, which can be produced by papain digestion or trypsin digestion of an intact (full-length) immunoglobulin or can be recombinantly produced, comprising CH2 domain, CH3 domain and optional CH4 domain. Examples of the amino acid sequence of the heavy chain Fc in the antigen-binding fragment of the anti-IL-17 antibody comprised in the fusion protein of the present invention are provided in Table 4 below.

TABLE 4

Examples of the amino acid sequence of the heavy chain Fc in the antigen-binding ragment of the anti-IL-17 antibody comprised in the fusion protein of the present invention

| Class of heavy chain | Amino acid sequence of the heavy chain Fc | SEQ ID NO: |
|---|---|---|
| IgG1 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQ DWLNGKEYKCKVSNKALPAPIEKTISKAKGQPREPQVYTLPPSREE MTKNQVSLTCLVKGFYPSDIAVEWESNGQPENNYKTTPPVLDSDGS FFLYSKLTVDKSRWQQGNVFSCSVMHEALHNHYTQKSLSLSPGK | 75 |
| IgG2 | DKTVERKCCVECPPCPAPPVAGPSVFLFPPKPKDTLMISRTPEVTCV VVDVSHEDPEVQFNWYVDGVEVHNAKTKPREEQFNSTFRVVSVLT VVHQDWLNGKEYKCKVSNKGLPAPIEKTISKTKGQPREPQVYTLPP | 76 |

TABLE 4-continued

Examples of the amino acid sequence of the heavy chain Fc in the antigen-binding ragment of the anti-IL-17 antibody comprised in the fusion protein of the present invention

| Class of heavy chain | Amino acid sequence of the heavy chain Fc | SEQ ID NO: |
|---|---|---|
| | SREEMTKNQVSLTCLVKGFYPSDIAVEWESNGQPENNYKTTPPML DSDGSFFLYSKLTVDKSRWQQGNVFSCSVMHEALHNHYTQKSLSL SPGK | |
| IgG4 | DKRVESKYGPPCPPCPAPEFLGGPSVFLFPPKPKDTLMISRTPEVTCV VVDVSQEDPEVQFNWYVDGVEVHNAKTKPREEQFNSTYRVVSVL TVLHQDWLNGKEYKCKVSNKGLPS SIEKTIS KAKGQPREPQVYTLP PSQEEMTKNQVSLTCLVKGFYPSDIAVEWESNGQPENNYKTTPPVL DSDGSFFLYSRLTVDKSRWQEGNVFSCSVMHEALHNHYTQKSLSL SLGK | 77 |

II-3 TNFR Extracellular Region

The term "TNFR" as used herein refers to a receptor for tumor necrosis factor (TNF), which is a glycoprotein. The term "extracellular region" as used herein refers to a part of TNFR that is outside the cell membrane in the natural environment.

The TNFR functional region in the fusion protein of the anti-L-17 antibody and the TNFR extracellular domain may comprise the full length of the TNFR extracellular domain: CRD1-CRD2-CRD3-CRD4, or a part of the extracellular domain: a fragment of CRD 1-CRD2-CRD 3-CRD4.

Examples of the amino acid sequence of the TNFR extracellular region and of a part thereof comprised in the fusion protein of the present invention are provided in Table 5 below.

TABLE 5

Examples of amino acid sequences of the TNFR extracellular region and of a part thereof comprised in the fusion protein of the present invention.

| | Functional region | Amino acid sequence | SEQ ID NO: |
|---|---|---|---|
| TNFR2 | Full length of TNFR2 extracellular region | LPAQVAFTPYAPEPGSTCRLREYYDQTAQMCCSKCSPG QHAKVFCTKTSDTVCDSCEDSTYTQLWNWVPECLSCGS RCSSDQVETQACTREQNRICTCRPGWYCALSKQEGCRL CAPLRKCRPGFGVARPGTETSDVVCKPCAPGTFSNTTSS TDICRPHQICNVVAIPGNASMDAVCTSTSPTRSMAPGAV HLPQPVSTRSQHTQPTPEPSTAPSTSFLLPMGPSPPAEGST GD | 22 |
| | Part of TNFR2 extracellular region | LPAQVAFTPYAPEPGSTCRLREYYDQTAQMCCSKCSPG QHAKVFCTKTSDTVCDSCEDSTYTQLWNWVPECLSCGS RCSSDQVETQACTREQNRICTCRPGWYCALSKQEGCRL CAPLRKCRPGFGVARPGTETSDVVCKPCAPGTFSNTTSS TDICRPHQI | 23 |
| TNFR1 | Full length of TNFR1 extracellular region | LVPHLGDREKRDSVCPQGKYIHPQNNSICCTKCHKGTYL YNDCPGPGQDTDCRECESGSFTASENHLRHCLSCSKCRK EMGQVEISSCTVDRDTVCGCRKNQYRHYWSENLFQCFN CSLCLNGTVHLSCQEKQNTVCTCHAGFFLRENECVSCSN CKKSLECTKLCLPQIENVKGTEDSGTT | 24 |
| | Partof TNFR1 extracellular region | LVPHLGDREKRDSVCPQGKYIHPQNNSICCTKCHKGTYL YNDCPGPGQDTDCRECESGSFTASENHLRHCLSCSKCRK EMGQVEISSCTVDRDTVCGCRKNQYRHYWSENLFQCFN CSLCLNGTVHLSCQEKQNTVCTCHAGFFLRENECVSCSN CKKSLE | 25 |

II-4 Linker Peptide

The term "linker peptide" as used herein refers to a short peptide that can link two polypeptide sequences, and is about 1-100 amino acid residues in length.

The anti-IL-17 antibody and the TNFR extracellular region in the fusion protein of the present invention are linked via a linker peptide, wherein the amino acid sequence of the linker peptide may be selected from any one of

AKTTPKLEEGEFSEAR; (SEQ ID NO: 30)

AKTTPKLEEGEFSEARV; (SEQ ID NO: 31)

AKTTPKLGG; (SEQ ID NO: 32)

SAKTTPKLGG; (SEQ ID NO: 33)

SAKTTP; (SEQ ID NO: 34)

RADAAP; (SEQ ID NO: 35)

RADAAPTVS; (SEQ ID NO: 36)

RADAAAAGGPGS; (SEQ ID NO: 37)

RADAAAA; (SEQ ID NO: 38)

SAKTTPKLEEGEFSEARV; (SEQ ID NO: 39)

ADAAP; (SEQ ID NO: 40)

DAAPTVSIFPP; (SEQ ID NO: 41)

TVAAP; (SEQ ID NO: 42)

TVAAPSVFIFPP; (SEQ ID NO: 43)

QPKAAP; (SEQ ID NO: 44)

QPKAAPSVTLFPP; (SEQ ID NO: 45)

AKTTPP; (SEQ ID NO: 46)

AKTTPPSVTPLAP; (SEQ ID NO: 47)

AKTTAP; (SEQ ID NO: 48)

AKTTAPSVYPLAP; (SEQ ID NO: 49)

ASTKGP; (SEQ ID NO: 50)

ASTKGPSVFPLAP; (SEQ ID NO: 51)

GGGGSGGGGSGGGGS; (SEQ ID NO: 52)

GENKVEYAPALMALS; (SEQ ID NO: 53)

GPAKELTPLKEAKVS; (SEQ ID NO: 54)

GHEAAAVMQVQYPAS; (SEQ ID NO: 55)

GGGGSGGGGSGGGGSA; (SEQ ID NO: 56)

GQGTKVEIKRGGSGGGGSG; (SEQ ID NO: 57)

GQGTLVTVSSGGGGSGGGGS. (SEQ ID NO: 58)

The fusion protein of the present invention, comprising anti-IL-17 antibody and TNFR, has the function of binding IL-17 and TNF-α, that is, upon binding either IL-17 or TNF-α, the fusion protein can still bind another target.

The fusion protein of the present invention, comprising anti-IL-17 antibody and TNFR, can synergistically inhibit the biological functions of IL-17 and TNF-α, inhibit the release of inflammatory mediators such as chemokines and lymphokines, and the inhibitory effects are comparable to those derived from the combination of the anti-IL-17 antibody and the TNF-α inhibitor, more potent than anti-IL-17antibody alone or TNF-α inhibitor alone.

The fusion protein of the present invention, comprising anti-IL-17 antibody and TNFR, can be used for the treatment of autoimmune diseases such as rheumatoid arthritis, ankylosing spondylitis, psoriasis and ulcerative colitis.

III. Production and Purification of the Fusion Protein of the Present Invention

The fusion protein of the present invention can be obtained, for example, by solid-state peptide synthesis (for example, Merrifield solid-phase synthesis) or recombinant production. For recombinant production, the polynucleotide encoding the first subunit of the fusion protein and/or the polynucleotide encoding the second subunit of the fusion protein are isolated and inserted into one or more vectors for further cloning and/or expressing in a host cellon. Using conventional methods, the polynucleotides can be easily isolated and sequenced. In one embodiment, a vector, preferably an expression vector, comprising one or more polynucleotides of the invention is provided.

The expression vector can be constructed using methods well known to those skilled in the art. Expression vectors include but are not limited to viruse vectors, plasmids, cosmids, lambda phage, or yeast artificial chromosomes (YAC). In a preferred embodiment, a glutamine synthetase high-efficiency expression vector with dual expression cassettes is used.

Once an expression vector comprising one or more polynucleotides of the invention has been prepared for expression, the expression vector can be transfected or introduced into a suitable host cell. Various techniques can be used for this purpose, for example, protoplast fusion, calcium phosphate precipitation, electroporation, retrovirus transduction, viral transfection, gene gun, liposome-based transfection, or other conventional techniques.

Standard techniques for expressing foreign genes in these host cell systems are known in the art. In one embodiment, a method of producing a fusion protein of the invention is provided, comprising culturing a host cell as provided herein comprising polynucleotide(s) encoding the fusion protein under conditions suitable for expression of the fusion protein, and recovering the fusion protein from the host cell (or the host cell culture medium).

Fusion proteins prepared as described herein may be purified by art-known techniques such as high performance liquid chromatography, ion exchange chromatography, gel electrophoresis, affinity chromatography, size exclusion chromatography, and the like. The actual conditions used to purify a particular protein will also depend on factors such as net charge, hydrophobicity, hydrophilicity etc., and will be apparent to those having skill in the art.

The purity of the fusion protein of the present invention can be determined by any of a variety of well-known analysis methods including gel electrophoresis, high-performance liquid chromatography, and the like. The physical/chemical properties and/or biological activities of the fusion proteins provided herein can be identified, screened, or characterized by various assays known in the art.

IV. Pharmaceutical Composition and Kit

As used herein, the term "pharmaceutical composition" refers to a formulation that exists in a form allowing the biological activity of the active ingredient contained therein to be effective, and does not include additional ingredients with unacceptable toxicity to the individual to whom the formulation is administered. The pharmaceutical composition of the present invention is suitable for intravenous, intramuscular, subcutaneous, parenteral, rectal, spinal or epidermal administration (for example, by injection or infusion).

The term "pharmaceutically acceptable carrier" as used herein includes any and all solvents, dispersion media, isotonic agents and absorption delaying agents, etc. that are physiologically compatible.

The pharmaceutical composition of the present invention can comprise the fusion protein of the present invention and a pharmaceutically acceptable carrier. These pharmaceutical compositions may be included in kits, such as diagnostic kits.

Pharmaceutically acceptable carriers suitable for use in the present invention may be sterile liquids, such as water and oil, including those of petroleum, animal, vegetable or synthetic source, such as peanut oil, soybean oil, mineral oil, sesame oil, and the like. When the pharmaceutical composition is administered intravenously, water is the preferred carrier. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. For the use of excipients, see also "Handbook of Pharmaceutical Excipients", Fifth Edition, R. C. Rowe, P. J. Seskey and S. C. Owen, Pharmaceutical Press, London, Chicago. The compositions, if desired, can also contain minor amounts of wetting or emulsifying agents, or pH buffering agents. These compositions can take the form of solutions, suspensions, emulsions, tablets, pills, capsules, powders, sustained release formulations and the like. Oral formulations may contain standard carriers such as pharmaceutical grade mannitol, lactose, starch, magnesium stearate, saccharin.

The pharmaceutical formulation comprising the fusion protein of the invention can be prepared by mixing the fusion protein of the invention having the desired purity with one or more optional pharmaceutical carriers (Remington's Pharmaceutical Sciences, 16th edition, Osol, A. Ed. (1980)). Preferably, the pharmaceutical formulation is in a lyophilized or aqueous solution form.

An exemplary lyophilized antibody formulation is described in U.S. Pat. No. 6,267,958. Aqueous antibody formulations include those described in U.S. Pat. No. 6,171,586 and WO2006/044908, the latter formulation comprises a histidine-acetate buffer.

The pharmaceutical composition or formulation of the present invention may comprise more than one active ingredient that is required for the specific indication being treated, preferably those active ingredients that do not adversely affect each other's complementary activities, and suitably present in combination in an amount effective for the intended use.

Sustained-release formulations can be prepared. Suitable examples of sustained-release formulations include semipermeable matrices of antibody-comprising solid hydrophobic polymers, which matrices are in the form of shaped articles, such as films or microcapsules.

The composition of the present invention may be in various forms, including for example, liquid, semi-solid, and solid dosage forms, such as liquid solutions (eg, injectable solutions and infusible solutions), dispersions or suspensions, liposomes, and suppositories. The preferred form depends on the intended mode of administration and therapeutic use. Commonly preferred compositions are in the form of injectable solutions or infusible solutions. The preferred mode of administration is parenteral (eg, intravenous, subcutaneous, intraperitoneal (i.p.), intramuscular) injection. In a preferred embodiment, the fusion protein is administered by intravenous infusion or injection. In another preferred embodiment, the fusion protein is administered by intramuscular, intraperitoneal or subcutaneous injection.

The phrases "parenteral administration" and "administered parenterally" as used herein mean a mode of administration other than enteral and local administration, usually by injection, and include but are not limited to intravenous, intramuscular, intraarterial, intradermal, intraperitoneal, transtracheal, subcutaneous injection and infusion.

Therapeutic compositions should generally be sterile and stable under the conditions of manufacture and storage. The composition can be formulated as a solution, microemulsion, dispersion, liposome, or lyophilized form. Sterile injectable solutions can be prepared by incorporating the required amount of the active compound (ie, fusion protein) into a suitable solvent followed by filter sterilization. Generally, dispersions are prepared by incorporating the active compound into a sterile vehicle that contains a basic dispersion medium and other ingredients. Coating agents such as lecithin and the like can be used. In the case of dispersions, the proper fluidity of the solution can be maintained by using surfactants. Prolonged absorption of the injectable composition can be achieved by including substances that delay absorption in the composition, such as monostearate and gelatin.

In certain embodiments, the fusion protein of the present invention can be administered orally, for example, in an inert diluent or an edible carrier. The fusion protein of the present invention can also be enclosed in hard or soft shell gelatin capsules, compressed into tablets or directly incorporated into an individual's diet. For oral therapeutic administration, the compound can be incorporated with excipients and taken as ingestible tablets, buccal tablets, troches, capsules, elixirs, suspensions, syrups, wafer or the like form. In order to administer the fusion protein of the present invention by a non-parenteral administration method, it may be necessary to coat or co-administer the fusion protein with a material that prevents its inactivation. Therapeutic compositions can also be administered via medical devices known in the art.

The pharmaceutical composition of the present invention can comprise a "therapeutically effective amount" or "prophylactically effective amount" of the fusion protein of the present invention. "Therapeutically effective amount" refers to an amount that is effective to achieve the desired therapeutic result at the required dose for the required period of time. The therapeutically effective amount can be varied according to various factors such as disease state, individual's age, sex, and weight. A therapeutically effective amount is any amount that is less toxic or harmful than the beneficial effect of treatment. The "therapeutically effective amount" preferably inhibits measurable parameters (eg, tumor growth rate) by at least about 20%, more preferably at least about 40%, even more preferably at least about 60%, and still more preferably at least about 80% relative to untreated individuals. The ability of the fusion protein of the invention to inhibit measurable parameters (eg, tumor volume) can be evaluated in animal model systems that predict efficacy on human tumors.

"Prophylactically effective amount" refers to an amount that is effective to achieve the desired preventive result at the required dose for the required period of time. Generally, because the prophylactic dose is used in an individual before or at an earlier stage of the disease, the prophylactically effective amount is less than the therapeutically effective amount.

Kits comprising the fusion proteins herein are also within the scope of the present invention. The kit may contain one or more other elements, including, for example, instructions for use; other reagents, such as labels or coupling reagents; pharmaceutically acceptable carriers; and devices helpful for administration to individuals or other materials.

V. Uses of Fusion Protein

The fusion protein disclosed herein have in vitro and in vivo diagnostic uses as well as therapeutic and prophylactic uses. For example, these molecules can be administered to cultured cells in vitro or ex vivo or to an individual, for example, a human individual, to treat, prevent and/or diagnose various diseases related to the biological activities of IL-17 and TNF-α, for example, autoimmune diseases.

In one aspect, the present invention provides diagnostic methods for detecting the presence of IL-17 and TNF-α in biological samples in vitro or in vivo, such as serum, semen, or urine or tissue biopsy samples (eg, from hyperproliferative or cancerous lesions). The diagnostic method includes: (i) contacting a sample (and optionally, a control sample) with a fusion protein as described herein or administering the fusion protein to an individual under conditions allowing interaction to occur, and (ii) detecting the formation of complex between the fusion protein and the sample (and optionally, control sample). The formation of the complex indicates the presence of IL-17 and TNF-α, and may show the applicability or need for the treatment and/or prevention described herein.

In some embodiments, IL-17 and TNF-α are assayed before treatment, for example, before initiating treatment or before a certain treatment after a treatment interval. Assays that can be used include immunohistochemistry, immunocytochemistry, FACS, ELISA assays, PCR-technologies (eg, RT-PCR) or in vivo imaging techniques. Generally, fusion proteins used in in vivo and in vitro detection methods are directly or indirectly labeled with a detectable substance to facilitate detection of bound or unbound bindets. Suitable detectable substances include various biologically active enzymes, prosthetic groups (??), fluorescent substances, luminescent substances, paramagnetic (eg, nuclear magnetic resonance active) substances, and radioactive substances.

In some embodiments, the levels and/or distribution of IL-17 and TNF-α are determined in vivo, for example, in a non-invasive manner (eg, by using suitable imaging techniques (eg, positron emission tomography (PET) Scanning) to detect the fusion protein of the present invention labeled with a detectable substance. In one embodiment, for example, by detecting the fusion protein of the present invention labeled with a PET reagent (eg, $^{18}$F-fluorodeoxyglucose (FDG)) in a detectable manner, to determine the levels and/or distributions of IL-17 and TNF-α.

In one embodiment, the present invention provides a diagnostic kit comprising the fusion protein described herein and instructions for use.

In another aspect, the present invention relates to the use of fusion proteins in vivo to treat or prevent diseases that require enhanced biological activities of IL-17 and TNF-α in an individual, thereby inhibiting or reducing the occurrence or relapse of related diseases such as autoimmune diseases. The fusion protein can be used alone to suppress or prevent the occurrence of autoimmune diseases. Alternatively, the fusion protein may be administered in combination with other autoimmune disease treatment/preventive agents. When the fusion protein of the present invention is administered in combination with one or more other drugs, the components in this combination can be administered in any order or simultaneously Thus, in one embodiment, the present invention provides a method of inhibiting the occurrence of autoimmune diseases in an individual, comprising administering to the individual a therapeutically effective amount of the fusion protein described herein. In another embodiment, the present invention provides a method of preventing the occurrence or recurrence of an autoimmune disease in an individual, comprising administering to the individual a prophylactically effective amount of the fusion protein described herein.

In some embodiments, autoimmune diseases treated and/or prevented with the fusion protein of the present invention include, but are not limited to: autoimmune rheumatoid arthritis, lupus, myasthenia gravis, ankylosing spondylitis, hyperthyroidism, hypothyroidism, ulcerative colitis, Crohn's disease, heart valve disease, multiple sclerosis, scleroderma, and autoimmune hepatitis, more preferably rheumatoid arthritis, ankylosing spondylitis, psoriasis, and ulcerative colitis.

The disease related to the biological activity of IL-17 in the present invention means a disease related to excessive level or activity of IL-17, wherein atypical symptoms may be manifested locally and/or systemically in the body due to the level or activity of IL-17. Examples of diseases related to IL-17 biological activity include: atopic dermatitis, allergic rhinitis, asthma, fibrosis, inflammatory bowel disease, Crohn's disease, pneumonic disease, pulmonary fibrosis, idiopathic pulmonary fiber (IPF), chronic obstructive pulmonary disease (COPD), liver fibrosis, respiratory diseases, cancer, glioblastoma, and non-Hodgkin's lymphoma. In any of the embodiments described herein, respiratory diseases may be selected from the group consisting of asthma, allergic asthma, non-allergic asthma, bronchitis, chronic bronchitis, chronic obstructive pulmonary disease (COPD), emphysema, cigarette-induced emphysema, airway inflammation, cystic fibrosis, pulmonary fibrosis, allergic rhinitis, and bronchiectasis.

The following Examples are described to assist in the understanding of the present invention. It is not intended and should not be construed in any way to limit the scope of protection of the present invention.

All publications, patent applications, patents, and other references mentioned herein are incorporated by reference in their entirety. In addition, the materials, methods, and examples described herein are illustrative only and are not intended to be limiting. Other features, objects, and advantages of the invention will be derived from the description and drawings, and from the appended claims.

Specific Embodiments

Example 1. Construction of a Glutamine Synthetase High-Efficiency Expression Vector Comprising the Gene of Interest (1) Synthesis of a Nucleotide Encoding Anti-IL-17A Antibody BY19.4 as Control and Construction of an Expression Vector Therefor After optimizing the amino acid sequence of ixekizumab monoclonal antibody under accession number 9467 in the International Nonproprietary Name (INN) database, to suitable for expression in Chinese hamster ovary cancer cells (CHO), the following nucleotide sequence were chosen and entrusted to Shanghai Generay Biotech. Co. Ltd. to synthesize the nucleotide sequences. The anti-IL-17A antibody produced after the expression of the nucleotide sequence is expressed herein as antibody BY19.4.

```
BY19.4 light chain (BY19.4L) nucleotide sequence (SEQ ID NO: 26):
TCTAGAGCCACCATGGAGACCGACACCCTCCTCCTGTGGGTGCTGCTGCTGTGGGTGCC

CGGCTCTACCGGCGACATCGTGATGACTCAGACACCACTGAGCCTGTCTGTGACCCCA

GGCCAGCCCGCTTCGATTTCTTGCCGGTCCTCTCGCAGCCTGGTGCACTCTAGGGGCAA

CACATACCTCCACTGGTATCTACAGAAGCCCGGCCAGTCCCCTCAGCTGCTGATCTACA

AGGTGTCTAACAGGTTCATTGGCGTGCCCGACCGCTTCTCCGGCTCTGGCAGCGGCACC

GACTTCACACTCAAGATTAGCAGAGTGGAGGCTGAGGACGTGGGCGTGTACTACTGCT

CTCAGTCTACCCACCTCCCTTTCACATTCGGCCAGGGCACAAAGGTGGAGATCAAGCG

GACCGTGGCCGCCCCATCCGTGTTCATTTTCCCACCTTCCGACGAGCAGCTGAAGTCTG

GCACCGCCAGCGTGGTGTGCCTGCTGAACAACTTCTACCCCCGCGAGGCCAAGGTGCA

GTGGAAGGTGGACAACGCCCTGCAGAGCGGCAACAGCCAGGAGAGCGTGACCGAGCA

GGACTCCAAGGACAGCACCTACAGCCTGAGCAGCACCCTGACCCTGAGCAAGGCCGAC

TACGAGAAGCACAAGGTGTACGCCTGCGAGGTGACCCACCAGGGACTGTCTAGCCCCG

TGACCAAGAGCTTCAACCGGGGCGAGTGCTAAGAATT GTCGAC

BY19.4 light chain (BY19.4L) amino acid sequence (SEQ ID NO: 27), as first subunit:
METDTLLLWVLLLWVPGSTGDIVMTQTPLSLSVTPGQPASISCRSSRSLVHSRGNTYLHWY

LQKPGQSPQLLIYKVSNRFIGVPDRFSGSGSGTDFTLKISRVEAEDVGVYYCSQSTHLPFTFG

QGTKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

BY 19.4 heavy chain (BY 19.4H) nucleotide sequence(SEQ ID NO: 28):
CTCGAGGCCACCATGGAGACCGACACACTCCTCCTGTGGGTGCTGCTGCTCTGGGTGCC

AGGCAGCACCGGCCAGGTGCAGCTCGTGCAGAGCGGCGCCGAGGTGAAGAAGCCCGG

CTCTTCTGTGAAGGTGTCTTGCAAGGCTTCCGGCTACTCTTTCACCGACTACCACATTC

ACTGGGTGCGCCAGGCTCCTGGCCAGGGCCTTGAGTGGATGGGCGTGATTAACCCTAT

GTACGGCACAACAGACTACAACCAGCGGTTCAAGGGCAGAGTGACCATTACAGCCGA

CGAGTCCACATCCACCGCTTACATGGAGCTGTCCTCCCTGCGTTCTGAGGACACTGCTG

TGTACTACTGCGCTAGATACGACTACTTCACCGGCACTGGCGTGTACTGGGGCCAGGG

CACACTCGTGACCGTGTCTAGCGCATCAACAAAGGGCCCATCTGTGTTCCCACTCGCCC

CATGCTCCCGCTCCACCTCCGAGTCCACCGCCGCCCTGGGCTGCCTGGTGAAGGACTAC

TTCCCTGAGCCTGTGACCGTGTCCTGGAACTCCGGCGCCCTGACCTCCGGCGTGCACAC

CTTCCCTGCCGTGCTGCAGTCCTCCGGCCTGTACTCCCTGTCCTCCGTGGTGACCGTGCC
```

-continued
```
TTCCTCCTCCCTGGGCACCAAGACCTACACCTGCAACGTGGACCACAAGCCTTCCAACA

CCAAGGTGGACAAGCGCGTGGAGTCCAAGTACGGCCCTCCTTGCCCTCCTTGCCCTGCC

CCTGAGTTCCTGGGCGGCCCTTCCGTGTTCCTGTTCCCTCCTAAGCCTAAGGACACCCT

GATGATCTCCCGCACCCCTGAGGTGACCTGCGTGGTGGTGGACGTGTCCCAGGAGGAC

CCTGAGGTGCAGTTCAACTGGTACGTGGACGGCGTGGAGGTGCACAACGCCAAGACCA

AGCCTCGCGAGGAGCAGTTCAACTCCACCTACCGCGTGGTGTCCGTGCTGACCGTGCT

GCACCAGGACTGGCTGAACGGCAAGGAGTACAAGTGCAAGGTGTCCAACAAGGGCCT

GCCTTCCTCCATCGAGAAGACCATCTCCAAGGCCAAGGGCCAGCCTCGCGAGCCTCAG

GTGTACACCCTGCCTCCTTCCCAGGAGGAGATGACCAAGAACCAGGTGTCCCTGACCT

GCCTGGTGAAGGGCTTCTACCCTTCCGACATCGCCGTGGAGTGGGAGTCCAACGGCCA

GCCTGAGAACAACTACAAGACCACCCCTCCTGTGCTGGACTCCGACGGCTCCTTCTTCC

TGTACTCCCGCCTGACCGTGGACAAGTCCCGCTGGCAGGAGGGCAACGTGTTCTCCTG

CTCCGTGATGCACGAGGCCCTGCACAACCACTACACCCAGAAGTCCCTGTCCCTGTCCC

TGGGCTAAGAATTC
```

BY19.4 heavy chain (BY19.4H) amino acid sequence (SEQ ID NO: 29), as second subunit:
<u>METDTLLLWVLLLWVPGSTG</u>QVQLVQSGAEVKKPGSSVKVSCKASGYSFTDYHIHWVRQ

APGQGLEWMGVINPMYGTTDYNQRFKGRVTITADESTSTAYMELSSLRSEDTAVYYCARY

DYFTGTGVYWGQGTLVTVSSASTKGPSVFPLAPCSRSTSESTAALGCLVKDYFPEPVTVSW

NSGALTSGVHTFPAVLQSSGLYSLSSVVTVPSSSLGTKTYTCNVDHKPSNTKVDKRVESKY

GPPCPPCPAPEFLGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAKGQP

REPQVYTLPPSQEEMTKNQVSLTCLVKGFYPSDIAVEWESNGQPENNYKTTPPVLDSDGSF

FLYSRLTVDKSRWQEGNVFSCSVMHEALHNHYTQKSLSLSLG wherein the underlined "METDTLLLWVLLLWVPG-STG" (SEQ ID NO: 78) is the signal peptide sequence.

Shanghai Generay Biotech. Co. Ltd. synthesized the above BY19.4 light chain (BY19.4L) encoding nucleotide sequence, and BY19.4 heavy chain (BY19.4H) encoding nucleotide sequence. The BY19.4L encoding nucleotide sequence and a glutamine synthetase high-efficiency expression vector with dual expression cassettes (Chinese patent No. CN104195173B, obtained from Beijing Beyond Biotechnology Co., Ltd) were double digested with XbaI-SalI respectively. Then, the XbaI-SalI double-digested BY19.4L encoding nucleotide was ligated into the XbaI-SalI double-digested expression vector by using ligase, to introduce BY19.4L encoding nucleotide into the expression vector. The BY19.4H encoding nucleotide sequence and the expression vector with introduced BY19.4L encoding nucleotide were double digested with XhoI-EcoRI respectively. Then, the XhoI-EcoRI double-digested BY19.4H encoding nucleotide was ligated into the XhoI-EcoRI double-digested expression vector by using ligase, to introduce BY19.4L encoding nucleotide into the expression vector, thus both BY19.4L encoding nucleotide and BY19.4H encoding nucleotide were introduced into the glutamine synthetase high-efficiency expression vector with dual expression cassettes. After sequencing to confirm a correct expression would be achieved, the expression vector of anti-IL-17 antibody BY19.4 was obtained.

Alternatively, the expression vector of anti-IL-17 antibody BY19.4 can be obtained by ligating BY19.4L encoding nucleotide into a glutamine synthetase high-efficiency expression vector with dual expression cassettes having BY19.4H encoding nucleotide introduced therein, to express and obtain antibody BY19.4.

(2) Synthesis of Exemplary Fusion Protein Encoding Nucleotides and Construction of Expression Vectors After optimizing the heavy chain variable region and light chain variable region sequences of the anti-IL-17 antibody in Table 1, the light chain constant region sequences of the antibody in Table 2, the heavy chain constant region sequences of the antibody in Table 3, the TNFR extracellular region sequences in Table 4, and the linker peptide sequences of SEQ ID NOs: 30-58, to suitable for expression in Chinese hamster ovary cancer cells (CHO), the following polynucleotide sequences of SEQ ID NOs: 59, 61, 63, 65, 67, 69, 71, 73 were chosen and entrusted to Shanghai Generay Biotech. Co. Ltd. to synthesize the polynucleotide sequences.

First subunit nucleotide sequence (SEQ ID NO: 59) of fusion protein BY19.3(κ, IgG4):
TCTAGAGCCACCATGGAGACCGACACCCTCCTCCTGTGGGTGCTGCTGCTGTGGGTGCC

CGGCTCTACCGGCGACATCGTGATGACTCAGACACCACTGAGCCTGTCTGTGACCCCA

GGCCAGCCCGCTTCGATTTCTTGCCGGTCCTCTCGCAGCCTGGTGCACTCTAGGGGCAA

CACATACCTCCACTGGTATCTACAGAAGCCCGGCCAGTCCCCTCAGCTGCTGATCTACA

AGGTGTCTAACAGGTTCATTGGCGTGCCCGACCGCTTCTCCGGCTCTGGCAGCGGCACC

GACTTCACACTCAAGATTAGCAGAGTGGAGGCTGAGGACGTGGGCGTGTACTACTGCT

CTCAGTCTACCCACCTCCCTTTCACATTCGGCCAGGGCACAAAGGTGGAGATCAAGCG

GACCGTGGCCGCCCCATCCGTGTTCATTTTCCCACCTTCCGACGAGCAGCTGAAGTCTG

GCACCGCCAGCGTGGTGTGCCTGCTGAACAACTTCTACCCCCGCGAGGCCAAGGTGCA

GTGGAAGGTGGACAACGCCCTGCAGAGCGGCAACAGCCAGGAGAGCGTGACCGAGCA

GGACTCCAAGGACAGCACCTACAGCCTGAGCAGCACCCTGACCCTGAGCAAGGCCGAC

TACGAGAAGCACAAGGTGTACGCCTGCGAGGTGACCCACCAGGGACTGTCTAGCCCCG

TGACCAAGAGCTTCAACCGGGGCGAGTGCTAAGAATT GTCGAC

First subunit amino acid sequence (SEQ ID NO: 60 = SEQ ID NO: 27) of fusion protein BY19.3(k, IgG4):
METDTLLLWVLLLWVPGSTGDIVMTQTPLSLSVTPGQPASISCRSSRSLVHSRGNTYLHWY

LQKPGQSPQLLIYKVSNRFIGVPDRFSGSGSGTDFTLKISRVEAEDVGVYYCSQSTHLPFTFG

QGTKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

Second subunit nucleotide sequence (SEQ ID NO: 61) of fusion protein BY19.3(κ, IgG4):
CTCGAGGCCACCATGGAGACCGACACACTCCTCCTGTGGGTGCTGCTGCTCTGGGTGCC

AGGCAGCACCGGCCAGGTGCAGCTCGTGCAGAGCGGCGCCGAGGTGAAGAAGCCCGG

CTCTTCTGTGAAGGTGTCTTGCAAGGCTTCCGGCTACTCTTTCACCGACTACCACATTC

ACTGGGTGCGCCAGGCTCCTGGCCAGGGCCTTGAGTGGATGGGCGTGATTAACCCTAT

GTACGGCACAACAGACTACAACCAGCGGTTCAAGGGCAGAGTGACCATTACAGCCGA

CGAGTCCACATCCACCGCTTACATGGAGCTGTCCTCCCTGCGTTCTGAGGACACTGCTG

TGTACTACTGCGCTAGATACGACTACTTCACCGGCACTGGCGTGTACTGGGGCCAGGG

CACACTCGTGACCGTGTCTAGCGCATCAACAAAGGGCCCATCTGTGTTCCCACTCGCCC

CATGCTCCCGCTCCACCTCCGAGTCCACCGCCGCCCTGGGCTGCCTGGTGAAGGACTAC

TTCCCTGAGCCTGTGACCGTGTCCTGGAACTCCGGCGCCCTGACCTCCGGCGTGCACAC

CTTCCCTGCCGTGCTGCAGTCCTCCGGCCTGTACTCCCTGTCCTCCGTGGTGACCGTGCC

TTCCTCCTCCCTGGGCACCAAGACCTACACCTGCAACGTGGACCACAAGCCTTCCAACA

CCAAGGTGGACAAGCGCGTGGAGTCCAAGTACGGCCCTCCTTGCCCTCCTTGCCCTGCC

CCTGAGTTCCTGGGCGGCCCTTCCGTGTTCCTGTTCCCTCCTAAGCCTAAGGACACCCT

GATGATCTCCCGCACCCCTGAGGTGACCTGCGTGGTGGTGGACGTGTCCCAGGAGGAC

CCTGAGGTGCAGTTCAACTGGTACGTGGACGGCGTGGAGGTGCACAACGCCAAGACCA

AGCCTCGCGAGGAGCAGTTCAACTCCACCTACCGCGTGGTGTCCGTGCTGACCGTGCT

GCACCAGGACTGGCTGAACGGCAAGGAGTACAAGTGCAAGGTGTCCAACAAGGGCCT

GCCTTCCTCCATCGAGAAGACCATCTCCAAGGCCAAGGGCCAGCCTCGCGAGCCTCAG

GTGTACACCCTGCCTCCTTCCCAGGAGGAGATGACCAAGAACCAGGTGTCCCTGACCT

GCCTGGTGAAGGGCTTCTACCCTTCCGACATCGCCGTGGAGTGGGAGTCCAACGGCCA

GCCTGAGAACAACTACAAGACCACCCCTCCTGTGCTGGACTCCGACGGCTCCTTCTTCC

TGTACTCCCGCCTGACCGTGGACAAGTCCCGCTGGCAGGAGGGCAACGTGTTCTCCTG

CTCCGTGATGCACGAGGCCCTGCACAACCACTACACCCAGAAGTCCCTGTCCCTGTCCC

TGGGCGGCGGAGGATCTGGCGGCGGAGGCAGTGGAGGCGGCGGAAGCCTGCCCGCAC

AAGTGGCCTTCACCCCCTACGCCCCAGAGCCCGGCTCTACTTGTAGGCTGAGGGAGTA

CTACGACCAGACCGCCCAGATGTGCTGCTCCAAGTGTAGCCCCGGACAGCACGCCAAG

GTGTTCTGTACAAAGACCTCCGACACCGTGTGCGACTCCTGCGAGGACTCCACCTACAC

CCAGCTGTGGAACTGGGTGCCCGAGTGCCTGTCCTGCGGCTCCAGGTGCTCCTCTGACC

AGGTCGAGACCCAAGCCTGTACCAGGGAGCAGAACAGGATCTGCACTTGCAGGCCAG

GCTGGTATTGCGCCCTGTCCAAGCAGGAAGGCTGCAGGCTGTGCGCCCCACTGAGGAA

ATGTAGGCCTGGGTTCGGCGTGGCTAGGCCCGGAACCGAGACTTCCGACGTGGTGTGC

AAGCCCTGTGCCCCTGGCACCTTTTCCAACACCACCTCCTCCACCGACATCTGTAGGCC

ACACCAGATTTAAGAATTC

Second subunit amino acid sequence (SEQ ID NO: 62) of fusion protein BY19.3(κ, IgG4):
METDTLLLWVLLLWVPGSTGQVQLVQSGAEVKKPGSSVKVSCKASGYSFTDYHIHWVRQ

APGQGLEWMGVINPMYGTTDYNQRFKGRVTITADESTSTAYMELSSLRSEDTAVYYCARY

DYFTGTGVYWGQGTLVTVSSASTKGPSVFPLAPCSRSTSESTAALGCLVKDYFPEPVTVSW

NSGALTSGVHTFPAVLQSSGLYSLSSVVTVPSSSLGTKTYTCNVDHKPSNTKVDKRVESKY

GPPCPPCPAPEFLGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAKGQP

REPQVYTLPPSQEEMTKNQVSLTCLVKGFYPSDIAVEWESNGQPENNYKTTPPVLDSDGSF

FLYSRLTVDKSRWQEGNVFSCSVMHEALHNHYTQKSLSLSLGGGGSGGGGSGGGGSLPA

QVAFTPYAPEPGSTCRLREYYDQTAQMCCSKCSPGQHAKVFCTKTSDTVCDSCEDSTYTQ

LWNWVPECLSCGSRCSSDQVETQACTREQNRICTCRPGWYCALSKQEGCRLCAPLRKCRP

GFGVARPGTETSDVVCKPCAPGTFSNTTSSTDICRPHQI

First subunit nucleotide sequence (SEQ ID NO: 63) of fusion protein BY19.5(κ, IgG1):
TCTAGAGCCACCATGGAGACCGACACCCTCCTCCTGTGGGTGCTGCTGCTGTGGGTGCC

CGGCTCTACCGGCGAGATCGTGCTGACTCAGTCTCCAGGCACACTGTCTCTGTCCCCTG

GCGAGCGCGCTACACTGTCTTGCAGAGCTTCTCAGTCCGTGAGCAGCTCTTACCTCGCT

TGGTATCAGCAGAAGCCTGGCCAGGCCCCTAGACTCCTGATATACGGCGCCTCGTCTA

GGGCTACAGGCATTCCCGACAGGTTCTCCGGCTCTGGCAGCGGCACCGACTTCACACT

CACTATTAGCCGCCTAGAACCTGAGGACTTCGCCGTGTACTACTGCCAGCAGTACGGCT

CTAGCCCATGCACATTCGGCCAGGGCACAAGACTTGAGATCAAGAGGACCGTGGCCGC

CCCCAGCGTGTTCATCTTCCCTCCCAGCGACGAGCAGCTGAAGTCTGGCACCGCCAgCG

TGGTGTGCCTGCTGAACAACTTCTACCCCCGCGAGGCCAAGGTGCAGTGGAAGGTGGA

CAACGCCCTGCAgAGCGGCAACAGCCAGGAGAGCGTGACCGAGCAGGACTCCAAGGA

CAGCACCTACAGCCTGAGCAGCACCCTGACCCTGAGCAAGGCCGACTACGAGAAGCAC

AAGGTGTACGCCTGCGAGGTGACCCACCAGGGACTGTCTAGCCCCGTGACCAAGAGCT

TCAACCGGGGCGAGTGCTAAGTCGAC

-continued

First subunit amino acid sequence (SEQ ID NO: 64) of fusion protein BY19.5(κ, IgG1):
METDTLLLWVLLLWVPGSTGEIVLTQSPGTLSLSPGERATLSCRASQSVSSSYLAWYQQKP

GQAPRLLIYGASSRATGIPDRFSGSGSGTDFTLTISRLEPEDFAVYYCQQYGSSPCTFGQGTR

LEIKRTVAAPSVFIFPPSDEQLKSGTASVVCLLNNFYPREAKVQWKVDNALQSGNSQESVT

EQDSKDSTYSLSSTLTLSKADYEKHKVYACEVTHQGLSSPVTKSFNRGEC

Second subunit nucleotide sequence (SEQ ID NO: 65) of fusion protein BY19.5(κ, IgG1):
CTCGAGGCCACCATGGAGACCGACACACTCCTCCTGTGGGTGCTGCTGCTCTGGGTGCC

AGGCAGCACCGGCGAGGTGCAGTTGGTGGAGTCCGGCGGCGGCCTCGTGCAGCCAGG

CGGCTCCCTGAGACTGTCTTGCGCCGCTTCCGGCTTCACTTTCTCTAACTACTGGATGA

ACTGGGTGAGACAGGCTCCAGGCAAGGGCCTTGAGTGGGTGGCCGCTATCAACCAGGA

CGGCTCCGAGAAGTACTATGTGGGCTCTGTGAAGGGCAGATTCACAATTAGCCGCGAC

AACGCTAAGAACAGCCTGTACTTACAGATGAACTCTCTCAGAGTGGAGGACACAGCTG

TGTACTACTGCGTGCGGGACTACTACGACATCCTGACCGACTACTACATTCACTACTGG

TACTTCGACCTCTGGGGCAGAGGCACTCTGGTCACCGTGAGCTCCGCCAGCACCAAGG

GCCCCAGCGTCTTCCCACTGGCTCCTTCCTCTAAAAGCACTAGCGGAGGGACCGCAGC

CCTGGGCTGTCTGGTGAAAGACTACTTCCCCGAGCCCGTGACCGTCTCCTGGAACTCTG

GAGCCCTGACCTCCGGGGTGCACACCTTTCCCGCCGTGCTGCAGTCTTCTGGACTGTAC

TCCCTGTCCTCCGTCGTGACTGTGCCCAGCTCCTCCCTGGGAACTCAGACATACATCTG

CAACGTGAACCACAAGCCTTCCAACACAAAGGTGGACAAGAGAGTCGAGCCCAAGAG

CTGTGATAAGACCCATACATGTCCCCCATGCCCCGCTCCAGAACTGCTGGGCGGACCTT

CCGTGTTTCTGTTCCCACCCAAACCAAAGGACACACTGATGATCAGCAGAACCCCTGA

GGTGACTTGCGTGGTCGTGGACGTGAGCCATGAGGACCCCGAGGTGAAGTTCAACTGG

TATGTGGATGGCGTGGAAGTGCATAATGCCAAGACAAAACCTAGGGAAGAGCAGTAC

AACAGCACCTACAGGGTGGTGAGCGTGCTGACCGTGCTGCACCAGGATTGGCTGAACG

GCAAGGAATACAAGTGCAAGGTGTCCAATAAGGCTCTGCCTGCACCTATCGAGAAGAC

CATCAGCAAAGCCAAGGGCCAACCCAGAGAGCCTCAAGTCTACACCCTGCCCCCAAGC

AGGGAGGAGATGACCAAAAATCAAGTGAGCCTGACATGCCTGGTCAAAGGCTTCTACC

CTAGCGACATCGCCGTGGAGTGGGAGAGCAATGGCCAGCCTGAGAACAACTACAAGA

CCACTCCCCCCGTCCTGGATAGCGACGGCAGCTTCTTCCTGTACTCCAAACTGACAGTC

GATAAAAGCAGGTGGCAGCAAGGCAATGTCTTTAGCTGTAGCGTGATGCACGAGGCCC

TGCATAACCACTACACTCAAAAGTCCCTGTCCCTGAGCCCCGGAGGCGGAGGATCTGG

CGGCGGAGGCAGTGGAGGCGGCGGAAGCCTGCCTGCTCAGGTGGCATTCACCCCATAC

GCTCCTGAGCCTGGCTCAACTTGTAGGCTGAGAGAGTACTACGACCAGACCGCCCAGA

TGTGCTGTTCCAAGTGCAGTCCTGGACAGCACGCTAAGGTGTTTTGCACAAAGACTTCC

GATACCGTGTGCGATAGTTGTGAGGACAGTACTTACACTCAGCTGTGGAATTGGGTGC

CAGAGTGTCTCTCTTGCGGCAGTAGATGTTCTTCCGATCAGGTCGAGACACAGGCTTGC

ACTCGCGAGCAGAATCGCATTTGCACATGTCGGCCAGGATGGTACTGCGCTCTGTCTA

AGCAGGAGGGCTGTAGACTCTGCGCCCCTCTCCGCAAGTGCCGCCCCGGATTCGGCGT

CGCACGGCCCGGAACCGAGACTAGCGACGTCGTCTGCAAGCCATGCGCTCCCGGAACC

TTTAGTAATACAACATCTTCTACTGATATTTGTAGGCCTCACCAGATTTGTAACGTGGT

GGCAATTCCTGGAAATGCCTCTATGGACGCCGTGTGTACATCTACATCCCCAACTAGAA

GTATGGCTCCCGGCGCCGTCCACCTCCCTCAGCCCGTGAGTACTCGGAGTCAGCACACT

CAGCCAACACCCGAGCCATCTACCGCACCTTCTACCTCTTTTCTGCTCCCTATGGGACC

TAGTCCACCAGCTGAGGGTAGTACTGGCGACTAAGAATTC

Second subunit amino acid sequence (SEQ ID NO: 66) of fusion protein BY19.5(κ, IgG1):
METDTLLLWVLLLWVPGSTGEVQLVESGGGLVQPGGSLRLSCAASGFTFSNYWMNWVRQ

APGKGLEWVAAINQDGSEKYYVGSVKGRFTISRDNAKNSLYLQMNSLRVEDTAVYYCVR

DYYDILTDYYIHYWYFDLWGRGTLVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPSNTKV

DKRVEPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALPAPI

EKTISKAKGQPREPQVYTLPPSREEMTKNQVSLTCLVKGFYPSDIAVEWESNGQPENNYKT

TPPVLDSDGSFFLYSKLTVDKSRWQQGNVFSCSVMHEALHNHYTQKSLSLSPGGGGSGGG

GSGGGGSLPAQVAFTPYAPEPGSTCRLREYYDQTAQMCCSKCSPGQHAKVFCTKTSDTVC

DSCEDSTYTQLWNWVPECLSCGSRCSSDQVETQACTREQNRICTCRPGWYCALSKQEGCR

LCAPLRKCRPGFGVARPGTETSDVVCKPCAPGTFSNTTSSTDICRPHQICNVVAIPGNASMD

First subunit nucleotide sequence (SEQ ID NO: 67) of fusion protein BY19.6(κ, IgG1):
TCTAGAGCCACCATGGAGACCGACACCCTCCTCCTGTGGGTGCTGCTGCTGTGGGTGCC

CGGCTCTACCGGCGACATCGTGATGACTCAGACACCACTGAGCCTGTCTGTGACCCCA

GGCCAGCCCGCTTCGATTTCTTGCCGGTCCTCTCGCAGCCTGGTGCACTCTAGGGGCAA

CACATACCTCCACTGGTATCTACAGAAGCCCGGCCAGTCCCCTCAGCTGCTGATCTACA

AGGTGTCTAACAGGTTCATTGGCGTGCCCGACCGCTTCTCCGGCTCTGGCAGCGGCACC

GACTTCACACTCAAGATTAGCAGAGTGGAGGCTGAGGACGTGGGCGTGTACTACTGCT

CTCAGTCTACCCACCTCCCTTTCACATTCGGCCAGGGCACAAAGGTGGAGATCAAGCG

GACCGTGGCCGCCCCCATCCGTGTTCATTTTCCCACCTTCCGACGAGCAGCTGAAGTCTG

GCACCGCCAGCGTGGTGTGCCTGCTGAACAACTTCTACCCCCGCGAGGCCAAGGTGCA

GTGGAAGGTGGACAACGCCCTGCAGAGCGGCAACAGCCAGGAGAGCGTGACCGAGCA

GGACTCCAAGGACAGCACCTACAGCCTGAGCAGCACCCTGACCCTGAGCAAGGCCGAC

TACGAGAAGCACAAGGTGTACGCCTGCGAGGTGACCCACCAGGGACTGTCTAGCCCCG

TGACCAAGAGCTTCAACCGGGGCGAGTGCTAAGAATT GTCGAC

First subunit amino acid sequence (SEQ ID NO: 68 = SEQ ID NO: 27) of fusion protein BY19.6(κ, IgG1):
METDTLLLWVLLLWVPGSTGDIVMTQTPLSLSVTPGQPASISCRSSRSLVHSRGNTYLHWY

LQKPGQSPQLLIYKVSNRFIGVPDRFSGSGSGTDFTLKISRVEAEDVGVYYCSQSTHLPFTFG

QGTKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

Second subunit nucleotide sequence (SEQ ID NO: 69) of fusion protein BY19.6 (κ, IgG1):
CTCGAGGCCACCATGGAGACCGACACACTCCTCCTGTGGGTGCTGCTGCTCTGGGTGCC

AGGCAGCACCGGCCTGCCCGCACAAGTGGCCTTCACCCCCTACGCCCCAGAGCCCGGC

TCTACTTGTAGGCTGAGGGAGTACTACGACCAGACCGCCCAGATGTGCTGCTCCAAGT

GTAGCCCCGGACAGCACGCCAAGGTGTTCTGTACAAAGACCTCCGACACCGTGTGCGA

CTCCTGCGAGGACTCCACCTACACCCAGCTGTGGAACTGGGTGCCCGAGTGCCTGTCCT

GCGGCTCCAGGTGCTCCTCTGACCAGGTCGAGACCCAAGCCTGTACCAGGGAGCAGAA

CAGGATCTGCACTTGCAGGCCAGGCTGGTATTGCGCCCTGTCCAAGCAGGAAGGCTGC

AGGCTGTGCGCCCCACTGAGGAAATGTAGGCCTGGGTTCGGCGTGGCTAGGCCCGGAA

-continued

```
CCGAGACTTCCGACGTGGTGTGCAAGCCCTGTGCCCCTGGCACCTTTTCCAACACCACC

TCCTCCACCGACATCTGTAGGCCACACCAGATTGACAAGCGCGTGGAGTCCAAGTACG

GCCCTCCTTGCCCTCCTTGCCCTGCCCCTGAGTTCCTGGGCGGCCCTTCCGTGTTCCTGT

TCCCTCCTAAGCCTAAGGACACCCTGATGATCTCCCGCACCCCTGAGGTGACCTGCGTG

GTGGTGGACGTGTCCCAGGAGGACCCTGAGGTGCAGTTCAACTGGTACGTGGACGGCG

TGGAGGTGCACAACGCCAAGACCAAGCCTCGCGAGGAGCAGTTCAACTCCACCTACCG

CGTGGTGTCCGTGCTGACCGTGCTGCACCAGGACTGGCTGAACGGCAAGGAGTACAAG

TGCAAGGTGTCCAACAAGGGCCTGCCTTCCTCCATCGAGAAGACCATCTCCAAGGCCA

AGGGCCAGCCTCGCGAGCCTCAGGTGTACACCCTGCCTCCTTCCCAGGAGGAGATGAC

CAAGAACCAGGTGTCCCTGACCTGCCTGGTGAAGGGCTTCTACCCTTCCGACATCGCCG

TGGAGTGGGAGTCCAACGGCCAGCCTGAGAACAACTACAAGACCACCCCTCCTGTGCT

GGACTCCGACGGCTCCTTCTTCCTGTACTCCCGCCTGACCGTGGACAAGTCCCGCTGGC

AGGAGGGCAACGTGTTCTCCTGCTCCGTGATGCACGAGGCCCTGCACAACCACTACAC

CCAGAAGTCCCTGTCCCTGTCCCTGGGCGGCGGAGGATCTGGCGGCGGAGGCAGTGGA

GGCGGCGGAAGCCAGGTGCAGCTCGTGCAGAGCGGCGCCGAGGTGAAGAAGCCCGGC

TCTTCTGTGAAGGTGTCTTGCAAGGCTTCCGGCTACTCTTTCACCGACTACCACATTCA

CTGGGTGCGCCAGGCTCCTGGCCAGGGCCTTGAGTGGATGGGCGTGATTAACCCTATG

TACGGCACAACAGACTACAACCAGCGGTTCAAGGGCAGAGTGACCATTACAGCCGAC

GAGTCCACATCCACCGCTTACATGGAGCTGTCCTCCCTGCGTTCTGAGGACACTGCTGT

GTACTACTGCGCTAGATACGACTACTTCACCGGCACTGGCGTGTACTGGGGCCAGGGC

ACACTCGTGACCGTGTCTAGCGCATCAACAAAGGGCCCATCTGTGTTCCCACTCGCCCC

ATGCTCCCGCTCCACCTCCGAGTCCACCGCCGCCCTGGGCTGCCTGGTGAAGGACTACT

TCCCTGAGCCTGTGACCGTGTCCTGGAACTCCGGCGCCCTGACCTCCGGCGTGCACACC

TTCCCTGCCGTGCTGCAGTCCTCCGGCCTGTACTCCCTGTCCTCCGTGGTGACCGTGCCT

TCCTCCTCCCTGGGCACCAAGACCTACACCTGCAACGTGGACCACAAGCCTTCCAACA

CCAAGGTGGACAAGCGCGTGGAGTCCTAAGAATTC
```

Second subunit amino acid sequence (SEQ ID NO: 70) of fusion protein BY19.6(κ, IgG1):
METDTLLLWVLLLWVPGSTGLPAQVAFTPYAPEPGSTCRLREYYDQTAQMCCSKCSPGQH

AKVFCTKTSDTVCDSCEDSTYTQLWNWVPECLSCGSRCSSDQVETQACTREQNRICTCRP

GWYCALSKQEGCRLCAPLRKCRPGFGVARPGTETSDVVCKPCAPGTFSNTTSSTDICRPHQ

IDKRVESKYGPPCPPCPAPEFLGGPSVFLFPPKPKDTLMISRTPEVTCVVVDVSQEDPEVQFN

WYVDGVEVHNAKTKPREEQFNSTYRVVSVLTVLHQDWLNGKEYKCKVSNKGLPSSIEKTI

SKAKGQPREPQVYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGGGGSGGGGSGG

GGSQVQLVQSGAEVKKPGSSVKVSCKASGYSFTDYHIHWVRQAPGQGLEWMGVINPMYG

TTDYNQRFKGRVTITADESTSTAYMELSSLRSEDTAVYYCARYDYFTGTGVYWGQGTLVT

VSSASTKGPSVFPLAPCSRSTSESTAALGCLVKDYFPEPVTVSWNSGALTSGVHTFPAVLQS

SGLYSLSSVVTVPSSSLGTKTYTCNVDHKPSNTKVDKRVES

Second subunit nucleotide sequence (SEQ ID NO: 71) of fusion protein BY19.7(κ, IgG1):
TCTAGAGCCACCATGGAGACCGACACACTCCTCCTGTGGGTGCTGCTGCTCTGGGTGCC

AGGCAGCACCGGCCAGGTGCAGCTCGTGCAGAGCGGCGCCGAGGTGAAGAAGCCCGG

-continued
CTCTTCTGTGAAGGTGTCTTGCAAGGCTTCCGGCTACTCTTTCACCGACTACCACATTC

ACTGGGTGCGCCAGGCTCCTGGCCAGGGCCTTGAGTGGATGGGCGTGATTAACCCTAT

GTACGGCACAACAGACTACAACCAGCGGTTCAAGGGCAGAGTGACCATTACAGCCGA

CGAGTCCACATCCACCGCTTACATGGAGCTGTCCTCCCTGCGTTCTGAGGACACTGCTG

TGTACTACTGCGCTAGATACGACTACTTCACCGGCACTGGCGTGTACTGGGGCCAGGG

CACACTCGTGACCGTGTCTAGCGCATCAACAAAGGGCCCATCTGTGTTCCCACTCGCCC

CATGCTCCCGCTCCACCTCCGAGTCCACCGCCGCCCTGGGCTGCCTGGTGAAGGACTAC

TTCCCTGAGCCTGTGACCGTGTCCTGGAACTCCGGCGCCCTGACCTCCGGCGTGCACAC

CTTCCCTGCCGTGCTGCAGTCCTCCGGCCTGTACTCCCTGTCCTCCGTGGTGACCGTGCC

TTCCTCCTCCCTGGGCACCAAGACCTACACCTGCAACGTGGACCACAAGCCTTCCAACA

CCAAGGTGGACAAGCGCGTGGAGTCCTAAGTCGAC

Second subunit amino acid sequence (SEQ ID NO: 72) of fusion protein BY19.7(κ, IgG1):
<u>METDTLLLWVLLLWVPGSTG</u>QVQLVQSGAEVKKPGSSVKVSCKASGYSFTDYHIHWVRQ

APGQGLEWMGVINPMYGTTDYNQRFKGRVTITADESTSTAYMELSSLRSEDTAVYYCARY

DYFTGTGVYWGQGTLVTVSSASTKGPSVFPLAPCSRSTSESTAALGCLVKDYFPEPVTVSW

NSGALTSGVHTFPAVLQSSGLYSLSSVVTVPSSSLGTKTYTCNVDHKPSNTKVDKRVES

First subunit nucleotide sequence (SEQ ID NO: 73) of fusion protein BY19.7(κ, IgG1):
CTCGAGGCCACCATGGAGACCGACACACTCCTCCTGTGGGTGCTGCTGCTCTGGGTGCC

AGGCAGCACCGGCCTGCCCGCACAAGTGGCCTTCACCCCCTACGCCCCAGAGCCCGGC

TCTACTTGTAGGCTGAGGGAGTACTACGACCAGACCGCCCAGATGTGCTGCTCCAAGT

GTAGCCCCGGACAGCACGCCAAGGTGTTCTGTACAAAGACCTCCGACACCGTGTGCGA

CTCCTGCGAGGACTCCACCTACACCCAGCTGTGGAACTGGGTGCCCGAGTGCCTGTCCT

GCGGCTCCAGGTGCTCCTCTGACCAGGTCGAGACCCAAGCCTGTACCAGGGAGCAGAA

CAGGATCTGCACTTGCAGGCCAGGCTGGTATTGCGCCCTGTCCAAGCAGGAAGGCTGC

AGGCTGTGCGCCCCACTGAGGAAATGTAGGCCTGGGTTCGGCGTGGCTAGGCCCGGAA

CCGAGACTTCCGACGTGGTGTGCAAGCCCTGTGCCCCTGGCACCTTTTCCAACACCACC

TCCTCCACCGACATCTGTAGGCCACACCAGATTGACAAGCGCGTGGAGTCCAAGTACG

GCCCTCCTTGCCCTCCTTGCCCTGCCCCTGAGTTCCTGGGCGGCCCTTCCGTGTTCCTGT

TCCCTCCTAAGCCTAAGGACACCCTGATGATCTCCCGCACCCCTGAGGTGACCTGCGTG

GTGGTGGACGTGTCCCAGGAGGACCCTGAGGTGCAGTTCAACTGGTACGTGGACGGCG

TGGAGGTGCACAACGCCAAGACCAAGCCTCGCGAGGAGCAGTTCAACTCCACCTACCG

CGTGGTGTCCGTGCTGACCGTGCTGCACCAGGACTGGCTGAACGGCAAGGAGTACAAG

TGCAAGGTGTCCAACAAGGGCCTGCCTTCCTCCATCGAGAAGACCATCTCCAAGGCCA

AGGGCCAGCCTCGCGAGCCTCAGGTGTACACCCTGCCTCCTTCCCAGGAGGAGATGAC

CAAGAACCAGGTGTCCCTGACCTGCCTGGTGAAGGGCTTCTACCCTTCCGACATCGCCG

TGGAGTGGGAGTCCAACGGCCAGCCTGAGAACAACTACAAGACCACCCCTCCTGTGCT

GGACTCCGACGGCTCCTTCTTCCTGTACTCCCGCCTGACCGTGGACAAGTCCCGCTGGC

AGGAGGGCAACGTGTTCTCCTGCTCCGTGATGCACGAGGCCCTGCACAACCACTACAC

CCAGAAGTCCCTGTCCCTGTCCCTGGGCGGCGGAGGATCTGGCGGCGGAGGCAGTGGA

GGCGGCGGAAGCGACATCGTGATGACTCAGACACCACTGAGCCTGTCTGTGACCCCAG

GCCAGCCCGCTTCGATTTCTTGCCGGTCCTCTCGCAGCCTGGTGCACTCTAGGGGCAAC

ACATACCTCCACTGGTATCTACAGAAGCCCGGCCAGTCCCCTCAGCTGCTGATCTACAA

-continued

```
GGTGTCTAACAGGTTCATTGGCGTGCCCGACCGCTTCTCCGGCTCTGGCAGCGGCACCG

ACTTCACACTCAAGATTAGCAGAGTGGAGGCTGAGGACGTGGGCGTGTACTACTGCTC

TCAGTCTACCCACCTCCCTTTCACATTCGGCCAGGGCACAAAGGTGGAGATCAAGCGG

ACCGTGGCCGCCCCATCCGTGTTCATTTTCCCACCTTCCGACGAGCAGCTGAAGTCTGG

CACCGCCAGCGTGGTGTGCCTGCTGAACAACTTCTACCCCCGCGAGGCCAAGGTGCAG

TGGAAGGTGGACAACGCCCTGCAGAGCGGCAACAGCCAGGAGAGCGTGACCGAGCAG

GACTCCAAGGACAGCACCTACAGCCTGAGCAGCACCCTGACCCTGAGCAAGGCCGACT

ACGAGAAGCACAAGGTGTACGCCTGCGAGGTGACCCACCAGGGACTGTCTAGCCCCGT

GACCAAGAGCTTCAACCGGGGCGAGTGCTAAGAATTC

First subunit amino acid sequence (SEQ ID NO: 74) of fusion protein BY19.7(κ, IgG1):
METDTLLLWVLLLWVPGSTGLPAQVAFTPYAPEPGSTCRLREYYDQTAQMCCSKCSPGQH

AKVFCTKTSDTVCDSCEDSTYTQLWNWVPECLSCGSRCSSDQVETQACTREQNRICTCRP

GWYCALSKQEGCRLCAPLRKCRPGFGVARPGTETSDVVCKPCAPGTFSNTTSSTDICRPHQ

IDKRVESKYGPPCPPCPAPEFLGGPSVFLFPPKPKDTLMISRTPEVTCVVVDVSQEDPEVQFN

WYVDGVEVHNAKTKPREEQFNSTYRVVSVLTVLHQDWLNGKEYKCKVSNKGLPSSIEKTI

SKAKGQPREPQVYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGGGGSGGGGSGG

GGSDIVMTQTPLSLSVTPGQPASISCRSSRSLVHSRGNTYLHWYLQKPGQSPQLLIYKVSNR

FIGVPDRFSGSGSGTDFTLKISRVEAEDVGVYYCSQSTHLPFTFGQGTKVEIKRTVAAPSVFI

FPPSDEQLKSGTASVVCLLNNFYPREAKVQWKVDNALQSGNSQESVTEQDSKDSTYSLSST

LTLSKADYEKHKVYACEVTHQGLSSPVTKSFNRGEC
```

Using the similar method as in Example 1(1) above, each of the nucleotides encoding the above first subunits (SEQ ID NOs: 59, 63, 67, 73) and a glutamine synthetase high-efficiency expression vector with dual expression cassettes (Chinese patent No. CN104195173B, obtained from Beijing Beyond Biotechnology Co., Ltd) were double digested with XbaI-SalI respectively and linked together. Then each of the XhoI-EcoRI double-digested second subunit encoding nucleotide (SEQ ID NO: 61, 65, 69, or 71) was respectively cloned into the expression vector previously linked with the corresponding nucleotide encoding the first subunit; or vice versa. After sequenced, the recombinant vectors were to be expressed. The expressed fusion proteins were named as fusion proteins BY19.3, BY19.5, BY19.6, BY19.7.

Example 2. Expression and Purification of Fusion Proteins (1) Transient Expression of Fusion Protein 293F cell (purchased from Invitrogen, catalog number: 11625-019) was suspended and cultured in serum-free CD 293 medium (purchased from Invitrogen, catalog number: 11913-019). Before transfection, the cultured cell was centrifuged to obtain a cell pellet, suspended and adjusted the cell concentration to $1 \times 10^6$ cells/ml in a fresh serum-free CD 293 medium, then placed in a shake flask. Taking 100 ml of cell suspension as an example, 250 ug of each of the recombinant expression vectors of fusion proteins BY19.3-BY19.7 prepared in Example 1 as plasmid DNA and 500 ug of polyethylenimine (PEI) (Sigma, catalog number: 408727) were added to 1 ml serum-free CD 293 medium and mixed well. After at room temperature for 8 minutes, the PEI/DNA suspension was added dropwise to the shake flask with 100 ml cell suspension. Mixed gently and placed at 37° C., 5% $CO_2$ for shaking (120 rpm) culture. 5 days later, the culture supernatant was collected.

In this way, antibodies BY19.3 (as control), BY19.4, BY19.5, BY19.6, BY19.7 were transiently expressed.

(2) Purification of the Expressed Proteins

The fusion protein in the culture supernatant collected in above Example 2 (1) was purified using 1 ml HiTrap MabSelect SuRe column (GE Healthcare Life Sciences, catalog number: 11-0034-93) equilibrated with pH 7.4 PBS solution. Briefly, the 1 ml HiTrap MabSelect SuRe column was equilibrated with 10 column volumes of PBS solution, pH 7.4 at a flow rate of 0.5m/min; the culture supernatant collected in above Example 2 (1) was filtered through a 0.45 m filter membrane and loaded onto the 1 ml HiTrap Mab-Select SuRe column equilibrated with PBS solution, pH 7.4; after loading the supernatant, the column was firstly washed with 5-10 column volumes of PBS solution, pH 7.4 at a flow rate of 0.5 ml/min. The expressed protein was then eluted with 100 mM citrate buffer (pH 4.0) at a flow rate of 0.5 ml/min. The fractions in the elution peak was collected, which contained the protein of interest.

Figure 2:
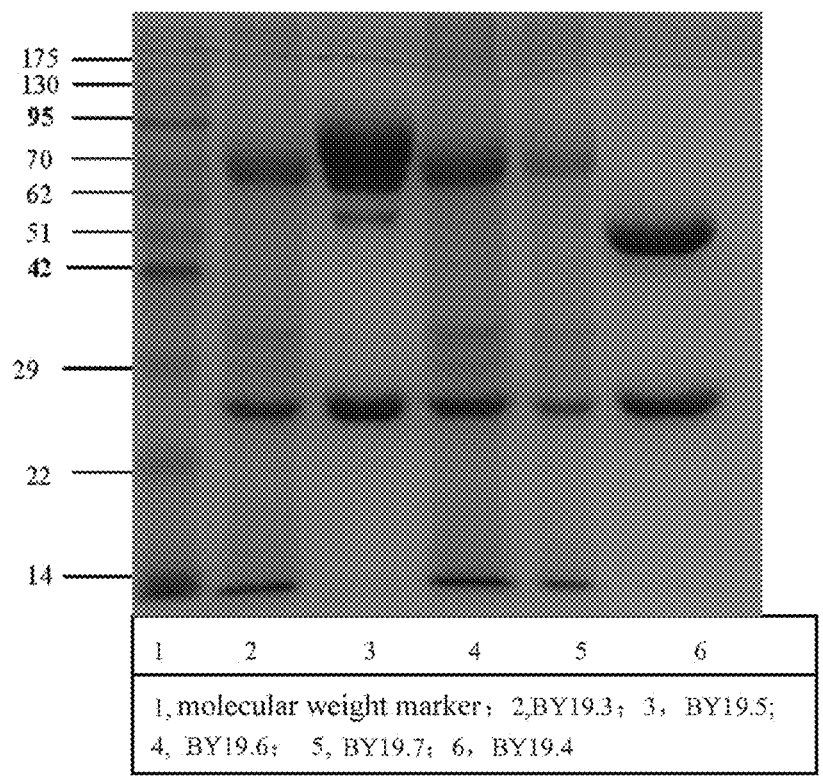
FIG. 2: shows a gel image of the fusion proteins of the present invention after SDS-PAGE electrophoresis in the presence of a reducing agent (5 mM 1,4-dithiothreitol) and Coomassie blue staining, wherein said fusion proteins are prepared and purified in Example 2. Lane 1: protein molecular weight marker; lane 2: fusion protein BY19.3; lane 3: fusion protein BY19.5; lane 4: fusion protein BY19.6; lane 5: fusion protein BY19.7; lane 6: fusion protein BY19.4.
Figure 3:
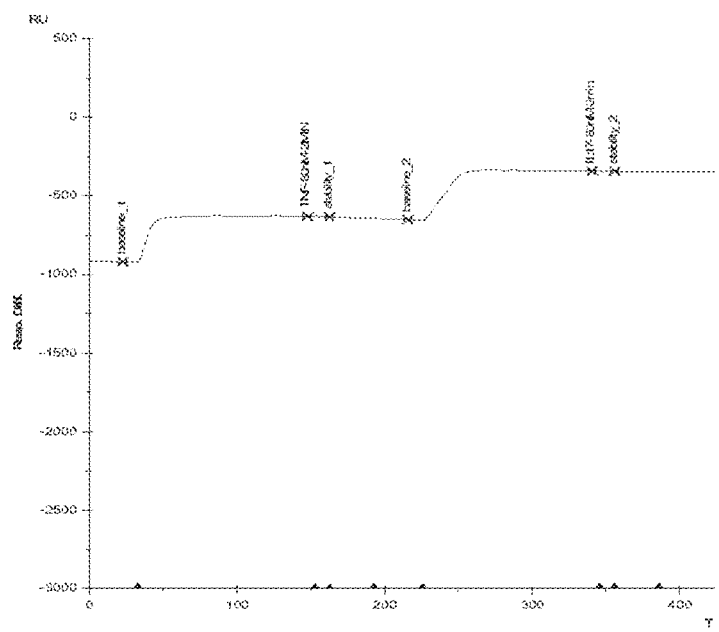
FIG. 3: shows that the anti-IL-17/TNFR fusion protein of the present invention binds TNF-α and IL-17 respectively, without interfering with each other.
Figure 4:
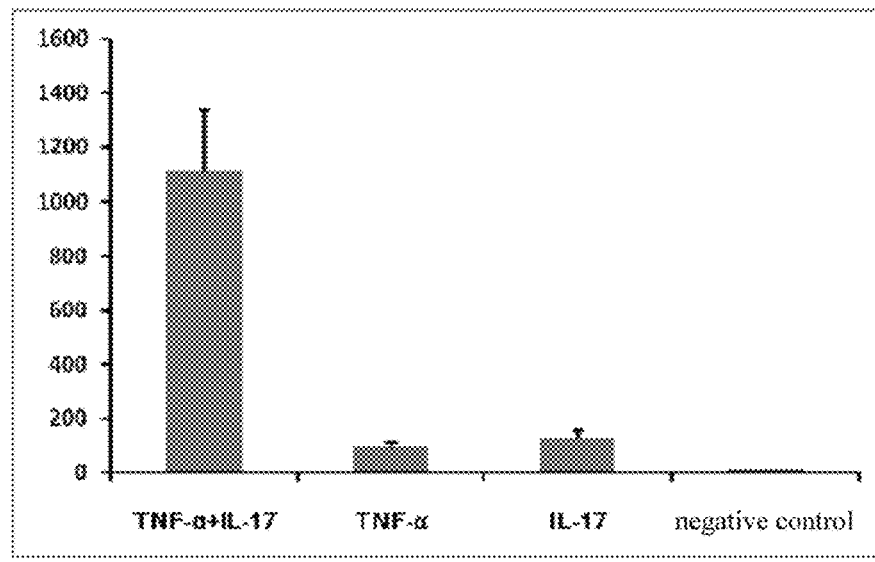
FIG. 4: shows the synergistic effect of TNF-α and IL-17 on CXCL1 expression.
Figure 5:
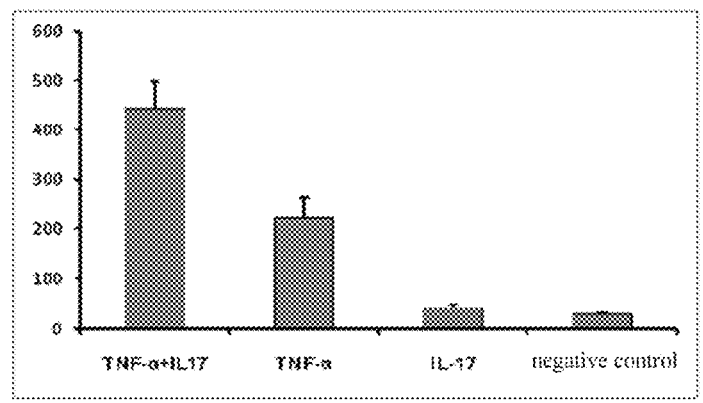
FIG. 5: shows the synergistic effect of TNF-α and IL-17 on IL-8 expression.
Figure 6:
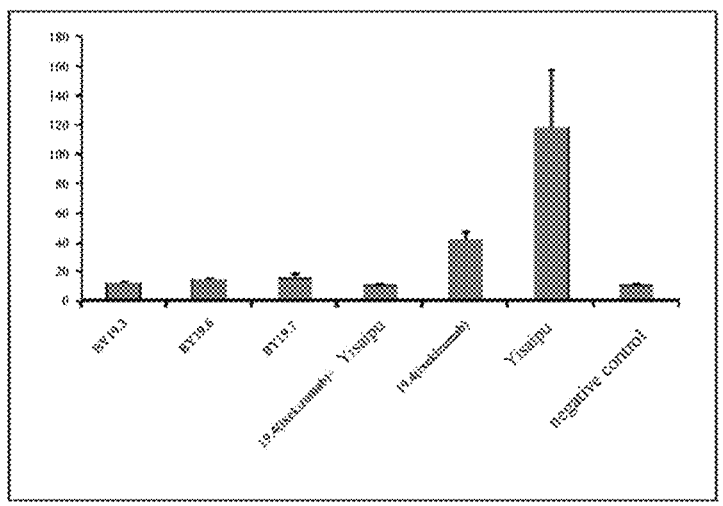
FIG. 6: shows the inhibitory effect of the anti-IL-17/TNFR fusion protein of the present invention on the expression of CXCL1.
Figure 7:
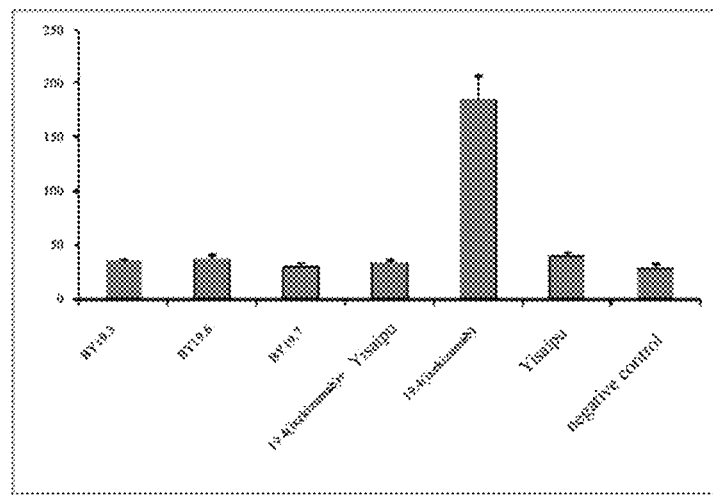
FIG. 7: shows the inhibitory effect of the anti-IL-17/TNFR fusion protein of the present invention on the expression of IL-8.

The purity and molecular weight of the fusion protein were analyzed by SDS-PAGE in the presence of a reducing agent (5 mM 1,4-dithiothreitol) and Coomassie blue staining. The result was shown in FIG. 2. The theoretical predicted and actual measured molecular weights were shown in Table 6. Due to the glycosylation of proteins in the eukaryotic expression system, the actual measured molecular weight was slightly larger than the theoretically predicted one.

TABLE 6

The molecular weights of the purified expressed proteins

| Protein name | Subunit | Theoretical predicted molecular weight (kDa) | Actual measured molecular weight (kDa) | (Nucleotide) SEQ ID NO | (Amino acid) SEQ ID NO |
|---|---|---|---|---|---|
| Fusion protein BY19.3 | first subunit | 23 | 25 | 59 | 60 |
| | second subunit | 68 | 75 | 61 | 62 |
| Fusion protein BY19.5 | first subunit | 23 | 25 | 63 | 64 |
| | second subunit | 76 | 83 | 65 | 66 |
| Fusion protein BY19.6 | first subunit | 23 | 25 | 67 | 68 |
| | second subunit | 68 | 75 | 69 | 70 |
| Fusion protein BY19.7 | second subunit | 23 | 75 | 71 | 72 |
| | first subunit | 68 | 25 | 73 | 74 |
| Antibody BY19.4 | first subunit | 23 | 25 | 26 | 27 |
| | second subunit | 48 | 50 | 28 | 29 |

Example 3. Using Biacore T100 to Determine the Affinities of the Fusion Protein of the Present Invention for TNF-α and IL-17

Surface plasmon resonance assay was performed on a BIAcore® T100 instrument (GE Healthcare Biosciences AB, Sweden) at 25° C.

First, anti-IgG antibody (GE Healthcare Life Sciences, catalog number: BR-1008-39) was covalently immobilized on the CM5 chip by amide coupling. Briefly, 60p1 N-ethyl-N'-(3-dimethylaminopropyl)carbodiimide hydrochloride (EDC) and 60p1 N-hydroxysuccinimide (NHS) were used to activate the CM5 chip. The anti-IgG antibody was diluted by adding 95 µl HBST (0.1 M HEPES, 1.5 M NaCl, pH7.4, supplemented with 0.005% Tween 20, filtered through 0.2 um filter) as dilution buffer, and covalently fixed on the CM5 chip by amide coupling, to generate a capture system of about 9000-14000 resonance units (RU). The CM5 chip was blocked with 120 µl ethanolamine.

Next, the fusion protein (BY19.3, BY19.5, BY19.6, BY19.7) and Yisaipu (TNFR2-Fc fusion protein, Shanghai CITIC Guojian Pharmaceutical Co., Ltd.) and the control antibody BY19.4 were diluted to 5 µg/ml, and injected at a flow rate of 10 µL/min for 2 minutes, respectively, so that the above-mentioned fusion proteins of the invention and antibody BY19.4 were bound to the anti-IgG antibody non-covalently through their respective Fc regions, thus captured on the CM5 chip, generating about 1600RU.

Recombinant human TNF-α (Sino Biological Inc., catalog number: 10602-HNAE) and recombinant human IL-17A Sino Biological Inc., catalog number: 12047-H07Y) as antigen for binding were prepared at concentration gradients of 7 nM, 22 nM, 66 nM, 200 nM, 600 nM. Binding was measured by injecting each concentration at a flow rate of 30 µl/min for 180 seconds, then a dissociation time of 600 seconds. The surface was regenerated by washing with 3 M MgCl$_2$ solution at a flow rate of 10 µL/min for 30 seconds. Data analysis was performed using BIA evaluation software (BIAevaluation 4.1 software, from GE Healthcare Biosciences AB, Sweden). The obtained affinity data was in Table 7 below.

TABLE 7

Binding of each protein to antigens

| Protein name | Antigen | ka (1/Ms) | kd (1/s) | KD (M) |
|---|---|---|---|---|
| fusion protein BY19.3 | TNF-α | 9.99E+06 | 4.77E-04 | 4.78E-11 |
| | IL-17A | 7.04E+06 | 7.67E-05 | 1.09E-11 |
| fusion protein BY19.5 | TNF-α | 3.76E+06 | 7.91E-04 | 2.11E-10 |
| | IL-17A | 9.83E+06 | 1.63E-04 | 1.66E-11 |
| Antibody BY19.4 | TNF-α | — | — | — |
| | IL-17A | 7.89E+06 | 6.79E-04 | 8.60E-11 |
| fusion protein BY19.6 | TNF-α | 4.58E+06 | 3.33E-05 | 7.27E-12 |
| | IL-17A | 6.21E+05 | 8.36E-04 | 1.35E-9 |
| fusion protein BY19.7 | TNF-α | 6.63E+06 | 4.81E-05 | 7.25E-12 |
| | IL-17A | 8.59E+04 | 7.52E-04 | 8.75E-9 |
| Yisaipu | TNF-α | 3.98E+06 | 2.67E-05 | 6.70E-12 |
| | IL-17A | — | — | — |

From the data shown in Table 7, the fusion proteins BY19.3 and BY19.5 of the present invention, with TNFR2 at the C-terminus, bound TNF-α and IL-17A with high affinity. Antibody BY19.4 did not bind TNF-α.

The fusion protein BY19.3 and antibody BY19.4 have the same N-terminal structure. Biacore results showed that the fusion protein BY19.3 and antibody BY19.4 bound IL-17A with similar affinity (with a difference less than 1 fold).

The C-terminus of the fusion protein BY19.5 was the full length of the extracellular domain of TNFR2, while the C-terminus of the fusion protein BY19.3 was the N-terminal fragment of CRD1-CRD2-CRD3-CRD4 (i.e. truncated TNFR2). The binding affinities of the two fusion proteins to TNF-α were similar (with a difference less than 1 fold). It suggested that the truncated form of TNFR2 which was easier to express and purify in the present invention did not affect the affinity with TNF-α.

The fusion proteins Yisaipu, BY19.6 and BY19.7, with TNFR2 at N-terminus, had a higher affinity for TNF-α (up to $10^{-12}$ M) as compared with those of BY19.3 and BY19.5. However, the fusion proteins BY19.6 and BY19.7 had a lower affinity for IL-17A ($10^{-9}$ M) as compared with those of BY19.4, BY19.3 and BY19.5. This may be due to the Fab structures in BY19.6 and BY19.7, and the affinity of the Fab structure to IL-17 is lower than that of the full-length antibody to IL-17.

Example 4. Using Biacore T100 to Determine the Binding Interaction Between Anti-IL-17/TNFR Fusion Protein and TNF-α & IL-17

The CM5 chip pretreatment was the same as in Example 3. The anti-IgG antibody (GE Healthcare Life Sciences, catalog number: BR-1008-39) was covalently fixed on the CM5 chip. The BY19.3 protein was diluted to 10 µg/ml, and injected at a flow rate of 10 µL/min for 1 minute.

The anti-IgG antibody captured the BY19.3 protein to produce 1600RU; Recombinant human TNF-α (Sino Biological Inc., catalog number: 10602-HNAE) was diluted to 80 nM, injected at a flow rate of 20 µL/min for 2 minutes. BY19.3 protein captured recombinant human TNF-α protein, produced 361RU, and reached saturation; then recombinant human IL-17A (Sino Biological Inc., catalog number: 12047-H07Y) was diluted to 80 nM, injected at a flow rate of 20 µL/min for 2 minutes, the chip having bound to TNF-α protein and reached saturation state can further capture recombinant human IL-17A protein, producing 290RU and reaching saturation. The surface was regenerated by washing with 3 M $MgCl_2$ solution at a flow rate of 10 μL/min for 2 minutes.

Results: Biacore T100 detection showed that BY19.3 protein captured by anti-IgG antibody could further bind to IL-17A and reach saturation after binding to TNF-α and reach saturation. It can be seen that with respect to BY19.3 protein, its binding to TNF-α and IL-17A does not interfere with each other.

Example 5 Synergy of TNF-α and IL-17 on the Expression of CXCL1 and IL-8

On the day before the experiment, the cultured HT-29 cells (purchased from the Cell Bank of the Chinese Academy of Sciences) were digested with trypsin-EDTA (purchased from Hyclone), and the digested product was collected. Centrifuge at 1500 rpm for 5 min, discard the supernatant; then resuspend the cells in 10 ml DMEM/F12 medium (purchased from Hyclone); count cell density; plant 96-well plate at 100 μl/well ($2×10^4$ cells/well); place in 37° C., 5% $CO_2$ incubator for overnight cultivation.

Recombinant human TNF-α (Sino Biological Inc., catalog number: 10602-HNAE) and recombinant human IL-17A (Sino Biological Inc., catalog number: 12047-H07Y) were freshly prepared on the day of the experiment, respectively. Add to the wells of HT-29 cells planted the day before, and set up 4 groups in the experiment: TNF-α, IL-17A, TNF-α plus IL-17A, and negative control groups, with 6 replicate wells in each group. The final concentration of recombinant human TNF-α is 300 μM, and the final concentration of recombinant human IL-17A is 10 nM, except for the negative control group. Place in an incubator (37° C., 5% $CO_2$) for 48 h.

After the cultivation, the supernatant was collected, and the expression levels of CXCL1 and IL-8 in the supernatant were detected using the CXCL1 ELISA kit (Cat. No: EK0722) and IL-8 kit (Cat. No: EK0413) from Boster Biological Technology co. Ltd.

Results:

The CXCL1 concentration in the negative control group was 10.6±0.6 μg/ml, in the TNF-α group was 93.2±22.8 μg/ml, in the IL-17 group was 127.2±30.8 μg/ml, and in the TNF-α plus IL-17 group was 1111.4±223.8 μg./ml. The concentrations of CXCL1 in TNF-α group, IL-17 group, and TNF-α plus IL-17 group were significantly higher than that of negative control group ($p<0.05$). The concentration of CXCL1 in TNF-α plus IL-17 group was significantly higher than those of TNF-α group and IL-17 group ($p<0.05$).

The IL-8 concentration in the negative control group was 29.0±3.6 μg/ml, in the TNF-α group was 223.0±41.3 μg/ml, in the IL-17 group was 43.7±5.2 μg/ml, and in the TNF-α plus IL-17 group was 442.9±56.9 μg/ml. The concentrations of IL-8 in the TNF-α group, IL-17 group, and TNF-α plus IL-17 group were significantly higher than that of negative control group ($p<0.05$). The concentration of IL-8 was significantly higher than those of TNF-α group and IL-17 group ($p<0.05$).

The above results showed that TNF-α alone or IL-17 alone can promote the secretions of CXCL1 and IL-8 by HT-29 cells, and coexistence of TNF-α and IL-17 can significantly and synergistically promote the secretions of CXCL1 and IL-8 by HT-29 cells.

TNF-α, IL-17, CXCL1, and IL-8 are all immune promoting factors that promote the activation of lymphocytes, the chemotaxis of neutrophil granulocytes, and the release of inflammatory factors, which are all closely related to autoimmune diseases. The occurrence and development are closely related. This provides a basis for the clinical development of the invention.

Example 6 Inhibition of Anti-IL-17/TNFR Fusion Protein on the Expression of CXCL1 and IL-8

The main reagents and materials of the experiment were basically the same as those in Example 5. The experiment set up 7 groups: BY19.3, BY19.6, BY19.7, BY19.4, Yisaipu (Shanghai CITIC Guojian Pharmaceutical Co., Ltd.), BY19.4+ Yisaipu, and negative control groups, with 6 replicate wells in each group. In each group, the final concentration of recombinant human TNF-α was 300 pM, the final concentration of recombinant human IL-17A was 10 nM, the final concentration of BY19.3, BY19.6, BY19.7, BY19.4, and Yisaipu was 40 nM, except for the negative control group. Mix and place the plate in an incubator (37° C., 5% $CO_2$) for 48 h.

After the cultivation, the supernatant was collected, and the expression levels of CXCL1 and IL-8 in the supernatant were detected using the CXCL1 ELISA kit (Cat. No: EK0722) and IL-8 kit (Cat. No: EK0413) from Boster Biological Technology co. Ltd.

Results:

In the presence of both TNF-α and IL-17A, the concentrations of CXCL1 in each group were: 12.4±0.6 μg/ml in BY19.3 group, 14.7±1.23 μg/ml in BY19.6, 15.4±3.22 in BY19.7, 10.7±0.58 μg/ml in BY19.4+ Yisaipu group, 42.1±5.6 μg/ml in BY19.4 (ixekizumab) group, 118.6±38.9 μg/ml in Yisaipu group, 10.6±0.6 μg/ml in negative control group. CXCL1 concentration in BY19.4 group or in Yisaipu group was significantly higher than that of negative control group ($p<0.05$). There was no significant difference in CXCL1 concentration among negative control group, BY19.3 group, BY19.6 group, BY19.7 group, and BY19.4+ Yisaipu group ($p>0.05$).

The above results showed that BY19.4 alone or Yisaipu alone, especially Yisaipu alone, had an inhibitory effect on CXCL1 expression not as good as those from BY19.3, BY19.6, and BY19.7 groups. Use of the combination of BY19.4 and Yisaipu, or use of BY19.3, BY19.6, or BY19.7, significantly inhibited the expression of CXCL1.

In the presence of both TNF-α and IL-17A, the concentrations of IL-8 in each group were: 35.9±1.9 μg/ml in BY19.3 group, 37.9±3.7 μg/ml in BY19.6 group, 30.6±2.9 μg/ml in BY19.7 group, 34.6±2.2 μg/ml in BY19.4+ Yisaipu group, 185.1±21.4 μg/ml in BY19.4 (ixekizumab) group, 40.3±3.4 μg/ml in Yisaipu group, 29.0±3.6 μg/ml in negative control group. BY19.3 group, BY19.6 group, BY19.7 group, and BY19.4+ Yisaipu group, and Yisaipu group had no significant difference in IL-8 concentration compared with the negative control group ($p>0.05$). The concentration of IL-8 in BY19.4 alone group was significantly higher than those in other groups ($p<0.05$).

The above results showed that when used alone, BY19.4 inhibited IL-8 expression, which was less than those of Yisaipu, BY19.4+ Yisaipu, or BY19.3, BY19.6, or BY19.7.

In summary, BY19.3, BY19.6, and BY19.7 had a significant inhibitory effect on the expression of CXCL1 and IL-8 in HT-29 cells, which were consistent with the effect of the combination of BY19.4 and Yisaipu, with the inhibition efficiency better than BY19.4 alone or Yisaipu alone group. It could be seen that the fusion protein of the present invention comprising anti-IL-17antibody and TNFR was potent for the treatment of rheumatoid arthritis, ankylosing spondylitis, psoriasis, and ulcerative colitis and other auto-immunity diseases.

Further, human anti-IL-17 antibody in the prior art, such as human IL-17scfv, cannot bind IL-17 in murine model. Neither human TNFR1 nor human TNFR2 can bind TNF-α in murine model. Therefore, the inventors cannot find a suitable animal to provide experimental data of the fusion protein of the present invention in animals. This is also an unresolved problem in the field.

What is claimed:

1. A fusion protein of an anti-IL-17 antibody and TNFR, wherein the fusion protein comprises or consists of (1) the first subunit of SEQ ID NO: 68 and the second subunit of SEQ ID NO: 70; or (2) the first subunit of SEQ ID NO: 74 and the second subunit of SEQ ID NO: 72.

2. A pharmaceutical composition comprising the fusion protein according to claim 1 and a pharmaceutically acceptable carrier.

* * * * *

```
                             SEQUENCE LISTING

<160> NUMBER OF SEQ ID NOS: 78

<210> SEQ ID NO 1
<211> LENGTH: 120
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Ile Leu Thr Asp Tyr Tyr Ile His Tyr Trp
            100                 105                 110

Tyr Phe Asp Leu Trp Gly Arg Gly
        115                 120

<210> SEQ ID NO 2
<211> LENGTH: 102
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Thr Phe Gly Gln Gly
            100

<210> SEQ ID NO 3
<211> LENGTH: 116
```

```
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 3

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Asn Trp Ser Ser Gly Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Gly Gly Phe Gly Glu Phe Tyr Trp Asn Phe Gly Leu
            100                 105                 110

Trp Gly Arg Gly
            115

<210> SEQ ID NO 4
<211> LENGTH: 102
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Thr Phe Gly Gly Gly
            100

<210> SEQ ID NO 5
<211> LENGTH: 118
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
```

```
                20                  25                  30

Asn Met Ala Trp Val Arg Gln Ala Pro Gly Lys Gly Leu Glu Trp Val
            35                  40                  45

Ala Thr Ile Thr Tyr Glu Gly Arg Asn Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gln Tyr Tyr Glu Gly Ser Ile Tyr Arg Leu Trp Phe
            100                 105                 110

Ala His Trp Gly Gln Gly
            115

<210> SEQ ID NO 6
<211> LENGTH: 101
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 6

Ala Ile Gln Leu Thr Gln Ser Pro Ser Leu Ser Ala Ser Val Gly
1               5                   10                  15

Asp Arg Val Thr Ile Thr Cys Arg Ala Asp Glu Ser Val Arg Thr Leu
            20                  25                  30

Met His Trp Tyr Gln Gln Lys Pro Gly Lys Ala Pro Lys Leu Leu Ile
            35                  40                  45

Tyr Leu Val Ser Asn Ser Glu Ile Gly Val Pro Asp Arg Phe Ser Gly
    50                  55                  60

Ser Gly Ser Gly Thr Asp Phe Arg Leu Thr Ile Ser Ser Leu Gln Pro
65                  70                  75                  80

Glu Asp Phe Ala Thr Tyr Tyr Cys Gln Gln Thr Trp Ser Asp Pro Trp
                85                  90                  95

Thr Phe Gly Gln Gly
            100

<210> SEQ ID NO 7
<211> LENGTH: 112
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
            35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
```

```
                    85                  90                  95
Ala Arg Tyr Asp Tyr Phe Thr Gly Thr Gly Val Tyr Trp Gly Gln Gly
                100                 105                 110
```

<210> SEQ ID NO 8
<211> LENGTH: 106
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 8

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly
            100                 105
```

<210> SEQ ID NO 9
<211> LENGTH: 115
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Thr Met Leu Trp Val Arg Gln Ala Pro Gly Lys Gly Leu Glu Trp Val
        35                  40                  45

Ala Ile Ile Lys Ser Gly Gly Ser Tyr Ser Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Asp Tyr Gly Ser Tyr Gly Ala Met Asp Tyr Trp
            100                 105                 110

Gly Gln Gly
        115
```

<210> SEQ ID NO 10
<211> LENGTH: 102
<212> TYPE: PRT
<213> ORGANISM: Artificial Sequence
<220> FEATURE:
<223> OTHER INFORMATION: Complementarity-determining region (CDR), experimentally altered human sequence

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Val Arg Ala Asn Arg Leu Val Asp Gly Val Pro Ser Arg Phe Ser Gly
50                  55                  60

Ser Gly Ser Gly Gln Asp Tyr Ser Leu Thr Ile Ser Ser Leu Gln Pro
65                  70                  75                  80

Glu Asp Phe Ala Thr Tyr Tyr Cys Leu Gln Tyr Asp Ala Phe Pro Pro
                85                  90                  95

Tyr Thr Phe Gly Gln Gly
            100

<210> SEQ ID NO 11
<211> LENGTH: 119
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 11

Glu Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Gly Gly Tyr
            20                  25                  30

Gly Ile Gly Trp Val Arg Gln Ala Pro Gly Gln Gly Leu Glu Trp Met
        35                  40                  45

Gly Gly Ile Thr Pro Phe Phe Gly Phe Ala Asp Tyr Ala Gln Lys Phe
50                  55                  60

Gln Gly Arg Val Thr Ile Thr Ala Asp Glu Ser Thr Thr Thr Ala Tyr
65                  70                  75                  80

Met Glu Leu Ser Gly Leu Thr Ser Asp Asp Thr Ala Val Tyr Tyr Cys
                85                  90                  95

Ala Arg Asp Pro Asn Glu Phe Trp Asn Gly Tyr Tyr Ser Thr His Asp
            100                 105                 110

Phe Asp Ser Trp Gly Gln Gly
        115

<210> SEQ ID NO 12
<211> LENGTH: 101
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 12

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Asp Ile Gly Ser Glu
            20                  25                  30

Leu His Trp Tyr Gln Gln Lys Pro Asp Gln Pro Pro Lys Leu Leu Ile
        35                  40                  45

```
Lys Tyr Ala Ser His Ser Thr Ser Gly Val Pro Ser Arg Phe Ser Gly
    50                  55                  60

Ser Gly Ser Gly Thr Asp Phe Thr Leu Thr Ile Asn Gly Leu Glu Ala
 65                  70                  75                  80

Glu Asp Ala Gly Thr Tyr Tyr Cys His Gln Thr Asp Ser Leu Pro Tyr
                 85                  90                  95

Thr Phe Gly Pro Gly
            100
```

<210> SEQ ID NO 13
<211> LENGTH: 116
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 13

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
             20                  25                  30

Glu Val His Trp Val Arg Gln Ala Pro Gly Gln Gly Leu Glu Trp Met
         35                  40                  45

Gly Val Ile Asp Pro Gly Thr Gly Gly Val Ala Tyr Asn Gln Lys Phe
     50                  55                  60

Glu Gly Arg Val Thr Met Thr Ala Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Thr Arg Tyr Ser Leu Phe Tyr Gly Ser Ser Pro Tyr Ala Met Asp Tyr
                100                 105                 110

Trp Gly Gln Gly
            115
```

<210> SEQ ID NO 14
<211> LENGTH: 100
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 14

```
Glu Ile Val Leu Thr Gln Ser Pro Asp Phe Gln Ser Val Thr Pro Lys
 1               5                  10                  15

Glu Lys Val Thr Ile Thr Cys Ser Ala Ser Ser Ser Val Asn Tyr Met
             20                  25                  30

His Trp Phe Gln Gln Lys Pro Asp Gln Ser Pro Lys Leu Trp Ile Tyr
         35                  40                  45

Arg Thr Ser Asn Leu Ala Ser Gly Val Pro Ser Arg Phe Ser Gly Ser
     50                  55                  60

Gly Ser Gly Thr Asp Tyr Thr Leu Thr Ile Asn Ser Leu Glu Ala Glu
 65                  70                  75                  80

Asp Ala Ala Thr Tyr Tyr Cys Gln Gln Arg Ser Ser Tyr Pro Trp Thr
                 85                  90                  95

Phe Gly Gln Gly
            100
```

```
<210> SEQ ID NO 15
<211> LENGTH: 120
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Met Ser Met Ser Asp Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Asp Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Tyr Tyr Asp Leu Ile Ser Asp Tyr Tyr Ile His Tyr Trp
            100                 105                 110

Tyr Phe Asp Leu Trp Gly Arg Gly
        115                 120

<210> SEQ ID NO 16
<211> LENGTH: 101
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 16

Asp Ile Gln Met Thr Gln Ser Pro Ser Ser Leu Ser Ala Ser Val Gly
1               5                   10                  15

Asp Arg Val Thr Ile His Cys Arg Ala Ser Gln Asn Val His Asn Arg
            20                  25                  30

Leu Thr Trp Tyr Gln Gln Lys Pro Gly Lys Ala Pro Lys Leu Leu Ile
        35                  40                  45

Tyr Gly Ala Ser Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Gly Ser Pro Thr
                85                  90                  95

Thr Phe Gly Gln Gly
            100

<210> SEQ ID NO 17
<211> LENGTH: 113
<212> TYPE: PRT
<213> ORGANISM: Artificial Sequence
<220> FEATURE:
<223> OTHER INFORMATION: Fusion Protein, experimentally altered human
      sequence

<400> SEQUENCE: 17
```

```
Thr Lys Val Glu Ile Lys Arg Thr Val Ala Ala Pro Ser Val Phe Ile
1               5                   10                  15

Phe Pro Pro Ser Asp Glu Gln Leu Lys Ser Gly Thr Ala Ser Val Val
            20                  25                  30

Cys Leu Leu Asn Asn Phe Tyr Pro Arg Glu Ala Lys Val Gln Trp Lys
            35                  40                  45

Val Asp Asn Ala Leu Gln Ser Gly Asn Ser Gln Glu Ser Val Thr Glu
50                  55                  60

Gln Asp Ser Lys Asp Ser Thr Tyr Ser Leu Ser Ser Thr Leu Thr Leu
65                  70                  75                  80

Ser Lys Ala Asp Tyr Glu Lys His Lys Val Tyr Ala Cys Glu Val Thr
                85                  90                  95

His Gln Gly Leu Ser Ser Pro Val Thr Lys Ser Phe Asn Arg Gly Glu
            100                 105                 110

Cys

<210> SEQ ID NO 18
<211> LENGTH: 112
<212> TYPE: PRT
<213> ORGANISM: Artificial Sequence
<220> FEATURE:
<223> OTHER INFORMATION: Fusion Protein, experimentally altered human
      sequence

<400> SEQUENCE: 18

Thr Lys Leu Thr Val Leu Gly Gln Pro Lys Ala Ala Pro Ser Val Thr
1               5                   10                  15

Leu Phe Pro Pro Ser Ser Glu Glu Leu Gln Ala Asn Lys Ala Thr Leu
            20                  25                  30

Val Cys Leu Ile Ser Asp Phe Tyr Pro Gly Ala Val Thr Val Ala Trp
            35                  40                  45

Lys Ala Asp Ser Ser Pro Val Lys Ala Gly Val Glu Thr Thr Thr Pro
50                  55                  60

Ser Lys Gln Ser Asn Asn Lys Tyr Ala Ala Ser Ser Tyr Leu Ser Leu
65                  70                  75                  80

Thr Pro Glu Gln Trp Lys Ser His Arg Ser Tyr Ser Cys Gln Val Thr
                85                  90                  95

His Glu Gly Ser Thr Val Glu Lys Thr Val Ala Pro Thr Glu Cys Ser
            100                 105                 110

<210> SEQ ID NO 19
<211> LENGTH: 337
<212> TYPE: PRT
<213> ORGANISM: Artificial Sequence
<220> FEATURE:
<223> OTHER INFORMATION: IgG1, experimentally altered human sequence

<400> SEQUENCE: 19

Thr Leu Val Thr Val Ser Ser Ala Ser Thr Lys Gly Pro Ser Val Phe
1               5                   10                  15

Pro Leu Ala Pro Ser Ser Lys Ser Thr Ser Gly Gly Thr Ala Ala Leu
            20                  25                  30

Gly Cys Leu Val Lys Asp Tyr Phe Pro Glu Pro Val Thr Val Ser Trp
            35                  40                  45

Asn Ser Gly Ala Leu Thr Ser Gly Val His Thr Phe Pro Ala Val Leu
50                  55                  60

Gln Ser Ser Gly Leu Tyr Ser Leu Ser Ser Val Val Thr Val Pro Ser
65                  70                  75                  80
```

Ser Ser Leu Gly Thr Gln Thr Tyr Ile Cys Asn Val Asn His Lys Pro
            85                  90                  95

Ser Asn Thr Lys Val Asp Lys Lys Val Glu Pro Lys Ser Cys Asp Lys
            100                 105                 110

Thr His Thr Cys Pro Pro Cys Pro Ala Pro Glu Leu Leu Gly Gly Pro
            115                 120                 125

Ser Val Phe Leu Phe Pro Pro Lys Pro Lys Asp Thr Leu Met Ile Ser
130                 135                 140

Arg Thr Pro Glu Val Thr Cys Val Val Val Asp Val Ser His Glu Asp
145                 150                 155                 160

Pro Glu Val Lys Phe Asn Trp Tyr Val Asp Gly Val Glu Val His Asn
                165                 170                 175

Ala Lys Thr Lys Pro Arg Glu Glu Gln Tyr Asn Ser Thr Tyr Arg Val
            180                 185                 190

Val Ser Val Leu Thr Val Leu His Gln Asp Trp Leu Asn Gly Lys Glu
        195                 200                 205

Tyr Lys Cys Lys Val Ser Asn Lys Ala Leu Pro Ala Pro Ile Glu Lys
    210                 215                 220

Thr Ile Ser Lys Ala Lys Gly Gln Pro Arg Glu Pro Gln Val Tyr Thr
225                 230                 235                 240

Leu Pro Pro Ser Arg Glu Glu Met Thr Lys Asn Gln Val Ser Leu Thr
                245                 250                 255

Cys Leu Val Lys Gly Phe Tyr Pro Ser Asp Ile Ala Val Glu Trp Glu
            260                 265                 270

Ser Asn Gly Gln Pro Glu Asn Asn Tyr Lys Thr Thr Pro Pro Val Leu
        275                 280                 285

Asp Ser Asp Gly Ser Phe Phe Leu Tyr Ser Lys Leu Thr Val Asp Lys
    290                 295                 300

Ser Arg Trp Gln Gln Gly Asn Val Phe Ser Cys Ser Val Met His Glu
305                 310                 315                 320

Ala Leu His Asn His Tyr Thr Gln Lys Ser Leu Ser Leu Ser Pro Gly
                325                 330                 335

Lys

<210> SEQ ID NO 20
<211> LENGTH: 333
<212> TYPE: PRT
<213> ORGANISM: Artificial Sequence
<220> FEATURE:
<223> OTHER INFORMATION: IgG2, experimentally altered human sequence

<400> SEQUENCE: 20

Thr Thr Val Thr Val Ser Thr Ala Ser Thr Lys Gly Pro Ser Val Phe
1               5                   10                  15

Pro Leu Ala Pro Cys Ser Arg Ser Thr Ser Glu Ser Thr Ala Ala Leu
            20                  25                  30

Gly Cys Leu Val Lys Asp Tyr Phe Pro Glu Pro Val Thr Val Ser Trp
        35                  40                  45

Asn Ser Gly Ala Leu Thr Ser Gly Val His Thr Phe Pro Ala Val Leu
    50                  55                  60

Gln Ser Ser Gly Leu Tyr Ser Leu Ser Ser Val Val Thr Val Pro Ser
65                  70                  75                  80

Ser Asn Phe Gly Thr Gln Thr Tyr Thr Cys Asn Val Asp His Lys Pro
                85                  90                  95

```
Ser Asn Thr Lys Val Asp Lys Thr Val Glu Arg Lys Cys Cys Val Glu
            100                 105                 110

Cys Pro Pro Cys Pro Ala Pro Val Ala Gly Pro Ser Val Phe Leu
            115                 120                 125

Phe Pro Pro Lys Pro Lys Asp Thr Leu Met Ile Ser Arg Thr Pro Glu
            130                 135                 140

Val Thr Cys Val Val Val Asp Val Ser His Glu Asp Pro Glu Val Gln
145                 150                 155                 160

Phe Asn Trp Tyr Val Asp Gly Val Glu Val His Asn Ala Lys Thr Lys
                165                 170                 175

Pro Arg Glu Glu Gln Phe Asn Ser Thr Phe Arg Val Val Ser Val Leu
            180                 185                 190

Thr Val Val His Gln Asp Trp Leu Asn Gly Lys Glu Tyr Lys Cys Lys
            195                 200                 205

Val Ser Asn Lys Gly Leu Pro Ala Pro Ile Glu Lys Thr Ile Ser Lys
            210                 215                 220

Thr Lys Gly Gln Pro Arg Glu Pro Gln Val Tyr Thr Leu Pro Pro Ser
225                 230                 235                 240

Arg Glu Glu Met Thr Lys Asn Gln Val Ser Leu Thr Cys Leu Val Lys
            245                 250                 255

Gly Phe Tyr Pro Ser Asp Ile Ala Val Glu Trp Glu Ser Asn Gly Gln
            260                 265                 270

Pro Glu Asn Asn Tyr Lys Thr Thr Pro Pro Met Leu Asp Ser Asp Gly
            275                 280                 285

Ser Phe Phe Leu Tyr Ser Lys Leu Thr Val Asp Lys Ser Arg Trp Gln
            290                 295                 300

Gln Gly Asn Val Phe Ser Cys Ser Val Met His Glu Ala Leu His Asn
305                 310                 315                 320

His Tyr Thr Gln Lys Ser Leu Ser Leu Ser Pro Gly Lys
            325                 330

<210> SEQ ID NO 21
<211> LENGTH: 334
<212> TYPE: PRT
<213> ORGANISM: Artificial Sequence
<220> FEATURE:
<223> OTHER INFORMATION: IgG4, experimentally altered human sequence

<400> SEQUENCE: 21

Thr Leu Val Thr Val Ser Ser Ala Ser Thr Lys Gly Pro Ser Val Phe
1               5                   10                  15

Pro Leu Ala Pro Cys Ser Arg Ser Thr Ser Glu Ser Thr Ala Ala Leu
            20                  25                  30

Gly Cys Leu Val Lys Asp Tyr Phe Pro Glu Pro Val Thr Val Ser Trp
            35                  40                  45

Asn Ser Gly Ala Leu Thr Ser Gly Val His Thr Phe Pro Ala Val Leu
        50                  55                  60

Gln Ser Ser Gly Leu Tyr Ser Leu Ser Ser Val Val Thr Val Pro Ser
65                  70                  75                  80

Ser Ser Leu Gly Thr Lys Thr Tyr Thr Cys Asn Val Asp His Lys Pro
            85                  90                  95

Ser Asn Thr Lys Val Asp Lys Arg Val Glu Ser Lys Tyr Gly Pro Pro
            100                 105                 110

Cys Pro Pro Cys Pro Ala Pro Glu Phe Leu Gly Gly Pro Ser Val Phe
            115                 120                 125
```

Leu Phe Pro Pro Lys Pro Lys Asp Thr Leu Met Ile Ser Arg Thr Pro
130                 135                 140

Glu Val Thr Cys Val Val Val Asp Val Ser Gln Glu Asp Pro Glu Val
145                 150                 155                 160

Gln Phe Asn Trp Tyr Val Asp Gly Val Glu Val His Asn Ala Lys Thr
                165                 170                 175

Lys Pro Arg Glu Glu Gln Phe Asn Ser Thr Tyr Arg Val Val Ser Val
                180                 185                 190

Leu Thr Val Leu His Gln Asp Trp Leu Asn Gly Lys Glu Tyr Lys Cys
            195                 200                 205

Lys Val Ser Asn Lys Gly Leu Pro Ser Ser Ile Glu Lys Thr Ile Ser
210                 215                 220

Lys Ala Lys Gly Gln Pro Arg Glu Pro Gln Val Tyr Thr Leu Pro Pro
225                 230                 235                 240

Ser Gln Glu Glu Met Thr Lys Asn Gln Val Ser Leu Thr Cys Leu Val
                245                 250                 255

Lys Gly Phe Tyr Pro Ser Asp Ile Ala Val Glu Trp Glu Ser Asn Gly
                260                 265                 270

Gln Pro Glu Asn Asn Tyr Lys Thr Thr Pro Pro Val Leu Asp Ser Asp
            275                 280                 285

Gly Ser Phe Phe Leu Tyr Ser Arg Leu Thr Val Asp Lys Ser Arg Trp
290                 295                 300

Gln Glu Gly Asn Val Phe Ser Cys Ser Val Met His Glu Ala Leu His
305                 310                 315                 320

Asn His Tyr Thr Gln Lys Ser Leu Ser Leu Ser Leu Gly Lys
                325                 330

<210> SEQ ID NO 22
<211> LENGTH: 235
<212> TYPE: PRT
<213> ORGANISM: Artificial Sequence
<220> FEATURE:
<223> OTHER INFORMATION: Fusion Protein, experimentally altered human
      sequence

<400> SEQUENCE: 22

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
                20                  25                  30

Ser Lys Cys Ser Pro Gly Gln His Ala Lys Val Phe Cys Thr Lys Thr
            35                  40                  45

Ser Asp Thr Val Cys Asp Ser Cys Glu Asp Ser Thr Tyr Thr Gln Leu
50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
            115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp
225                 230                 235

<210> SEQ ID NO 23
<211> LENGTH: 162
<212> TYPE: PRT
<213> ORGANISM: Artificial Sequence
<220> FEATURE:
<223> OTHER INFORMATION: Fusion Protein, experimentally altered human
      sequence

<400> SEQUENCE: 23

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile

<210> SEQ ID NO 24
<211> LENGTH: 182
<212> TYPE: PRT
<213> ORGANISM: Artificial Sequence
<220> FEATURE:
<223> OTHER INFORMATION: Fusion Protein, experimentally altered human
      sequence

<400> SEQUENCE: 24

Leu Val Pro His Leu Gly Asp Arg Glu Lys Arg Asp Ser Val Cys Pro
1               5                   10                  15

Gln Gly Lys Tyr Ile His Pro Gln Asn Asn Ser Ile Cys Cys Thr Lys
            20                  25                  30

Cys His Lys Gly Thr Tyr Leu Tyr Asn Asp Cys Pro Gly Pro Gly Gln
        35                  40                  45

```
Asp Thr Asp Cys Arg Glu Cys Glu Ser Gly Ser Phe Thr Ala Ser Glu
 50                  55                  60

Asn His Leu Arg His Cys Leu Ser Cys Ser Lys Cys Arg Lys Glu Met
 65                  70                  75                  80

Gly Gln Val Glu Ile Ser Ser Cys Thr Val Asp Arg Asp Thr Val Cys
                     85                  90                  95

Gly Cys Arg Lys Asn Gln Tyr Arg His Tyr Trp Ser Glu Asn Leu Phe
                100                 105                 110

Gln Cys Phe Asn Cys Ser Leu Cys Leu Asn Gly Thr Val His Leu Ser
                115                 120                 125

Cys Gln Glu Lys Gln Asn Thr Val Cys Thr Cys His Ala Gly Phe Phe
            130                 135                 140

Leu Arg Glu Asn Glu Cys Val Ser Cys Ser Asn Cys Lys Lys Ser Leu
145                 150                 155                 160

Glu Cys Thr Lys Leu Cys Leu Pro Gln Ile Glu Asn Val Lys Gly Thr
                165                 170                 175

Glu Asp Ser Gly Thr Thr
            180
```

<210> SEQ ID NO 25
<211> LENGTH: 161
<212> TYPE: PRT
<213> ORGANISM: Artificial Sequence
<220> FEATURE:
<223> OTHER INFORMATION: Fusion Protein, experimentally altered human
      sequence

<400> SEQUENCE: 25

```
Leu Val Pro His Leu Gly Asp Arg Glu Lys Arg Asp Ser Val Cys Pro
 1               5                  10                  15

Gln Gly Lys Tyr Ile His Pro Gln Asn Asn Ser Ile Cys Cys Thr Lys
                 20                  25                  30

Cys His Lys Gly Thr Tyr Leu Tyr Asn Asp Cys Pro Gly Pro Gly Gln
             35                  40                  45

Asp Thr Asp Cys Arg Glu Cys Glu Ser Gly Ser Phe Thr Ala Ser Glu
 50                  55                  60

Asn His Leu Arg His Cys Leu Ser Cys Ser Lys Cys Arg Lys Glu Met
 65                  70                  75                  80

Gly Gln Val Glu Ile Ser Ser Cys Thr Val Asp Arg Asp Thr Val Cys
                     85                  90                  95

Gly Cys Arg Lys Asn Gln Tyr Arg His Tyr Trp Ser Glu Asn Leu Phe
                100                 105                 110

Gln Cys Phe Asn Cys Ser Leu Cys Leu Asn Gly Thr Val His Leu Ser
                115                 120                 125

Cys Gln Glu Lys Gln Asn Thr Val Cys Thr Cys His Ala Gly Phe Phe
            130                 135                 140

Leu Arg Glu Asn Glu Cys Val Ser Cys Ser Asn Cys Lys Lys Ser Leu
145                 150                 155                 160

Glu
```

<210> SEQ ID NO 26
<211> LENGTH: 743
<212> TYPE: DNA
<213> ORGANISM: Artificial Sequence
<220> FEATURE:
<223> OTHER INFORMATION: BY19.4 Light Chain, experimentally altered
      human sequence

<400> SEQUENCE: 26

```
tctagagcca ccatggagac cgacaccctc ctcctgtggg tgctgctgct gtgggtgccc      60
ggctctaccg gcgacatcgt gatgactcag acaccactga gcctgtctgt gaccccaggc     120
cagcccgctt cgatttcttg ccggtcctct cgcagcctgg tgcactctag ggcaacaca      180
tacctccact ggtatctaca gaagcccggc cagtcccctc agctgctgat ctacaaggtg     240
tctaacaggt tcattggcgt gcccgaccgc ttctccggct ctggcagcgg caccgacttc     300
acactcaaga ttagcagagt ggaggctgag gacgtgggcg tgtactactg ctctcagtct     360
acccacctcc ctttcacatt cggccagggc acaaaggtgg agatcaagcg gaccgtggcc     420
gccccatccg tgttcatttt cccaccttcc gacgagcagc tgaagtctgg caccgccagc     480
gtggtgtgcc tgctgaacaa cttctacccc cgcgaggcca aggtgcagtg gaaggtggac     540
aacgccctgc agagcggcaa cagccaggag agcgtgaccg agcaggactc caaggacagc     600
acctacagcc tgagcagcac cctgaccctg agcaaggccg actacgagaa gcacaaggtg     660
tacgcctgcg aggtgaccca ccagggactg tctagccccg tgaccaagag cttcaaccgg     720
ggcgagtgct aagaattgtc gac                                            743
```

<210> SEQ ID NO 27
<211> LENGTH: 239
<212> TYPE: PRT
<213> ORGANISM: Artificial Sequence
<220> FEATURE:
<223> OTHER INFORMATION: BY19.4 Light Chain, experimentally altered human sequence

<400> SEQUENCE: 27

```
Met Glu Thr Asp Thr Leu Leu Leu Trp Val Leu Leu Leu Trp Val Pro
1               5                   10                  15

Gly Ser Thr Gly Asp Ile Val Met Thr Gln Thr Pro Leu Ser Leu Ser
            20                  25                  30

Val Thr Pro Gly Gln Pro Ala Ser Ile Ser Cys Arg Ser Ser Arg Ser
        35                  40                  45

Leu Val His Ser Arg Gly Asn Thr Tyr Leu His Trp Tyr Leu Gln Lys
    50                  55                  60

Pro Gly Gln Ser Pro Gln Leu Leu Ile Tyr Lys Val Ser Asn Arg Phe
65                  70                  75                  80

Ile Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Leu Pro Phe Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
```

Gly Leu Ser Ser Pro Val Thr Lys Ser Phe Asn Arg Gly Glu Cys
225                 230                 235

<210> SEQ ID NO 28
<211> LENGTH: 1416
<212> TYPE: DNA
<213> ORGANISM: Artificial Sequence
<220> FEATURE:
<223> OTHER INFORMATION: BY19.4 Heavy Chain, experimentally altered
      human sequence

<400> SEQUENCE: 28

```
ctcgaggcca ccatggagac cgacacactc ctcctgtggg tgctgctgct ctgggtgcca      60
ggcagcaccg gccaggtgca gctcgtgcag agcggcgccg aggtgaagaa gcccggctct     120
tctgtgaagg tgtcttgcaa ggcttccggc tactctttca ccgactacca cattcactgg    180
gtgcgccagg ctcctggcca gggccttgag tggatgggcg tgattaaccc tatgtacggc    240
acaacagact acaaccagcg gttcaagggc agagtgacca ttacagccga cgagtccaca    300
tccaccgctt acatggagct gtcctccctg cgttctgagg acactgctgt gtactactgc    360
gctagatacg actacttcac cggcactggc gtgtactggg gccagggcac actcgtgacc    420
gtgtctagcg catcaacaaa gggcccatct gtgttcccac tcgccccatg ctcccgctcc    480
acctccgagt ccaccgccgc cctgggctgc tggtgaagg actacttccc tgagcctgtg    540
accgtgtcct ggaactccgg cgccctgacc tccggcgtgc acaccttccc tgccgtgctg    600
cagtcctccg gcctgtactc cctgtcctcc gtggtgaccg tgccttcctc ctccctgggc    660
accaagacct acacctgcaa cgtggaccac aagccttcca acaccaaggt ggacaagcgc    720
gtggagtcca gtacgggccc tccttgccct ccttgccctg ccctgagtt cctgggcggc    780
ccttccgtgt tcctgttccc tcctaagcct aaggacaccc tgatgatctc ccgcaccct    840
gaggtgacct gcgtggtggt ggacgtgtcc caggaggacc ctgaggtgca gttcaactgg    900
tacgtggacg gcgtggaggt gcacaacgcc aagaccaagc ctcgcgagga gcagttcaac    960
tccacctacc gcgtggtgtc cgtgctgacc gtgctgcacc aggactggct gaacggcaag   1020
gagtacaagt gcaaggtgtc caacaagggc ctgccttcct ccatcgagaa gaccatctcc   1080
aaggccaagg gccagcctcg cgagcctcag gtgtacaccc tgcctccttc caggaggag    1140
atgaccaaga accaggtgtc cctgacctgc ctggtgaagg gcttctaccc ttccgacatc   1200
gccgtggagt gggagtccaa cggccagcct gagaacaact acaagaccac ccctcctgtg   1260
ctggactccg acggctcctt cttcctgtac tcccgcctga ccgtggacaa gtcccgctgg   1320
caggagggca acgtgttctc ctgctccgtg atgcacgagg ccctgcacaa ccactacacc   1380
cagaagtccc tgtccctgtc cctgggctaa gaattc                             1416
```

<210> SEQ ID NO 29
<211> LENGTH: 465
<212> TYPE: PRT
<213> ORGANISM: Artificial Sequence
<220> FEATURE:
<223> OTHER INFORMATION: BY19.4 Heavy Chain, experimentally altered
      human sequence

<400> SEQUENCE: 29

Met Glu Thr Asp Thr Leu Leu Leu Trp Val Leu Leu Leu Trp Val Pro
1               5                   10                  15

Gly Ser Thr Gly Gln Val Gln Leu Val Gln Ser Gly Ala Glu Val Lys

```
                20              25              30
Lys Pro Gly Ser Ser Val Lys Val Ser Cys Lys Ala Ser Gly Tyr Ser
            35              40              45

Phe Thr Asp Tyr His Ile His Trp Val Arg Gln Ala Pro Gly Gln Gly
50              55              60

Leu Glu Trp Met Gly Val Ile Asn Pro Met Tyr Gly Thr Thr Asp Tyr
65              70              75              80

Asn Gln Arg Phe Lys Gly Arg Val Thr Ile Thr Ala Asp Glu Ser Thr
            85              90              95

Ser Thr Ala Tyr Met Glu Leu Ser Ser Leu Arg Ser Glu Asp Thr Ala
            100             105             110

Val Tyr Tyr Cys Ala Arg Tyr Asp Tyr Phe Thr Gly Thr Gly Val Tyr
            115             120             125

Trp Gly Gln Gly Thr Leu Val Thr Val Ser Ser Ala Ser Thr Lys Gly
            130             135             140

Pro Ser Val Phe Pro Leu Ala Pro Cys Ser Arg Ser Thr Ser Glu Ser
145             150             155             160

Thr Ala Ala Leu Gly Cys Leu Val Lys Asp Tyr Phe Pro Glu Pro Val
            165             170             175

Thr Val Ser Trp Asn Ser Gly Ala Leu Thr Ser Gly Val His Thr Phe
            180             185             190

Pro Ala Val Leu Gln Ser Ser Gly Leu Tyr Ser Leu Ser Ser Val Val
            195             200             205

Thr Val Pro Ser Ser Ser Leu Gly Thr Lys Thr Tyr Thr Cys Asn Val
            210             215             220

Asp His Lys Pro Ser Asn Thr Lys Val Asp Lys Arg Val Glu Ser Lys
225             230             235             240

Tyr Gly Pro Pro Cys Pro Pro Cys Pro Ala Pro Glu Phe Leu Gly Gly
            245             250             255

Pro Ser Val Phe Leu Phe Pro Pro Lys Pro Lys Asp Thr Leu Met Ile
            260             265             270

Ser Arg Thr Pro Glu Val Thr Cys Val Val Val Asp Val Ser Gln Glu
            275             280             285

Asp Pro Glu Val Gln Phe Asn Trp Tyr Val Asp Gly Val Glu Val His
            290             295             300

Asn Ala Lys Thr Lys Pro Arg Glu Glu Gln Phe Asn Ser Thr Tyr Arg
305             310             315             320

Val Val Ser Val Leu Thr Val Leu His Gln Asp Trp Leu Asn Gly Lys
            325             330             335

Glu Tyr Lys Cys Lys Val Ser Asn Lys Gly Leu Pro Ser Ser Ile Glu
            340             345             350

Lys Thr Ile Ser Lys Ala Lys Gly Gln Pro Arg Glu Pro Gln Val Tyr
            355             360             365

Thr Leu Pro Pro Ser Gln Glu Glu Met Thr Lys Asn Gln Val Ser Leu
            370             375             380

Thr Cys Leu Val Lys Gly Phe Tyr Pro Ser Asp Ile Ala Val Glu Trp
385             390             395             400

Glu Ser Asn Gly Gln Pro Glu Asn Asn Tyr Lys Thr Thr Pro Pro Val
            405             410             415

Leu Asp Ser Asp Gly Ser Phe Phe Leu Tyr Ser Arg Leu Thr Val Asp
            420             425             430

Lys Ser Arg Trp Gln Glu Gly Asn Val Phe Ser Cys Ser Val Met His
            435             440             445
```

Glu Ala Leu His Asn His Tyr Thr Gln Lys Ser Leu Ser Leu Ser Leu
    450                 455                 460

Gly
465

<210> SEQ ID NO 30
<211> LENGTH: 16
<212> TYPE: PRT
<213> ORGANISM: Artificial Sequence
<220> FEATURE:
<223> OTHER INFORMATION: Linker Peptide

<400> SEQUENCE: 30

Ala Lys Thr Thr Pro Lys Leu Glu Glu Gly Glu Phe Ser Glu Ala Arg
1               5                   10                  15

<210> SEQ ID NO 31
<211> LENGTH: 17
<212> TYPE: PRT
<213> ORGANISM: Artificial Sequence
<220> FEATURE:
<223> OTHER INFORMATION: Linker Peptide

<400> SEQUENCE: 31

Ala Lys Thr Thr Pro Lys Leu Glu Glu Gly Glu Phe Ser Glu Ala Arg
1               5                   10                  15

Val

<210> SEQ ID NO 32
<211> LENGTH: 9
<212> TYPE: PRT
<213> ORGANISM: Artificial Sequence
<220> FEATURE:
<223> OTHER INFORMATION: Linker Peptide

<400> SEQUENCE: 32

Ala Lys Thr Thr Pro Lys Leu Gly Gly
1               5

<210> SEQ ID NO 33
<211> LENGTH: 10
<212> TYPE: PRT
<213> ORGANISM: Artificial Sequence
<220> FEATURE:
<223> OTHER INFORMATION: Linker Peptide

<400> SEQUENCE: 33

Ser Ala Lys Thr Thr Pro Lys Leu Gly Gly
1               5                   10

<210> SEQ ID NO 34
<211> LENGTH: 6
<212> TYPE: PRT
<213> ORGANISM: Artificial Sequence
<220> FEATURE:
<223> OTHER INFORMATION: Linker Peptide

<400> SEQUENCE: 34

Ser Ala Lys Thr Thr Pro
1               5

<210> SEQ ID NO 35
<211> LENGTH: 6
<212> TYPE: PRT
<213> ORGANISM: Artificial Sequence

```
<220> FEATURE:
<223> OTHER INFORMATION: Linker Peptide

<400> SEQUENCE: 35

Arg Ala Asp Ala Ala Pro
1               5

<210> SEQ ID NO 36
<211> LENGTH: 9
<212> TYPE: PRT
<213> ORGANISM: Artificial Sequence
<220> FEATURE:
<223> OTHER INFORMATION: Linker Peptide

<400> SEQUENCE: 36

Arg Ala Asp Ala Ala Pro Thr Val Ser
1               5

<210> SEQ ID NO 37
<211> LENGTH: 12
<212> TYPE: PRT
<213> ORGANISM: Artificial Sequence
<220> FEATURE:
<223> OTHER INFORMATION: Linker Peptide

<400> SEQUENCE: 37

Arg Ala Asp Ala Ala Ala Ala Gly Gly Pro Gly Ser
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Linker Peptide

<400> SEQUENCE: 38

Arg Ala Asp Ala Ala Ala Ala
1               5

<210> SEQ ID NO 39
<211> LENGTH: 18
<212> TYPE: PRT
<213> ORGANISM: Artificial Sequence
<220> FEATURE:
<223> OTHER INFORMATION: Linker Peptide

<400> SEQUENCE: 39

Ser Ala Lys Thr Thr Pro Lys Leu Glu Glu Gly Glu Phe Ser Glu Ala
1               5                   10                  15

Arg Val

<210> SEQ ID NO 40
<211> LENGTH: 5
<212> TYPE: PRT
<213> ORGANISM: Artificial Sequence
<220> FEATURE:
<223> OTHER INFORMATION: Linker Peptide

<400> SEQUENCE: 40

Ala Asp Ala Ala Pro
1               5

<210> SEQ ID NO 41
<211> LENGTH: 11
<212> TYPE: PRT
```

```
<213> ORGANISM: Artificial Sequence
<220> FEATURE:
<223> OTHER INFORMATION: Linker Peptide

<400> SEQUENCE: 41

Asp Ala Ala Pro Thr Val Ser Ile Phe Pro Pro
1               5                   10

<210> SEQ ID NO 42
<211> LENGTH: 5
<212> TYPE: PRT
<213> ORGANISM: Artificial Sequence
<220> FEATURE:
<223> OTHER INFORMATION: Linker Peptide

<400> SEQUENCE: 42

Thr Val Ala Ala Pro
1               5

<210> SEQ ID NO 43
<211> LENGTH: 12
<212> TYPE: PRT
<213> ORGANISM: Artificial Sequence
<220> FEATURE:
<223> OTHER INFORMATION: Linker Peptide

<400> SEQUENCE: 43

Thr Val Ala Ala Pro Ser Val Phe Ile Phe Pro Pro
1               5                   10

<210> SEQ ID NO 44
<211> LENGTH: 6
<212> TYPE: PRT
<213> ORGANISM: Artificial Sequence
<220> FEATURE:
<223> OTHER INFORMATION: Linker Peptide

<400> SEQUENCE: 44

Gln Pro Lys Ala Ala Pro
1               5

<210> SEQ ID NO 45
<211> LENGTH: 13
<212> TYPE: PRT
<213> ORGANISM: Artificial Sequence
<220> FEATURE:
<223> OTHER INFORMATION: Linker Peptide

<400> SEQUENCE: 45

Gln Pro Lys Ala Ala Pro Ser Val Thr Leu Phe Pro Pro
1               5                   10

<210> SEQ ID NO 46
<211> LENGTH: 6
<212> TYPE: PRT
<213> ORGANISM: Artificial Sequence
<220> FEATURE:
<223> OTHER INFORMATION: Linker Peptide

<400> SEQUENCE: 46

Ala Lys Thr Thr Pro Pro
1               5

<210> SEQ ID NO 47
<211> LENGTH: 13
<212> TYPE: PRT
<213> ORGANISM: Artificial Sequence
```

-continued

```
<220> FEATURE:
<223> OTHER INFORMATION: Linker Peptide

<400> SEQUENCE: 47

Ala Lys Thr Thr Pro Pro Ser Val Thr Pro Leu Ala Pro
1               5                   10

<210> SEQ ID NO 48
<211> LENGTH: 6
<212> TYPE: PRT
<213> ORGANISM: Artificial Sequence
<220> FEATURE:
<223> OTHER INFORMATION: Linker Peptide

<400> SEQUENCE: 48

Ala Lys Thr Thr Ala Pro
1               5

<210> SEQ ID NO 49
<211> LENGTH: 13
<212> TYPE: PRT
<213> ORGANISM: Artificial Sequence
<220> FEATURE:
<223> OTHER INFORMATION: Linker Peptide

<400> SEQUENCE: 49

Ala Lys Thr Thr Ala Pro Ser Val Tyr Pro Leu Ala Pro
1               5                   10

<210> SEQ ID NO 50
<211> LENGTH: 6
<212> TYPE: PRT
<213> ORGANISM: Artificial Sequence
<220> FEATURE:
<223> OTHER INFORMATION: Linker Peptide

<400> SEQUENCE: 50

Ala Ser Thr Lys Gly Pro
1               5

<210> SEQ ID NO 51
<211> LENGTH: 13
<212> TYPE: PRT
<213> ORGANISM: Artificial Sequence
<220> FEATURE:
<223> OTHER INFORMATION: Linker Peptide

<400> SEQUENCE: 51

Ala Ser Thr Lys Gly Pro Ser Val Phe Pro Leu Ala Pro
1               5                   10

<210> SEQ ID NO 52
<211> LENGTH: 15
<212> TYPE: PRT
<213> ORGANISM: Artificial Sequence
<220> FEATURE:
<223> OTHER INFORMATION: Linker Peptide

<400> SEQUENCE: 52

Gly Gly Gly Gly Ser Gly Gly Gly Ser Gly Gly Gly Gly Ser
1               5                   10                  15

<210> SEQ ID NO 53
<211> LENGTH: 15
<212> TYPE: PRT
<213> ORGANISM: Artificial Sequence
<220> FEATURE:
```

<223> OTHER INFORMATION: Linker Peptide

<400> SEQUENCE: 53

Gly Glu Asn Lys Val Glu Tyr Ala Pro Ala Leu Met Ala Leu Ser
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Linker Peptide

<400> SEQUENCE: 54

Gly Pro Ala Lys Glu Leu Thr Pro Leu Lys Glu Ala Lys Val Ser
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Linker Peptide

<400> SEQUENCE: 55

Gly His Glu Ala Ala Ala Val Met Gln Val Gln Tyr Pro Ala Ser
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Linker Peptide

<400> SEQUENCE: 56

Gly Gly Gly Gly Ser Gly Gly Gly Ser Gly Gly Gly Gly Ser Ala
1               5                   10                  15

<210> SEQ ID NO 57
<211> LENGTH: 19
<212> TYPE: PRT
<213> ORGANISM: Artificial Sequence
<220> FEATURE:
<223> OTHER INFORMATION: Linker Peptide

<400> SEQUENCE: 57

Gly Gln Gly Thr Lys Val Glu Ile Lys Arg Gly Gly Ser Gly Gly
1               5                   10                  15

Gly Ser Gly

<210> SEQ ID NO 58
<211> LENGTH: 20
<212> TYPE: PRT
<213> ORGANISM: Artificial Sequence
<220> FEATURE:
<223> OTHER INFORMATION: Linker Peptide

<400> SEQUENCE: 58

Gly Gln Gly Thr Leu Val Thr Val Ser Ser Gly Gly Gly Gly Ser Gly
1               5                   10                  15

Gly Gly Gly Ser
            20

<210> SEQ ID NO 59

-continued

```
<211> LENGTH: 743
<212> TYPE: DNA
<213> ORGANISM: Artificial Sequence
<220> FEATURE:
<223> OTHER INFORMATION: IgG4, experimentally altered human sequence

<400> SEQUENCE: 59
tctagagcca ccatggagac cgacaccctc ctcctgtggg tgctgctgct gtgggtgccc      60
ggctctaccg cgacatcgt gatgactcag acaccactga gcctgtctgt gaccccaggc     120
cagcccgctt cgatttcttg ccggtcctct cgcagcctgg tgcactctag gggcaacaca     180
tacctccact ggtatctaca gaagcccggc cagtcccctc agctgctgat ctacaaggtg     240
tctaacaggt tcattggcgt gcccgaccgc ttctccggct ctggcagcgg caccgacttc     300
acactcaaga ttagcagagt ggaggctgag gacgtgggcg tgtactactg ctctcagtct     360
acccacctcc ctttcacatt cggccagggc acaaaggtgg agatcaagcg gaccgtggcc     420
gccccatccg tgttcatttt cccaccttcc gacgagcagc tgaagtctgg caccgccagc     480
gtggtgtgcc tgctgaacaa cttctacccc cgcgaggcca aggtgcagtg gaaggtggac     540
aacgccctgc agagcggcaa cagccaggag agcgtgaccg agcaggactc caaggacagc     600
acctacagcc tgagcagcac cctgaccctg agcaaggcca actacgagaa gcacaaggtg     660
tacgcctgcg aggtgaccca ccagggactg tctagccccg tgaccaagag cttcaaccgg     720
ggcgagtgct aagaattgtc gac                                              743

<210> SEQ ID NO 60
<211> LENGTH: 239
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 60

Met Glu Thr Asp Thr Leu Leu Leu Trp Val Leu Leu Leu Trp Val Pro
1               5                   10                  15

Gly Ser Thr Gly Asp Ile Val Met Thr Gln Thr Pro Leu Ser Leu Ser
            20                  25                  30

Val Thr Pro Gly Gln Pro Ala Ser Ile Ser Cys Arg Ser Ser Arg Ser
        35                  40                  45

Leu Val His Ser Arg Gly Asn Thr Tyr Leu His Trp Tyr Leu Gln Lys
    50                  55                  60

Pro Gly Gln Ser Pro Gln Leu Leu Ile Tyr Lys Val Ser Asn Arg Phe
65                  70                  75                  80

Ile Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Leu Pro Phe Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
```

|  | 180 |  |  | 185 |  |  |  | 190 |  |  |
|---|---|---|---|---|---|---|---|---|---|---|

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
   210                 215                 220

Gly Leu Ser Ser Pro Val Thr Lys Ser Phe Asn Arg Gly Glu Cys
225              230                 235

<210> SEQ ID NO 61
<211> LENGTH: 1944
<212> TYPE: DNA
<213> ORGANISM: Artificial Sequence
<220> FEATURE:
<223> OTHER INFORMATION: IgG4, experimentally altered human sequence

<400> SEQUENCE: 61

| ctcgaggcca | ccatggagac | cgacacactc | ctcctgtggg | tgctgctgct | ctgggtgcca | 60 |
|---|---|---|---|---|---|---|
| ggcagcaccg | ccaggtgca | gctcgtgcag | agcggcgccg | aggtgaagaa | gcccggctct | 120 |
| tctgtgaagg | tgtcttgcaa | ggcttccggc | tactcttca | ccgactacca | cattcactgg | 180 |
| gtgcgccagc | tcctggcca | gggccttgag | tggatgggcg | tgattaaccc | tatgtacggc | 240 |
| acaacagact | acaaccagcg | gttcaagggc | agagtgacca | ttacagccga | cgagtccaca | 300 |
| tccaccgctt | acatggagct | gtcctccctg | cgttctgagg | acactgctgt | gtactactgc | 360 |
| gctagatacg | actacttcac | cggcactggc | gtgtactggg | gccagggcac | actcgtgacc | 420 |
| gtgtctagcg | catcaacaaa | gggcccatct | gtgttccac | cgccccatg | ctcccgctcc | 480 |
| acctccgagt | ccaccgccgc | cctgggctgc | ctggtgaagg | actacttccc | tgagcctgtg | 540 |
| accgtgtcct | ggaactccgg | cgccctgacc | tccggcgtgc | acaccttccc | tgccgtgctg | 600 |
| cagtcctccg | gcctgtactc | cctgtcctcc | gtggtgaccg | tgccttcctc | ctccctgggc | 660 |
| accaagacct | acacctgcaa | cgtggaccac | aagccttcca | caccaaggt | ggacaagcgc | 720 |
| gtggagtcca | gtacggccc | tccttgccct | ccttgccctg | ccctgagtt | cctgggcggc | 780 |
| ccttccgtgt | tcctgttccc | tcctaagcct | aaggacaccc | tgatgatctc | ccgcaccct | 840 |
| gaggtgacct | gcgtggtggt | ggacgtgtcc | caggaggacc | ctgaggtgca | gttcaactgg | 900 |
| tacgtgacg | gcgtggaggt | gcacaacgcc | aagaccaagc | ctcgcgagga | gcagttcaac | 960 |
| tccacctacc | gcgtggtgtc | cgtgctgacc | gtgctgcacc | aggactggct | gaacggcaag | 1020 |
| gagtacaagt | gcaaggtgtc | caacaagggc | ctgccttcct | ccatcgagaa | gaccatctcc | 1080 |
| aaggccaagg | gccagcctcg | cgagcctcag | gtgtacaccc | tgcctccttc | ccaggaggag | 1140 |
| atgaccaaga | accaggtgtc | cctgacctgc | ctggtgaagg | gcttctaccc | ttccgacatc | 1200 |
| gccgtggagt | gggagtccaa | cggccagcct | gagaacaact | acaagaccac | ccctcctgtg | 1260 |
| ctggactccg | acggctcctt | cttcctgtac | tcccgcctga | ccgtggacaa | gtcccgctgg | 1320 |
| caggagggca | acgtgttctc | ctgctccgtg | atgcacgagg | ccctgcacaa | ccactacacc | 1380 |
| cagaagtccc | tgtccctgtc | cctgggcggc | ggaggatctg | gcggcggagg | cagtggaggc | 1440 |
| ggcggaagcc | tgcccgcaca | agtggccttc | accccctacg | ccccagagcc | cggctctact | 1500 |
| tgtaggctga | gggagtacta | cgaccagacc | gcccagatgt | gctgctccaa | gtgtagcccc | 1560 |
| ggacagcacg | ccaaggtgtt | ctgtacaaag | acctccgaca | ccgtgtgcga | ctcctgcgag | 1620 |
| gactccacct | acacccagct | gtggaactgg | gtgcccgagt | gcctgtcctg | cggctccagg | 1680 |
| tgctcctctg | accaggtcga | gacccaagcc | tgtaccaggg | agcagaacag | gatctgcact | 1740 |

-continued

```
tgcaggccag gctggtattg cgccctgtcc aagcaggaag gctgcaggct gtgcgcccca    1800
ctgaggaaat gtaggcctgg gttcggcgtg gctaggcccg gaaccgagac ttccgacgtg    1860
gtgtgcaagc cctgtgcccc tggcaccttt tccaaccaca cctcctccac cgacatctgt    1920
aggccacacc agatttaaga attc                                           1944

<210> SEQ ID NO 62
<211> LENGTH: 641
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 62

Met Glu Thr Asp Thr Leu Leu Leu Trp Val Leu Leu Leu Trp Val Pro
1               5                   10                  15

Gly Ser Thr Gly Gln Val Gln Leu Val Gln Ser Gly Ala Glu Val Lys
            20                  25                  30

Lys Pro Gly Ser Ser Val Lys Val Ser Cys Lys Ala Ser Gly Tyr Ser
        35                  40                  45

Phe Thr Asp Tyr His Ile His Trp Val Arg Gln Ala Pro Gly Gln Gly
    50                  55                  60

Leu Glu Trp Met Gly Val Ile Asn Pro Met Tyr Gly Thr Thr Asp Tyr
65                  70                  75                  80

Asn Gln Arg Phe Lys Gly Arg Val Thr Ile Thr Ala Asp Glu Ser Thr
                85                  90                  95

Ser Thr Ala Tyr Met Glu Leu Ser Ser Leu Arg Ser Glu Asp Thr Ala
            100                 105                 110

Val Tyr Tyr Cys Ala Arg Tyr Asp Tyr Phe Thr Gly Thr Gly Val Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320
```

Val Val Ser Val Leu Thr Val Leu His Gln Asp Trp Leu Asn Gly Lys
            325                 330                 335

Glu Tyr Lys Cys Lys Val Ser Asn Lys Gly Leu Pro Ser Ser Ile Glu
        340                 345                 350

Lys Thr Ile Ser Lys Ala Lys Gly Gln Pro Arg Glu Pro Gln Val Tyr
    355                 360                 365

Thr Leu Pro Pro Ser Gln Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly Gly Gly Gly Ser Gly Gly Gly Ser Gly Gly Gly Ser Leu
465                 470                 475                 480

Pro Ala Gln Val Ala Phe Thr Pro Tyr Ala Pro Glu Pro Gly Ser Thr
                485                 490                 495

Cys Arg Leu Arg Glu Tyr Tyr Asp Gln Thr Ala Gln Met Cys Cys Ser
            500                 505                 510

Lys Cys Ser Pro Gly Gln His Ala Lys Val Phe Cys Thr Lys Thr Ser
        515                 520                 525

Asp Thr Val Cys Asp Ser Cys Glu Asp Ser Thr Tyr Thr Gln Leu Trp
530                 535                 540

Asn Trp Val Pro Glu Cys Leu Ser Cys Gly Ser Arg Cys Ser Ser Asp
545                 550                 555                 560

Gln Val Glu Thr Gln Ala Cys Thr Arg Glu Gln Asn Arg Ile Cys Thr
                565                 570                 575

Cys Arg Pro Gly Trp Tyr Cys Ala Leu Ser Lys Gln Glu Gly Cys Arg
            580                 585                 590

Leu Cys Ala Pro Leu Arg Lys Cys Arg Pro Gly Phe Gly Val Ala Arg
        595                 600                 605

Pro Gly Thr Glu Thr Ser Asp Val Val Cys Lys Pro Cys Ala Pro Gly
    610                 615                 620

Thr Phe Ser Asn Thr Thr Ser Ser Thr Asp Ile Cys Arg Pro His Gln
625                 630                 635                 640

Ile

<210> SEQ ID NO 63
<211> LENGTH: 726
<212> TYPE: DNA
<213> ORGANISM: Artificial Sequence
<220> FEATURE:
<223> OTHER INFORMATION: IgG1, experimentally altered human sequence

<400> SEQUENCE: 63
tctagagcca ccatggagac cgacaccctc ctcctgtggg tgctgctgct gtgggtgccc      60
ggctctaccg cgagatcgt gctgactcag tctccaggca cactgtctct gtcccctggc     120
gagcgcgcta cactgtcttg cagagcttct cagtccgtga gcagctctta cctcgcttgg    180
tatcagcaga agcctggcca ggcccctaga ctcctgatat acggcgcctc gtctagggct    240

```
acaggcattc cgacaggtt ctccggctct ggcagcggca ccgacttcac actcactatt    300
agccgcctag aacctgagga cttcgccgtg tactactgcc agcagtacgg ctctagccca    360
tgcacattcg gccagggcac aagacttgag atcaagagga ccgtggccgc ccccagcgtg    420
ttcatcttcc ctcccagcga cgagcagctg aagtctggca ccgccagcgt ggtgtgcctg    480
ctgaacaact tctaccccg cgaggccaag gtgcagtgga aggtggacaa cgccctgcag    540
agcggcaaca gccaggagag cgtgaccgag caggactcca aggacagcac ctacagcctg    600
agcagcaccc tgaccctgag caaggccgac tacgagaagc acaaggtgta cgcctgcgag    660
gtgacccacc agggactgtc tagccccgtg accaagagct caaccggggg cgagtgctaa    720
gtcgac                                                                726
```

```
<210> SEQ ID NO 64
<211> LENGTH: 235
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 64

Met Glu Thr Asp Thr Leu Leu Trp Val Leu Leu Trp Val Pro
1               5                   10                  15

Gly Ser Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Val Ser Ser Ser Tyr Leu Ala Trp Tyr Gln Gln Lys Pro Gly Gln Ala
        50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Cys Thr Phe Gly Gln Gly Thr Arg Leu Glu Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 65
<211> LENGTH: 2196
<212> TYPE: DNA
```

<213> ORGANISM: Artificial Sequence
<220> FEATURE:
<223> OTHER INFORMATION: IgG1, experimentally altered human sequence

<400> SEQUENCE: 65

```
ctcgaggcca ccatggagac cgacacactc ctcctgtggg tgctgctgct ctgggtgcca      60
ggcagcaccg gcgaggtgca gttggtggag tccggcggcg gcctcgtgca gccaggcggc     120
tccctgagac tgtcttgcgc cgcttccggc ttcactttct ctaactactg gatgaactgg     180
gtgagacagg ctccaggcaa gggccttgag tgggtggccg ctatcaacca ggacggctcc     240
gagaagtact atgtgggctc tgtgaagggc agattcacaa ttagccgcga caacgctaag     300
aacagcctgt acttacagat gaactctctc agagtggagg acacagctgt gtactactgc     360
gtgcgggact actacgacat cctgaccgac tactacattc actactggta cttcgacctc     420
tggggcagag gcactctggt caccgtgagc tccgccagca caagggccc cagcgtcttc      480
ccactggctc cttcctctaa agcactagc ggagggaccg cagccctggg ctgtctggtg       540
aaagactact ccccgagcc cgtgaccgtc tcctggaact ctggagccct gacctccggg      600
gtgcacacct tcccgccgt gctgcagtct tctggactgt actccctgtc ctccgtcgtg      660
actgtgccca gctcctccct gggaactcag acatacatct gcaacgtgaa ccacaagcct     720
tccaacacaa aggtggacaa gagagtcgag cccaagagct gtgataagac ccatacatgt     780
cccccatgcc ccgctccaga actgctgggc ggaccttccg tgtttctgtt cccacccaaa     840
ccaaaggaca cactgatgat cagcagaacc cctgaggtga cttgcgtggt cgtggacgtg     900
agccatgagg accccgaggt gaagttcaac tggtatgtgg atggcgtgga agtgcataat     960
gccaagacaa aacctaggga agagcagtac aacagcacct acagggtggt gagcgtgctg    1020
accgtgctgc accaggattg gctgaacggc aaggaataca agtgcaaggt gtccaataag    1080
gctctgcctg cacctatcga gaagaccatc agcaaagcca agggccaacc cagagagcct    1140
caagtctaca ccctgccccc aagcagggag gagatgacca aaaatcaagt gagcctgaca    1200
tgcctggtca aaggcttcta ccctagcgac atcgccgtgg agtgggagag caatggccag    1260
cctgagaaca actacaagac cactccccc gtcctggata cgacggcag cttcttcctg      1320
tactccaaac tgacagtcga taaaagcagg tggcagcaag gcaatgtctt tagctgtagc    1380
gtgatgcacg aggccctgca taaccactac actcaaaagt ccctgtccct gagccccgga    1440
ggcggaggat ctggcggcgg aggcagtgga ggcggcggaa gcctgcctgc tcaggtggca    1500
ttcacccccat acgctcctga gcctggctca acttgtaggc tgagagagta ctacgaccag    1560
accgcccaga tgtgctgttc caagtgcagt cctggacagc acgctaaggt gttttgcaca    1620
aagacttccg ataccgtgtg cgatagttgt gaggacagta cttacactca gctgtggaat    1680
tgggtgccag agtgtctctc ttgcggcagt agatgttctt ccgatcaggt cgagacacag    1740
gcttgcactc gcgagcagaa tcgcatttgc acatgtcggc aggatggta ctgcgctctg     1800
tctaagcagg agggctgtag actctgcgcc cctctccgca agtgccgccc cggattcggc    1860
gtcgcacggc ccggaaccga gactagcgac gtcgtctgca gccatgcgc tcccggaacc    1920
tttagtaata acacatcttc tactgatatt tgtaggcctc accagatttg taacgtggtg    1980
gcaattcctg gaaatgcctc tatggacgcc gtgtgtacat ctacatcccc aactagaagt    2040
atggctcccg gcgccgtcca cctccctcag ccgtgagta ctcggagtca gcacactcag    2100
ccaacacccg agccatctac cgcacctcct acctcttttc tgctcccat gggacctagt    2160
ccaccagctg agggtagtac tggcgactaa gaattc                               2196
```

-continued

<210> SEQ ID NO 66
<211> LENGTH: 725
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 66

```
Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Asn Tyr Trp Met Asn Trp Val Arg Gln Ala Pro Gly Lys Gly
    50                  55                  60

Leu Glu Trp Val Ala Ala Ile Asn Gln Asp Gly Ser Glu Lys Tyr Tyr
65                  70                  75                  80

Val Gly Ser Val Lys Gly Arg Phe Thr Ile Ser Arg Asp Asn Ala Lys
                85                  90                  95

Asn Ser Leu Tyr Leu Gln Met Asn Ser Leu Arg Val Glu Asp Thr Ala
            100                 105                 110

Val Tyr Tyr Cys Val Arg Asp Tyr Asp Ile Leu Thr Asp Tyr Tyr
        115                 120                 125

Ile His Tyr Trp Tyr Phe Asp Leu Trp Gly Arg Gly Thr Leu Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Arg Val Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
```

```
                355                 360                 365
Ala Lys Gly Gln Pro Arg Glu Pro Gln Val Tyr Thr Leu Pro Pro Ser
370                 375                 380

Arg Glu Glu Met Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Gly Gly Gly Ser
465                 470                 475                 480

Gly Gly Gly Gly Ser Gly Gly Gly Ser Leu Pro Ala Gln Val Ala
                485                 490                 495

Phe Thr Pro Tyr Ala Pro Glu Pro Gly Ser Thr Cys Arg Leu Arg Glu
                500                 505                 510

Tyr Tyr Asp Gln Thr Ala Gln Met Cys Cys Ser Lys Cys Ser Pro Gly
            515                 520                 525

Gln His Ala Lys Val Phe Cys Thr Lys Thr Ser Asp Thr Val Cys Asp
    530                 535                 540

Ser Cys Glu Asp Ser Thr Tyr Thr Gln Leu Trp Asn Trp Val Pro Glu
545                 550                 555                 560

Cys Leu Ser Cys Gly Ser Arg Cys Ser Ser Asp Gln Val Glu Thr Gln
                565                 570                 575

Ala Cys Thr Arg Glu Gln Asn Arg Ile Cys Thr Cys Arg Pro Gly Trp
            580                 585                 590

Tyr Cys Ala Leu Ser Lys Gln Glu Gly Cys Arg Leu Cys Ala Pro Leu
        595                 600                 605

Arg Lys Cys Arg Pro Gly Phe Gly Val Ala Arg Pro Gly Thr Glu Thr
    610                 615                 620

Ser Asp Val Val Cys Lys Pro Cys Ala Pro Gly Thr Phe Ser Asn Thr
625                 630                 635                 640

Thr Ser Ser Thr Asp Ile Cys Arg Pro His Gln Ile Cys Asn Val Val
                645                 650                 655

Ala Ile Pro Gly Asn Ala Ser Met Asp Ala Val Cys Thr Ser Thr Ser
            660                 665                 670

Pro Thr Arg Ser Met Ala Pro Gly Ala Val His Leu Pro Gln Pro Val
        675                 680                 685

Ser Thr Arg Ser Gln His Thr Gln Pro Thr Pro Glu Pro Ser Thr Ala
    690                 695                 700

Pro Ser Thr Ser Phe Leu Leu Pro Met Gly Pro Ser Pro Pro Ala Glu
705                 710                 715                 720

Gly Ser Thr Gly Asp
                725

<210> SEQ ID NO 67
<211> LENGTH: 743
<212> TYPE: DNA
<213> ORGANISM: Artificial Sequence
<220> FEATURE:
<223> OTHER INFORMATION: IgG1, experimentally altered human sequence
```

<400> SEQUENCE: 67

```
tctagagcca ccatggagac cgacaccctc ctcctgtggg tgctgctgct gtgggtgccc      60
ggctctaccg gcgacatcgt gatgactcag acaccactga gcctgtctgt gaccccaggc     120
cagcccgctt cgatttcttg ccggtcctct cgcagcctgg tgcactctag ggcaacaca     180
tacctccact ggtatctaca gaagcccggc cagtcccctc agctgctgat ctacaaggtg     240
tctaacaggt tcattggcgt gcccgaccgc ttctccggct ctggcagcgg caccgacttc     300
acactcaaga ttagcagagt ggaggctgag gacgtgggcg tgtactactg ctctcagtct     360
acccacctcc ctttcacatt cggccagggc acaaaggtgg agatcaagcg gaccgtggcc     420
gccccatccg tgttcatttt cccaccttcc gacgagcagc tgaagtctgg caccgccagc     480
gtggtgtgcc tgctgaacaa cttctacccc cgcgaggcca aggtgcagtg gaaggtggac     540
aacgccctgc agagcggcaa cagccaggag agcgtgaccg agcaggactc caaggacagc     600
acctacagcc tgagcagcac cctgaccctg agcaaggccg actacgagaa gcacaaggtg     660
tacgcctgcg aggtgaccca ccagggactg tctagccccg tgaccaagag cttcaaccgg     720
ggcgagtgct aagaattgtc gac                                             743
```

<210> SEQ ID NO 68
<211> LENGTH: 239
<212> TYPE: PRT
<213> ORGANISM: Artificial Sequence
<220> FEATURE:
<223> OTHER INFORMATION: Complementarity-determining region (CDR),
      experimentally altered human sequence

<400> SEQUENCE: 68

```
Met Glu Thr Asp Thr Leu Leu Leu Trp Val Leu Leu Leu Trp Val Pro
1               5                   10                  15

Gly Ser Thr Gly Asp Ile Val Met Thr Gln Thr Pro Leu Ser Leu Ser
            20                  25                  30

Val Thr Pro Gly Gln Pro Ala Ser Ile Ser Cys Arg Ser Ser Arg Ser
        35                  40                  45

Leu Val His Ser Arg Gly Asn Thr Tyr Leu His Trp Tyr Leu Gln Lys
    50                  55                  60

Pro Gly Gln Ser Pro Gln Leu Leu Ile Tyr Lys Val Ser Asn Arg Phe
65                  70                  75                  80

Ile Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Leu Pro Phe Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
```

210                 215                 220
Gly Leu Ser Ser Pro Val Thr Lys Ser Phe Asn Arg Gly Glu Cys
225                 230                 235

<210> SEQ ID NO 69
<211> LENGTH: 1962
<212> TYPE: DNA
<213> ORGANISM: Artificial Sequence
<220> FEATURE:
<223> OTHER INFORMATION: IgG1, experimentally altered human sequence

<400> SEQUENCE: 69

| | | | | | |
|---|---|---|---|---|---|
| ctcgaggcca | ccatggagac | cgacacactc | ctcctgtggg | tgctgctgct | ctgggtgcca | 60 |
| ggcagcaccg | gcctgcccgc | acaagtggcc | ttcacccccct | acgcccccaga | gcccggctct | 120 |
| acttgtaggc | tgagggagta | ctacgaccag | accgcccaga | tgtgctgctc | caagtgtagc | 180 |
| cccggacagc | acgccaaggt | gttctgtaca | aagacctccg | acaccgtgtg | cgactcctgc | 240 |
| gaggactcca | cctacaccca | gctgtggaac | tgggtgcccg | agtgcctgtc | ctgcggctcc | 300 |
| aggtgctcct | ctgaccaggt | cgagacccaa | gcctgtacca | gggagcagaa | caggatctgc | 360 |
| acttgcaggc | caggctggta | ttgcgccctg | tccaagcagg | aaggctgcag | gctgtgcgcc | 420 |
| ccactgagga | aatgtaggcc | tgggttcggc | gtggctaggc | ccggaaccga | gacttccgac | 480 |
| gtggtgtgca | gccctgtgc | cctggcacc | ttttccaaca | ccacctcctc | caccgacatc | 540 |
| tgtaggccac | accagattga | caagcgcgtg | gagtccaagt | acggccctcc | ttgccctcct | 600 |
| tgccctgccc | ctgagttcct | gggcggccct | tccgtgttcc | tgttccctcc | taagcctaag | 660 |
| gacaccctga | tgatctcccg | cacccctgag | gtgacctgcg | tggtggtgga | cgtgtcccag | 720 |
| gaggaccctg | aggtgcagtt | caactggtac | gtggacggcg | tggaggtgca | caacgccaag | 780 |
| accaagcctc | gcgaggagca | gttcaactcc | acctaccgcg | tggtgtccgt | gctgaccgtg | 840 |
| ctgcaccagg | actggctgaa | cggcaaggag | tacaagtgca | aggtgtccaa | caagggcctg | 900 |
| ccttcctcca | tcgagaagac | catctccaag | gccaagggcc | agcctcgcga | gcctcaggtg | 960 |
| tacaccctgc | ctccttccca | ggaggagatg | accaagaacc | aggtgtccct | gacctgcctg | 1020 |
| gtgaagggct | tctacccttc | cgacatcgcc | gtggagtggg | agtccaacgg | ccagcctgag | 1080 |
| aacaactaca | agaccacccc | tcctgtgctg | gactccgacg | gctccttctt | cctgtactcc | 1140 |
| cgcctgaccg | tggacaagtc | ccgctggcag | gagggcaacg | tgttctcctg | ctccgtgatg | 1200 |
| cacgaggccc | tgcacaacca | ctacacccag | aagtccctgt | ccctgtccct | gggcggcgga | 1260 |
| ggatctggcg | gcgaggcag | tggaggcggc | ggaagccagg | tgcagctcgt | gcagagcggc | 1320 |
| gccgaggtga | agaagcccgg | ctcttctgtg | aaggtgtctt | gcaaggcttc | cggctactct | 1380 |
| ttcaccgact | accacattca | ctgggtgcgc | caggctcctg | gccagggcct | tgagtggatg | 1440 |
| ggcgtgatta | accctatgta | cggcacaaca | gactacaacc | agcggttcaa | gggcagagtg | 1500 |
| accattacag | ccgacgagtc | cacatccacc | gcttacatgg | agctgtcctc | cctgcgttct | 1560 |
| gaggacactg | ctgtgtacta | ctgcgctaga | tacgactact | tcaccggcac | tggcgtgtac | 1620 |
| tggggccagg | gcacactcgt | gaccgtgtct | agcgcatcaa | caaagggccc | atctgtgttc | 1680 |
| ccactcgccc | catgctcccg | ctccacctcc | gagtccaccg | ccgccctggg | ctgcctggtg | 1740 |
| aaggactact | ccctgagcc | tgtgaccgtg | tcctggaact | ccggcgccct | gacctccggc | 1800 |
| gtgcacacct | ccctgccgt | gctgcagtcc | tccggcctgt | actccctgtc | ctccgtggtg | 1860 |
| accgtgcctt | cctcctccct | gggcaccaag | acctacacct | gcaacgtgga | ccacaagcct | 1920 | tccaacacca aggtggacaa gcgcgtggag tcctaagaat tc                    1962

<210> SEQ ID NO 70
<211> LENGTH: 647
<212> TYPE: PRT
<213> ORGANISM: Artificial Sequence
<220> FEATURE:
<223> OTHER INFORMATION: Complementarity-determining region (CDR), experimentally altered human sequence

<400> SEQUENCE: 70

```
Met Glu Thr Asp Thr Leu Leu Leu Trp Val Leu Leu Leu Trp Val Pro
1               5                   10                  15

Gly Ser Thr Gly Leu Pro Ala Gln Val Ala Phe Thr Pro Tyr Ala Pro
            20                  25                  30

Glu Pro Gly Ser Thr Cys Arg Leu Arg Glu Tyr Tyr Asp Gln Thr Ala
        35                  40                  45

Gln Met Cys Cys Ser Lys Cys Ser Pro Gly Gln His Ala Lys Val Phe
    50                  55                  60

Cys Thr Lys Thr Ser Asp Thr Val Cys Asp Ser Cys Glu Asp Ser Thr
65                  70                  75                  80

Tyr Thr Gln Leu Trp Asn Trp Val Pro Glu Cys Leu Ser Cys Gly Ser
                85                  90                  95

Arg Cys Ser Ser Asp Gln Val Glu Thr Gln Ala Cys Thr Arg Glu Gln
            100                 105                 110

Asn Arg Ile Cys Thr Cys Arg Pro Gly Trp Tyr Cys Ala Leu Ser Lys
        115                 120                 125

Gln Glu Gly Cys Arg Leu Cys Ala Pro Leu Arg Lys Cys Arg Pro Gly
    130                 135                 140

Phe Gly Val Ala Arg Pro Gly Thr Glu Thr Ser Asp Val Val Cys Lys
145                 150                 155                 160

Pro Cys Ala Pro Gly Thr Phe Ser Asn Thr Thr Ser Ser Thr Asp Ile
                165                 170                 175

Cys Arg Pro His Gln Ile Asp Lys Arg Val Glu Ser Lys Tyr Gly Pro
            180                 185                 190

Pro Cys Pro Pro Cys Pro Ala Pro Glu Phe Leu Gly Gly Pro Ser Val
        195                 200                 205

Phe Leu Phe Pro Pro Lys Pro Lys Asp Thr Leu Met Ile Ser Arg Thr
    210                 215                 220

Pro Glu Val Thr Cys Val Val Asp Val Ser Gln Glu Asp Pro Glu
225                 230                 235                 240

Val Gln Phe Asn Trp Tyr Val Asp Gly Val Glu Val His Asn Ala Lys
                245                 250                 255

Thr Lys Pro Arg Glu Glu Gln Phe Asn Ser Thr Tyr Arg Val Val Ser
            260                 265                 270

Val Leu Thr Val Leu His Gln Asp Trp Leu Asn Gly Lys Glu Tyr Lys
        275                 280                 285

Cys Lys Val Ser Asn Lys Gly Leu Pro Ser Ser Ile Glu Lys Thr Ile
    290                 295                 300

Ser Lys Ala Lys Gly Gln Pro Arg Glu Pro Gln Val Tyr Thr Leu Pro
305                 310                 315                 320

Pro Ser Gln Glu Glu Met Thr Lys Asn Gln Val Ser Leu Thr Cys Leu
                325                 330                 335

Val Lys Gly Phe Tyr Pro Ser Asp Ile Ala Val Glu Trp Glu Ser Asn
            340                 345                 350
```

Gly Gln Pro Glu Asn Asn Tyr Lys Thr Thr Pro Pro Val Leu Asp Ser
            355                 360                 365

Asp Gly Ser Phe Phe Leu Tyr Ser Arg Leu Thr Val Asp Lys Ser Arg
        370                 375                 380

Trp Gln Glu Gly Asn Val Phe Ser Cys Ser Val Met His Glu Ala Leu
385                 390                 395                 400

His Asn His Tyr Thr Gln Lys Ser Leu Ser Leu Ser Leu Gly Gly
            405                 410                 415

Gly Ser Gly Gly Gly Gly Ser Gly Gly Gly Ser Gln Val Gln Leu
        420                 425                 430

Val Gln Ser Gly Ala Glu Val Lys Lys Pro Gly Ser Ser Val Lys Val
            435                 440                 445

Ser Cys Lys Ala Ser Gly Tyr Ser Phe Thr Asp Tyr His Ile His Trp
        450                 455                 460

Val Arg Gln Ala Pro Gly Gln Gly Leu Glu Trp Met Gly Val Ile Asn
465                 470                 475                 480

Pro Met Tyr Gly Thr Thr Asp Tyr Asn Gln Arg Phe Lys Gly Arg Val
            485                 490                 495

Thr Ile Thr Ala Asp Glu Ser Thr Ser Thr Ala Tyr Met Glu Leu Ser
        500                 505                 510

Ser Leu Arg Ser Glu Asp Thr Ala Val Tyr Tyr Cys Ala Arg Tyr Asp
        515                 520                 525

Tyr Phe Thr Gly Thr Gly Val Tyr Trp Gly Gln Gly Thr Leu Val Thr
        530                 535                 540

Val Ser Ser Ala Ser Thr Lys Gly Pro Ser Val Phe Pro Leu Ala Pro
545                 550                 555                 560

Cys Ser Arg Ser Thr Ser Glu Ser Thr Ala Ala Leu Gly Cys Leu Val
            565                 570                 575

Lys Asp Tyr Phe Pro Glu Pro Val Thr Val Ser Trp Asn Ser Gly Ala
        580                 585                 590

Leu Thr Ser Gly Val His Thr Phe Pro Ala Val Leu Gln Ser Ser Gly
        595                 600                 605

Leu Tyr Ser Leu Ser Ser Val Val Thr Val Pro Ser Ser Ser Leu Gly
        610                 615                 620

Thr Lys Thr Tyr Thr Cys Asn Val Asp His Lys Pro Ser Asn Thr Lys
625                 630                 635                 640

Val Asp Lys Arg Val Glu Ser
            645

<210> SEQ ID NO 71
<211> LENGTH: 738
<212> TYPE: DNA
<213> ORGANISM: Artificial Sequence
<220> FEATURE:
<223> OTHER INFORMATION: IgG1, experimentally altered human sequence

<400> SEQUENCE: 71
tctagagcca ccatggagac cgacacactc ctcctgtggg tgctgctgct ctgggtgcca       60
ggcagcaccg ccaggtgca gctcgtgcag agcggcgccg aggtgaagaa gcccggctct      120
tctgtgaagg tgtcttgcaa ggcttccggc tactcttttca ccgactacca cattcactgg      180
gtgcgccagg ctcctggcca gggccttgag tggatgggcg tgattaaccc tatgtacggc      240
acaacagact acaaccagcg gttcaagggc agagtgacca ttacagccga cgagtccaca      300
tccaccgctt acatggagct gtcctccctg cgttctgagg acactgctgt gtactactgc      360

```
gctagatacg actacttcac cggcactggc gtgtactggg gccagggcac actcgtgacc    420
gtgtctagcg catcaacaaa gggcccatct gtgttcccac tcgccccatg ctcccgctcc    480
acctccgagt ccaccgccgc cctgggctgc ctggtgaagg actacttccc tgagcctgtg    540
accgtgtcct ggaactccgg cgccctgacc tccggcgtgc acaccttccc tgccgtgctg    600
cagtcctccg gcctgtactc cctgtcctcc gtggtgaccg tgccttcctc ctccctgggc    660
accaagacct acacctgcaa cgtggaccac aagccttcca acaccaaggt ggacaagcgc    720
gtggagtcct aagtcgac                                                   738
```

<210> SEQ ID NO 72
<211> LENGTH: 239
<212> TYPE: PRT
<213> ORGANISM: Artificial Sequence
<220> FEATURE:
<223> OTHER INFORMATION: Complementarity-determining region (CDR), experimentally altered human sequence

<400> SEQUENCE: 72

```
Met Glu Thr Asp Thr Leu Leu Leu Trp Val Leu Leu Leu Trp Val Pro
1               5                   10                  15

Gly Ser Thr Gly Gln Val Gln Leu Val Gln Ser Gly Ala Glu Val Lys
            20                  25                  30

Lys Pro Gly Ser Ser Val Lys Val Ser Cys Lys Ala Ser Gly Tyr Ser
        35                  40                  45

Phe Thr Asp Tyr His Ile His Trp Val Arg Gln Ala Pro Gly Gln Gly
    50                  55                  60

Leu Glu Trp Met Gly Val Ile Asn Pro Met Tyr Gly Thr Thr Asp Tyr
65                  70                  75                  80

Asn Gln Arg Phe Lys Gly Arg Val Thr Ile Thr Ala Asp Glu Ser Thr
                85                  90                  95

Ser Thr Ala Tyr Met Glu Leu Ser Ser Leu Arg Ser Glu Asp Thr Ala
            100                 105                 110

Val Tyr Tyr Cys Ala Arg Tyr Asp Tyr Phe Thr Gly Thr Gly Val Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser
225                 230                 235
```

<210> SEQ ID NO 73
<211> LENGTH: 1962
<212> TYPE: DNA
<213> ORGANISM: Artificial Sequence
<220> FEATURE:
<223> OTHER INFORMATION: IgG1, experimentally altered human sequence

<400> SEQUENCE: 73

```
ctcgaggcca ccatggagac cgacacactc ctcctgtggg tgctgctgct ctgggtgcca      60
ggcagcaccg gcctgcccgc acaagtggcc ttcacccccct acgccccaga gcccggctct    120
acttgtaggc tgagggagta ctacgaccag accgcccaga tgtgctgctc caagtgtagc    180
cccggacagc acgccaaggt gttctgtaca aagacctccg acaccgtgtg cgactcctgc    240
gaggactcca cctacaccca gctgtggaac tgggtgcccg agtgcctgtc ctgcggctcc    300
aggtgctcct ctgaccaggt cgagacccaa gcctgtacca gggagcagaa caggatctgc    360
acttgcaggc caggctggta ttgcgccctg tccaagcagg aaggctgcag gctgtgcgcc    420
ccactgagga aatgtaggcc tgggttcggc gtggctaggc ccggaaccga gacttccgac    480
gtggtgtgca agccctgtgc cctggcacc ttttccaaca ccacctcctc caccgacatc    540
tgtaggccac accagattga caagcgcgtg gagtccaagt acggccctcc ttgccctcct    600
tgccctgccc ctgagttcct gggcggccct tccgtgttcc tgttccctcc taagcctaag    660
gacaccctga tgatctcccg caccccctgag gtgacctgcg tggtggtgga cgtgtcccag    720
gaggaccctg aggtgcagtt caactggtac gtggacggcg tggaggtgca caacgccaag    780
accaagcctc gcgaggagca gttcaactcc acctaccgcg tggtgtccgt gctgaccgtg    840
ctgcaccagg actggctgaa cggcaaggag tacaagtgca aggtgtccaa caagggcctg    900
ccttcctcca tcgagaagac catctccaag gccaagggcc agcctcgcga gcctcaggtg    960
tacaccctgc ctccttccca ggaggagatg accaagaacc aggtgtccct gacctgcctg   1020
gtgaagggct tctacccttc cgacatcgcc gtggagtggg agtccaacgg ccagcctgag   1080
aacaactaca agaccacccc tcctgtgctg gactccgacg gctccttctt cctgtactcc   1140
cgcctgaccg tggacaagtc ccgctggcag gagggcaacg tgttctcctg ctccgtgatg   1200
cacgaggccc tgcacaacca ctacacccag aagtccctgt ccctgtccct gggcggcgga   1260
ggatctggcg gcggaggcag tggaggcggc ggaagcgaca tcgtgatgac tcagacacca   1320
ctgagcctgt ctgtgacccc aggccagccc gcttcgattt cttgccggtc ctctcgcagc   1380
ctggtgcact ctaggggcaa cacatacctc cactggtatc tacagaagcc cggccagtcc   1440
cctcagctgc tgatctacaa ggtgtctaac aggttcattg gcgtgcccga ccgcttctcc   1500
ggctctggca gcggcaccga cttcacactc aagattagca gagtggaggc tgaggacgtg   1560
ggcgtgtact actgctctca gtctacccac ctcccttttca cattcggcca gggcacaaag   1620
gtggagatca gcggaccgt ggccgcccca tccgtgttca ttttcccacc ttccgacgag   1680
cagctgaagt ctggcaccgc cagcgtggtg tgcctgctga caacttcta cccccgcgag   1740
gccaaggtgc agtggaaggt ggacaacgcc ctgcagagcg gcaacagcca ggagagcgtg   1800
accgagcagg actccaagga cagcacctac agcctgagca gcaccctgac cctgagcaag   1860
gccgactacg agaagcacaa ggtgtacgcc tgcgaggtga cccaccaggg actgtctagc   1920
cccgtgacca gagcttcaa ccggggcgag tgctaagaat tc                       1962
```

<210> SEQ ID NO 74
<211> LENGTH: 647
<212> TYPE: PRT
<213> ORGANISM: Artificial Sequence
<220> FEATURE:
<223> OTHER INFORMATION: Complementarity-determining region (CDR), experimentally altered human sequence

<400> SEQUENCE: 74

Met Glu Thr Asp Thr Leu Leu Leu Trp Val Leu Leu Leu Trp Val Pro

-continued

```
1               5                   10                  15
Gly Ser Thr Gly Leu Pro Ala Gln Val Ala Phe Thr Pro Tyr Ala Pro
                20                  25                  30

Glu Pro Gly Ser Thr Cys Arg Leu Arg Glu Tyr Tyr Asp Gln Thr Ala
            35                  40                  45

Gln Met Cys Cys Ser Lys Cys Ser Pro Gly Gln His Ala Lys Val Phe
        50                  55                  60

Cys Thr Lys Thr Ser Asp Thr Val Cys Asp Ser Cys Glu Asp Ser Thr
65                  70                  75                  80

Tyr Thr Gln Leu Trp Asn Trp Val Pro Glu Cys Leu Ser Cys Gly Ser
                85                  90                  95

Arg Cys Ser Ser Asp Gln Val Glu Thr Gln Ala Cys Thr Arg Glu Gln
            100                 105                 110

Asn Arg Ile Cys Thr Cys Arg Pro Gly Trp Tyr Cys Ala Leu Ser Lys
        115                 120                 125

Gln Glu Gly Cys Arg Leu Cys Ala Pro Leu Arg Lys Cys Arg Pro Gly
    130                 135                 140

Phe Gly Val Ala Arg Pro Gly Thr Glu Thr Ser Asp Val Val Cys Lys
145                 150                 155                 160

Pro Cys Ala Pro Gly Thr Phe Ser Asn Thr Thr Ser Ser Thr Asp Ile
                165                 170                 175

Cys Arg Pro His Gln Ile Asp Lys Arg Val Glu Ser Lys Tyr Gly Pro
            180                 185                 190

Pro Cys Pro Pro Cys Pro Ala Pro Glu Phe Leu Gly Gly Pro Ser Val
        195                 200                 205

Phe Leu Phe Pro Pro Lys Pro Lys Asp Thr Leu Met Ile Ser Arg Thr
210                 215                 220

Pro Glu Val Thr Cys Val Val Val Asp Val Ser Gln Glu Asp Pro Glu
225                 230                 235                 240

Val Gln Phe Asn Trp Tyr Val Asp Gly Val Glu Val His Asn Ala Lys
                245                 250                 255

Thr Lys Pro Arg Glu Glu Gln Phe Asn Ser Thr Tyr Arg Val Val Ser
            260                 265                 270

Val Leu Thr Val Leu His Gln Asp Trp Leu Asn Gly Lys Glu Tyr Lys
        275                 280                 285

Cys Lys Val Ser Asn Lys Gly Leu Pro Ser Ser Ile Glu Lys Thr Ile
    290                 295                 300

Ser Lys Ala Lys Gly Gln Pro Arg Glu Pro Gln Val Tyr Thr Leu Pro
305                 310                 315                 320

Pro Ser Gln Glu Glu Met Thr Lys Asn Gln Val Ser Leu Thr Cys Leu
                325                 330                 335

Val Lys Gly Phe Tyr Pro Ser Asp Ile Ala Val Glu Trp Glu Ser Asn
            340                 345                 350

Gly Gln Pro Glu Asn Asn Tyr Lys Thr Thr Pro Pro Val Leu Asp Ser
        355                 360                 365

Asp Gly Ser Phe Phe Leu Tyr Ser Arg Leu Thr Val Asp Lys Ser Arg
    370                 375                 380

Trp Gln Glu Gly Asn Val Phe Ser Cys Ser Val Met His Glu Ala Leu
385                 390                 395                 400

His Asn His Tyr Thr Gln Lys Ser Leu Ser Leu Ser Leu Gly Gly Gly
                405                 410                 415

Gly Ser Gly Gly Gly Gly Ser Gly Gly Gly Gly Ser Asp Ile Val Met
            420                 425                 430
```

```
Thr Gln Thr Pro Leu Ser Leu Ser Val Thr Pro Gly Gln Pro Ala Ser
        435                 440                 445

Ile Ser Cys Arg Ser Ser Arg Ser Leu Val His Ser Arg Gly Asn Thr
    450                 455                 460

Tyr Leu His Trp Tyr Leu Gln Lys Pro Gly Gln Ser Pro Gln Leu Leu
465                 470                 475                 480

Ile Tyr Lys Val Ser Asn Arg Phe Ile Gly Val Pro Asp Arg Phe Ser
                485                 490                 495

Gly Ser Gly Ser Gly Thr Asp Phe Thr Leu Lys Ile Ser Arg Val Glu
            500                 505                 510

Ala Glu Asp Val Gly Val Tyr Tyr Cys Ser Gln Ser Thr His Leu Pro
        515                 520                 525

Phe Thr Phe Gly Gln Gly Thr Lys Val Glu Ile Lys Arg Thr Val Ala
    530                 535                 540

Ala Pro Ser Val Phe Ile Phe Pro Pro Ser Asp Glu Gln Leu Lys Ser
545                 550                 555                 560

Gly Thr Ala Ser Val Val Cys Leu Leu Asn Asn Phe Tyr Pro Arg Glu
                565                 570                 575

Ala Lys Val Gln Trp Lys Val Asp Asn Ala Leu Gln Ser Gly Asn Ser
            580                 585                 590

Gln Glu Ser Val Thr Glu Gln Asp Ser Lys Asp Ser Thr Tyr Ser Leu
        595                 600                 605

Ser Ser Thr Leu Thr Leu Ser Lys Ala Asp Tyr Glu Lys His Lys Val
    610                 615                 620

Tyr Ala Cys Glu Val Thr His Gln Gly Leu Ser Ser Pro Val Thr Lys
625                 630                 635                 640

Ser Phe Asn Arg Gly Glu Cys
                645

<210> SEQ ID NO 75
<211> LENGTH: 227
<212> TYPE: PRT
<213> ORGANISM: Artificial Sequence
<220> FEATURE:
<223> OTHER INFORMATION: IgG1, experimentally altered human sequence

<400> SEQUENCE: 75

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140
```

```
Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225

<210> SEQ ID NO 76
<211> LENGTH: 232
<212> TYPE: PRT
<213> ORGANISM: Artificial Sequence
<220> FEATURE:
<223> OTHER INFORMATION: IgG2, experimentally altered human sequence

<400> SEQUENCE: 76

Asp Lys Thr Val Glu Arg Lys Cys Cys Val Glu Cys Pro Pro Cys Pro
1               5                   10                  15

Ala Pro Pro Val Ala Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Gln Phe Asn Trp Tyr Val
    50                  55                  60

Asp Gly Val Glu Val His Asn Ala Lys Thr Lys Pro Arg Glu Glu Gln
65                  70                  75                  80

Phe Asn Ser Thr Phe Arg Val Val Ser Val Leu Thr Val Val His Gln
                85                  90                  95

Asp Trp Leu Asn Gly Lys Glu Tyr Lys Cys Lys Val Ser Asn Lys Gly
            100                 105                 110

Leu Pro Ala Pro Ile Glu Lys Thr Ile Ser Lys Thr Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 77
<211> LENGTH: 233
<212> TYPE: PRT
<213> ORGANISM: Artificial Sequence
```

```
<220> FEATURE:
<223> OTHER INFORMATION: IgG4, experimentally altered human sequence

<400> SEQUENCE: 77

Asp Lys Arg Val Glu Ser Lys Tyr Gly Pro Pro Cys Pro Pro Cys Pro
1               5                   10                  15

Ala Pro Glu Phe Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser Gln Glu Asp Pro Glu Val Gln Phe Asn Trp Tyr
    50                  55                  60

Val Asp Gly Val Glu Val His Asn Ala Lys Thr Lys Pro Arg Glu Glu
65                  70                  75                  80

Gln Phe Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Gly Leu Pro Ser Ser Ile Glu Lys Thr Ile Ser Lys Ala Lys Gly Gln
        115                 120                 125

Pro Arg Glu Pro Gln Val Tyr Thr Leu Pro Pro Ser Gln Glu Glu Met
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Arg Leu Thr Val Asp Lys Ser Arg Trp Gln Glu Gly Asn Val
        195                 200                 205

Phe Ser Cys Ser Val Met His Glu Ala Leu His Asn His Tyr Thr Gln
    210                 215                 220

Lys Ser Leu Ser Leu Ser Leu Gly Lys
225                 230

<210> SEQ ID NO 78
<211> LENGTH: 20
<212> TYPE: PRT
<213> ORGANISM: Artificial Sequence
<220> FEATURE:
<223> OTHER INFORMATION: artificially made signal sequence

<400> SEQUENCE: 78

Met Glu Thr Asp Thr Leu Leu Leu Trp Val Leu Leu Leu Trp Val Pro
1               5                   10                  15

Gly Ser Thr Gly
            20
```